United States Patent [19]

Pereira et al.

[11] Patent Number: 5,458,874
[45] Date of Patent: Oct. 17, 1995

[54] METHOD OF INCREASING MONOCYTE CHEMOTAXIS WITH CAP37 AND MONOCYTE CHEMOTACTIC PORTIONS THEREOF

[75] Inventors: Heloise A. Pereira; John K. Spitznagel, both of Decatur, Ga.

[73] Assignee: Emory University, Atlanta, Ga.

[21] Appl. No.: 969,931

[22] Filed: Oct. 30, 1992

Related U.S. Application Data

[63] Continuation of Ser. No. 855,417, Mar. 18, 1992, which is a continuation-in-part of Ser. No. 543,151, Jun. 25, 1990, abandoned, which is a continuation-in-part of Ser. No. 375,739, Jul. 5, 1989, abandoned.

[51] Int. Cl.$^6$ .......................... A61K 38/19; A61K 38/17; A61K 38/04; A61K 38/03
[52] U.S. Cl. ................ 424/85.1; 514/12; 514/21; 435/212
[58] Field of Search ................ 514/12, 21; 530/350; 435/212; 424/85.1

[56] References Cited

U.S. PATENT DOCUMENTS

| | | | |
|---|---|---|---|
| 4,394,443 | 7/1983 | Weissman et al. | 435/6 |
| 4,405,601 | 9/1983 | McEntire et al. | 424/95 |
| 4,427,660 | 1/1984 | Schiffman et al. | 424/177 |
| 4,439,199 | 3/1984 | Amkraut et al. | 604/894 |
| 4,452,735 | 6/1984 | Wissler | 260/112 |
| 4,512,970 | 4/1985 | Wissler | 424/85 |
| 4,512,971 | 4/1985 | Wissler | 424/85 |
| 4,727,028 | 2/1988 | Santiere et al. | 435/240.2 |
| 4,889,919 | 12/1989 | Murray et al. | 530/351 |
| 5,087,569 | 2/1992 | Gabay et al. | 435/212 |
| 5,089,274 | 2/1992 | Marra et al. | 424/534 |
| 5,126,257 | 6/1992 | Gabay et al. | 435/212 |

OTHER PUBLICATIONS

Almeida et al., Biochemical and Biophysical Research Communications 177:688–695 (1991).
Stedman's Medical Dictionary, Waverly Press, Inc., Baltimore, Md., p. 1051 (1982).
Hans Flodgaard et al., "Covalent Structure of Two Novel Neutrophile Leucocyte–Derived Proteins of Porcine and Human Origin," *Eur. J. Biochem.*, 197:535–547 (1991).
Karen R. Wasiluk et al., "Comparison of Granule Proteins from Human Polmorphonuclear Leukocytes Which are Bactericidal Toward," *Infection and Immunity*, 59(11):4193–4200 (Nov. 1991).
Chean Eng Ooi et al., "Endotoxin–Neutralizing Properties of the 25 kD N–Terminal Fragment and a Newly Isolated 30kD C–Terminal Fragment of the 55–60 kD Bactericidal/Permeability–Increasing Protein of Human Neutrophils," *J. Exp. Med.*, 174:649–655 (Sep. 1991).
Marian N. Marra et al., "Bactericidal/Permeability–Increasing Protein has Endotoxin–Neutralizing Activity," *The Journal of Immunology*, 144:(2)662–666 (Jan. 15, 1990).

(List continued on next page.)

*Primary Examiner*—Keith C. Furman
*Attorney, Agent, or Firm*—Needle & Rosenberg

[57] ABSTRACT

Disclosed is a homogeneously pure monocyte chemotactic protein, CAP37, and the entire coding sequences for unprocessed and mature human CAP37 protein. Further, the recombinant production, from nucleic acid coding sequences, of mature CAP37 protein and the mature protein with amino-terminal and/or carboxy-terminal extensions is described. Also disclosed are methods to identify and recombinantly produce bioactive peptides derived from the CAP37 protein coding sequence which are effective chemoattractants monocytes and/or are capable of binding bacterial lipopolysaccharide. A method of preparing homogeneously pure CAP37 using hydrophobic HPLC is described. Bioactive peptide fragments of CAP37 having chemotactic, antibacterial and/or LPS-binding activity are disclosed. Finally, methods of treating wounds, diseased tissue, such as tumors, and infections are described.

4 Claims, 20 Drawing Sheets

OTHER PUBLICATIONS

Joelle E. Gabay et al., "Antibiotic Proteins of Human Polymorphonuclear Leukocytes," *Proc. Natl. Acad. Sci USA*, 86:5610–5614 (Jul. 1989).

Peter S. Tobias et al., "Identification of a Lipid a Binding Site in the Acute Phase Reactant Lipopolysaccharide Binding Protein," *The Journal of Biological Chemistry*, 264(18):10867–10871 (1989).

Ralf R. Schumann et al., "Structure and Function of Lipopolysaccharide Binding Protein," *Reports*, pp. 1429–1431 (Sep. 21, 1990).

M. Schaechter et al., "Mechanisms of Microbiological Disease," *Biology of Infectious Agents*, pp. 26–27 (1989).

Peter S. Tobias et al., "A Family of Lipopolysaccharide Binding Proteins Involved in Responses to Gram-negative Sepsis," *Communication*, 263(27):13479–13481 (1988).

William M. Shafer et al., "Lipid A and Resistance of *Salmonella typhimurium* to Antimicrobial Granule Proteins of Humanneutrophil Granulocytes," *Infection and Immunity*, 43(3):834–838 (Mar. 1984).

Shafer, et al., "Late Intraphogosomal Hydrogen Ion Concentration Favors The In Vitro Antimicrobial Capacity of a 37-Kilodalton Cationic Granule Protein of Human Neutrophil Granulocytes," *Infec. and Immun.* 53(3): 651, 1986.

Shafer, et al., "Cationic Antimicrobial Proteins Isolated From Human Neutraphil Granulocytes In The Presence of Diisopropyl Fluorophosphate," *Infec. and Immun.* 45(1): 29, 1984.

Spitznagel, et al., "Neutrophil Killing of Bacteria by Oxygen-Independent Mechanisms: a historical summary," *Rev. Infect. Diseases* 7(3): 398, 1985.

Pruzanski, et al., "Modulation of Phagocytosis And Intracellular Bactericidal Sidal Activity of Polymorphonuclear and Mononuclear Cells By Cationic Proteins From Human Granulocytes," *Inflammation* 8(4): 445, 1984.

Spitznagel, "Nonoxidative Antimicrobial Reactions of Leukocytes," in *Regulation of Leukocyte Function*, Snyderman (ed.), Plenum Publishing Corp., 1984.

Herion, et al., "That Biological Activities of Granulocyte Lysosomal Cationic Proteins," in *The Pathogenicity of Cationic Proteins*, Lambert, et al. (eds.), (Raven press, New York, 1983).

Pruzanski, et al., "Phagocytic Enhancement of Granulocytes and Monocytes By Cationic Proteins From Human Polymorphonuclear Leukocytes," *Adv. Exp. Med. Biol.* 155:161, 1982.

Senn, et al., "Adjuvant Chemoimmunotherapy With IMF+ BCG In Node-Negative and Node-Positive Breast Cancer Patients: 10-year results," *Eur. J. Cancer Clin. Oncol.* 25:513, 1989.

Cumming, et al., "Intravesical Evans Bacille Calmette-Guérin In The Treatment of Carcinoma In Situ", *Brit. J. Urology* 63: 259, 1989.

Martinez-Piñeiro, et al., "Spontaneous Regression of Pulmonary Metastisis and Long-Term Survival of A Patient With Metastatic Renal Cell Carcinoma, After Immunostimulation With Bacillus Calmette-Guérin and Extirpation of Brain and Contralateral Lung Metastasis," *Eur. Urol.* 15: 146, 1988.

Rosenthal, "Surgery, Recall Antigens, Immunity, and Bacillus Calmette-Guérin Vaccination," *Am. J. Surgery* 156: 1, 1988.

Regelson, et al., "The Routinization of Intraperitoneal (Intracavity) Chemotherapy and Immunotherapy," *Can. Invest.* 4(1): 19, 1986.

Hollinshead, "Immunotherapy Trials: Current Status and Future Directions With Special Emphasis on Biologic Drugs," *Springer Seminars In Immunopathology* 9:85, (1986).

Fidler, "Activation of Macrophages By Liposomes Containing Both Lymphokines and Muramul Dipeptide For the Treatment of Heterogeneous Metastasis," in *Developmenht of Target-Oriented Anticancer Drugs*, Cheng, et al. (eds.), Raven Press, New York, 1983.

Shichiyo et al. 1989. Abstract-Biosis No. 88054394 of Int. J. Biochem 21(4):433–438.

Leonard et al. 1976. Abstract-Biosis No. 63020997 of Cellular Immunology 26(2):200–210.

Pongor, S. 1987. Methods in Enzymology 154:450–473.

Bowie et al. 1990. Science 247:1306–1310.

Alberts et al. 1983. *Molecular Biology of the Cell, Garland Publishing Inc., New York, N.Y. pp. 185–196.*

Meyer-Ingold, 1993. Fibtech, 11:387–392.

Altman, L. K., Apr. 6, 1993. The New York Times, C3.

|AMINO TERMINUS

```
I-V-G-G-R-K-A-R-P-R-Q-F-P-F-L-A-S-I-Q-N-Q-G-R-H-F————————C-
>>>>>>>>>>>>>>>>>>>>> T22>>>>>>>>>>>>>>>>>>>>>>>>>>>>>>>>>>>>>>
                ———T10————————    ————T12————
            ———PE-T22————————   ————PE-T12-

G-G-A-L-I-H-A-R-F-V-M-T-A-A-S-C-F-Q-S-Q-N-X-G-V-I-T-X-L-
>>>>>>>>>>>>>>>>>>>>>>>>>>
——————————————T12———————————————————
——————

A-G-T-R-C-Q-V-A-G-W-G-S-Q-R-S-G-G-R-L-S-R-F-P-R
——————————PE-V10——————

F-V-N-V-T-V-T-P-E-D-Q-C-R-P-N-N-V-C-T-G-V-L-T-R-R-G-G-I-C-N
————  PE-V10—————————————————————————
G-D-G-G-T-P-L-V-C-E-G-L-A-X-G-
————  PE-V10——————

G-P-D-F-F-T-X-V-A-L-F-R-D-W-I-D————G-V-L-N-N-P-G-P
————PE-T13————  ———T15&PE-T30————————
-PE-T12——  —————————PE-T19————(T)
                              CARBOXY TERMINUS|
```

FIG.1

```
          1                    10                    20
CAP37   I-V-G-G-R-K-A-R-P-R-Q-F-P-F-L-A-S-I-Q-N-Q-G-R-H-F——
ELAST   I-V-G-G-R-R-A-R-P-H-A-W-P-F-M-V-S-L-Q-L-R-G-G-H-F——
FACTD   I-L-G-G-R-E-A-E-A-H-A-R-P-Y-M-A-S-V-Q-L-N-G-A-E-L——
PLASM   I-V-G-G-C-V-S-K-P-H-S-W-P-W-Q-V-S-L-R-R-S-S-R-H-F——
CATG    I-I-G-G-R-E-S-R-P-H-S-R-P-Y-M-A-Y-L-Q-I-Q-S-P-A-G-Q-
RMCPI   I-I-G-G-V-E-S-R-P-H-S-R-P-Y-M-A-H-L-E-I-T-T-E-R-G-Y-
RMCPII  I-I-G-G-V-E-S-I-P-H-S-R-P-Y-M-A-H-L-D-I-V-T-E-K-G-L-
CCPI    I-I-G-G-H-E-V-K-P-H-S-R-P-Y-M-A-L-L-S-I-K-D-Q-Q-P-E-
HF      I-I-G-G-D-T-V-V-P-H-S-R-P-Y-M-A-L-L-K-L-S-S-N-T——

▼                          * ▼
CAP37   ————C-G-G-A-L-I-H-A-R-F-V-M-T-A-A-S-C-   42
ELAST   ————C-G-A-T-L-I-A-P-N-F-V-M-S-A-A-H-C-   42
FACTD   ————C-G-G-V-L-V-A-E-Q-W-V-L-T-A-A-H-C-   42
PLASM   ————C-G-G-T-L-I-S-P-K-W-V-L-T-A-A-H-C-   42
CATG    S-R——C-G-G-F-L-V-R-E-D-F-V-L-T-A-A-H-C-   45
RMCP1   K-A-T-C-G-G-F-L-V-N-R-N-F-V-M-T-A-A-H-C-  46
RMCPII  R-V-I-C-G-G-F-L-I-S-R-Q-F-V-L-T-A-A-H-C-  46
CCPI    A———I-C-G-G-F-L-I-R-E-D-F-V-L-T-A-A-H-C-  45
HF      ————I-C-A-G-A-L-I-E-K-N-W-V-L-T-A-A-H-C-  42
```

FIG.4

T7 PRIMER
CMV/T7 PROMOTERS→+1          HindIII
CTATAGTGAGTCGTATTAGAGACCGGAAGCTT

KpnI   SacI   BamHI  SpeI   XmaIII
GGTACCGAGCTCGGATCCACTAGTAACGGCCG

BstXI         EcoRI  PstI   EcoRV BstXI
CCAGTGTGCTGGAATTCTGCAGATATCCATCACACTG

NotI    XhoI   SphI   XbaI   ApaI  +1← Sp6PROMOTER
GCGGCCGCTCGAGCATGCATCTAGAGGGCCCTATAGTGTCACCTAAAT

```
                                                              CC    2

ATCTGTGCTAGGGCCCGGCTGCCAGGGCAGAACTCAGACTTAAAGCACAGAGAAG  57

GCAAGCGGCTTGGCCTGGGTCACACAGCCAGCCCGGCCTGGACGATCCCGCGAAA  112

GGCGTGAGGGCGGACGGTGTGCGGGACTCAGGGGCCCCCCTGTCCTCTTAGGGAG  168

TGGGACG ATG GGG GAC GGT GGG TCC CCC CGC AGC CCC ACT GGG  211
                MET Gly Glu Gly Gly Ser Pro Arg Ser Pro Thr Gly
                -48                                         -37
        TGG ATA GAG CTG AGG CTG CAG CTT CAC ACC CCC TCC CGG CCA  253
        Trp Ile Glu Leu Arg Leu Gln Leu His Thr Pro Ser Arg Pro
                                                            -23
        CTG TGT GGA TTC TTG GGG ATC TCA GAG CTG TCT CCC CCC GAC  295
        Leu Cys Gly Phe Leu Gly Ile Ser Glu Leu Ser Pro Pro Asp
                                                            -9
        CCA GGC TCC AGC CCC CTT TTG GAC ATC GTT GGC GGC CGG AAG  337
        Pro Gly Ser Ser Pro Leu Leu Asp Ile Val Gly Gly Arg Lys
                                   1                          6
        GCG AGG CCC CGC CAG TTC CCG TTC CTG GCC TCC ATT CAG AAT  379
        Ala Arg Pro Arg Gln Phe Pro Phe Leu Ala Ser Ile Gln Asn
                                                            20
        CAA GGC AGG CAC TTC TGC GGG GGT GCC CTG ATC CAT GCC CGC  421
        Gln Gly Arg His Phe Cys Gly Gly Ala Leu Ile His Ala Arg
                                                            34
        TTC GTG ATG ACC GCG GCC AGC TGC TTC CAA AGC CAG AAC CCC  463
        Phe Val MET Thr Ala Ala Ser Cys Phe Gln Ser Gln Asn Pro
                                                            48
        GGG GTT AGC ACC GTG GTC CTG GGT GCC TAT GAC CTG AGG CGG  505
        Gly Val Ser Thr Val Val Leu Gly Ala Tyr Asp Leu Arg Arg
                                                            62
        CGG GAG AGG CAG TCC CGC CAG ACG TTT TCC ATC AGC AGC ATG  547
        Arg Glu Arg Gln Ser Arg Gln Thr Phe Ser Ile Ser Ser MET
                                                            76
        AGC GAG AAT GGC TAC GAC CCC CAG CAG AAC CTG AAC GAC CTG  589
        Ser Glu Asn Gly Tyr Asp Pro Gln Gln Asn Leu Asn Asp Leu
                                                            90
        ATG CTG CTT CAG AGG TTT GTC AAC GTG ACT GTG ACC CCC GAG  631
        MET Leu Leu Gln Arg Phe Val Asn Val Thr Val Thr Pro Glu
                                                            104
```

FIG.6A

```
GAC CAG TGT CGC CCC AAC AAC GTG TGC ACC GGT GTG CTC ACC   673
Asp Gln Cys Arg Pro Asn Asn Val Cys Thr Gly Val Leu Thr
                                                    118
CGC CGC GGT GGC ATC TGC AAT GGG GAC GGG GGC ACC CCC CTC   715
Arg Arg Gly Gly Ile Cys Asn Gly Asp Gly Gly Thr Pro Leu
                                                    132
GTC TGC GAG GGC CTG GCC CAC GGC GTG GCC TCC TTT TCC CTG   757
Val Cys Glu Gly Leu Ala His Gly Val Ala Ser Phe Ser Leu
                                                    146
GGG CCC TGT GGC CGA GGC CCT GAC TTC TTC ACC CGA GTG GCG   799
Gly Pro Cys Gly Arg Gly Pro Asp Phe Phe Thr Arg Val Ala
                                                    160
CTC TTC CGA GAC TGG ATC GAT GGT GTT CTC AAC AAC CCG GGA   841
Leu Phe Arg Asp Trp Ile Asp Gly Val Leu Asn Asn Pro Gly
                                                    174
CCG GGG CCA GCC TAG GGGGGCCTGTGACCTCCCATGGAGCCCAGCCCCGC   891
Pro Gly Pro Ala End
            178
CCTCCACACCTCCGGCGCTCCGCACCCACCTCCCACGGCCCCGCCCCTGCCCCCG  946

TCCGGCCAGAGGGGCCCTGGCTGTAATAAAGAAGCCGATCTCTCCTCTGAAA     998
```

FIG. 6B

```
CCC ATG ACC CGG CTG ACA GTC CTG GCC CTG CTG GCT GGT CTG    42
    MET Thr Arg Leu Thr Val Leu Ala Leu Leu Ala Gly Leu
    -26                ↓       ↓                    -14
                ↓
CTG GCG TCC TCG AGG GCC GGC TCC AGC CCC CTT TTG GAC ATC    84
Leu Ala Ser Ser Arg Ala Gly Ser Ser Pro Leu Leu Asp Ile
                                                    1
GTT GGC GGC CGG AAG GCG AGG CCC CGC CAG TTC CCG TTC CTG   126
Val Gly Gly Arg Lys Ala Arg Pro Arg Gln Phe Pro Phe Leu
                                                    15
GCC TCC ATT CAG AAT CAA GGC AGG CAC TTC TGC GGG GGT GCC   168
Ala Ser Ile Gln Asn Gln Gly Arg His Phe Cys Gly Gly Ala
                                                    29
CTG ATC CAT GCC CGC TTC GTG ATG ACC GCG GCC AGC TGC TTC   210
Leu Ile His Ala Arg Phe Val MET Thr Ala Ala Ser Cys Phe
                                                    43
CAA AGC CAG AAC CCC GGG GTT AGC ACC GTG GTG CTG GGT GCC   252
Gln Ser Gln Asn Pro Gly Val Ser Thr Val Val Leu Gly Ala
                                                    57
TAT GAC CTG AGG CGG CGG GAG AGG CAG TCC CGC CAG ACG TTT   294
Tyr Asp Leu Arg Arg Arg Glu Arg Gln Ser Arg Gln Thr Phe
                                                    71
TCC ATC AGC AGC ATG AGC GAG AAT GGC TAC GAC CCC CAG CAG   336
Ser Ile Ser Ser MET Ser Glu Asn Gly Tyr Asp Pro Gln Gln
                                                    85
AAC CTG AAC GAC CTG ATG CTG CTT CAG CTG GAC CGT GAG GCC   378
Asn Leu Asn Asp Leu MET Leu Leu Gln Leu Asp Arg Glu Ala
                                                    99
AAC CTC ACC AGC AGC GTG ACG ATA CTG CCA CTG CCT CTG CAG   420
Asn Leu Thr Ser Ser Val Thr Ile Leu Pro Leu Pro Leu Gln
                        *                           113
AAC GCC ACG GTG GAA GCC GGC ACC AGA TGC CAG GTG GCC GGC   462
Asn Ala Thr Val Glu Ala Gly Thr Arg Cys Gln Val Ala Gly
                        *                           127
TGG GGG AGC CAG CGC AGT GGG GGG CGT CTC TCC CGT TTT CCC   504
Trp Gly Ser Gln Arg Ser Gly Gly Arg Leu Ser Arg Phe Pro
                                                    141
ACG TTT GTC AAC GTG ACT GTG ACC CCC GAG GAC CAG TGT CGC   546
Arg Phe Val Asn Val Thr Val Thr Pro Glu Asp Gln Cys Arg
                        *                           155
CCC AAC AAC GTG TGC ACC GGT GTG CTC ACC CGC CGC GGT GGC   588
Pro Asn Asn Val Cys Thr Gly Val Leu Thr Arg Arg Gly Gly
                                                    169
```

FIG.7A

```
ATC TGC AAT GGG GAC GGG GGC ACC CCC CTC GTC TGC GAG GGC   630
Ile Cys Asn Gly Asp Gly Gly Thr Pro Leu Val Cys Glu Gly
                                                      183
CTG GCC CAC GGC GTG GCC TCC TTT TCC CTG GGG CCC TGT GGC   672
Leu Ala His Gly Val Ala Ser Phe Ser Leu Gly Pro Cys Gly
                                                      197
CGA GGC CCT GAC TTC TTC ACC CGA GTG GCG CTC TTC CGA GAC   714
Arg Gly Pro Asp Phe Phe Thr Arg Val Ala Leu Phe Arg Asp
                                                      211
TGG ATC GAT GGT GTT CTC AAC AAC CCG GGA CCG GGG CCA GCC   756
Trp Ile Asp Gly Val Leu Asn Asn Pro Gly Pro Gly Pro Ala
                                                      225
TAG GGGGGCCTGTGACCTCCCATGGAGCCCAGCCCCGCCCTCCACACCTCCGGC   810
End

GCTCCGCACCCACCTCCCACGGCCCCGCCCCTGCCCCCGTCCGGCCAGAGGGGCC   865

CTGGCTGTAATAAAGAAGCCGATCTCTCCTCTGAAAAAAA                  905
```

FIG. 7B

METHOD OF INCREASING MONOCYTE CHEMOTAXIS WITH CAP37 AND MONOCYTE CHEMOTACTIC PORTIONS THEREOF

Some aspects of this invention were made in the course of Grant AI 28018 awarded by the National Institutes of Health and, therefore, the Government has certain rights in some aspects of this invention.

CROSS REFERENCE TO RELATED APPLICATIONS

This application is a continuation of application Ser. No. 07/855,417, filed Mar. 18, 1992, which is a continuation-in-part of application Ser. No. 07/543,151, filed Jun. 25, 1990, now abandoned, which is a continuation-in-part of application Ser. No. 07/375,739, now abandoned, filed Jul. 5, 1989.

FIELD OF THE INVENTION

The present invention relates to methods of making and using novel peptide fragments derived from CAP37, which is an approximately 37,000 dalton cationic granule protein normally synthesized by human polymorphonuclear leukocytes. In particular, this invention relates to novel peptides having monocyte chemotactic activity, such as peptides having the amino acid sequences shown in the Sequence Listing as SEQ ID NO:1, SEQ ID NO:2, SEQ ID NO:3, SEQ ID NO:4, SEQ ID NO:5, and SEQ ID NO:6 and novel peptides having antibiotic activity or lipopolysaccharide-binding activity, such as peptides having the amino acid sequences shown in the Sequence Listing as SEQ ID NO:7 and SEQ ID NO:8.

Throughout this application, various publications are referenced. Full citations for these publications may be found at the end of the specification immediately preceding the claims. The disclosures of these publications in their entireties are hereby incorporated by reference into this application in order to more fully describe the state of the art to which this invention pertains.

BACKGROUND OF THE INVENTION

In the process of inflammation an initial wave of inflammatory cells, comprised primarily of polymorphonuclear leukocytes (PMN) is soon followed by a second wave of cells, which are predominantly monocytes (Hurley et al.; Wilkinson et al.). Although it is widely held that monocytes arrive at an area of inflammation as a result of chemotaxis (Hayashi et al.), the specific mediator(s) responsible for the recruitment of monocytes has remained unresolved.

Monocytes are derived from pro-monocytes, found in bone marrow. The pro-monocytes differentiate into monocytes which are released into the blood. The monocytes circulate in the blood until they are attracted to the site of injury by the inflammation process. Once monocytes enter into tissue they mature into macrophages, also referred to as mononuclear phagocytes. Macrophages are able to engulf and destroy foreign antigens; accordingly, macrophages play an important role in the body's immunological defense system. The term "monocyte" as used herein refers collectively to both circulating monocytes and to macrophages present in tissue.

The preferential migration of monocytes during the latter phase of inflammation indicates the requirement for highly cell-specific chemoattractant, which has little or no effect on the migration of PMNs. Experiments indicate that a granule-associated cationic protein (mol. wt. 37,000 daltons) from human PMN acts as a monocyte-specific chemoattractant. This protein has been previously referred to in the liter attire as CAP37, cationic antimicrobial protein of mol. wt. 37,000 daltons. CAP37 protein has been previously shown to (i) bind bacterial lipopolysaccharides with a high degree of specificity and affinity, and (ii) possess antimicrobial activity against a number of Gram negative bacteria, such as *Salmonella typhimurium* and *Escherichia coli* (Shafer et al., 1986). Thus, CAP37 may play three important functional roles in host defense.

While use of purified CAP37 has far reaching and important functions involving the cellular progression of inflammation, antimicrobial and antineoplastic defenses of the host, the activity of CAP37 as isolated from human PMNs may be limited because of (1) the very small quantities that can be purified and (2) the potential hazards of using human blood products. Use of recombinant CAP37 may overcome some of these problems, but CAP37 is still a large molecule. However, synthetic peptide fragments derived from CAP37 that possess chemotactic, antimicrobial or LPS binding activity and are considerably smaller (e.g., about 25 amino acids in length; approx. 2500–3000 daltons) would overcome these problems. That is, these fragments would be conveniently sized, capable of being produced in unlimited quantities and possess a non-infectious nature.

The instant specification discloses a conventional method for purifying CAP37 to homogeneity and a method for making CAP37 using recombinant DNA techniques. The characterization of the cDNA encoding human CAP37 protein is disclosed. The instant specification has also advanced the art into unchartered areas by disclosing proteins and peptides related and/or derived from CAP37 that have monocyte chemotactic activity, antibiotic activity or lipopolysaccharide (LPS) binding activity. These proteins and peptides can either be synthesized or produced using recombinant DNA techniques. Finally, the instant specification discloses methods for treating diseases and wounds using CAP37 and its related proteins and peptides as well as antibodies to CAP37 and proteins and peptides derived from CAP37 and methods of using these antibodies.

SUMMARY OF THE INVENTION

An object of the present invention is to provide a recombinant DNA molecule encoding a cationic granule protein having the amino acid sequence shown in the Sequence Listing as SEQ ID NO:9. This protein is a potent chemoattractant for monocytes, is bactericidal and is capable of binding bacterial lipopolysaccharide.

The invention further includes DNA molecules encoding amino terminal extensions of the cationic granule protein such as, (a) the amino acid sequence shown in the Sequence Listing as SEQ ID NO:10 (Met Thr Arg Leu Thr Val Leu Ala Leu Leu Ala Gly Leu Leu Ala Ser Ser Arg Ala Gly Ser Set Pro Leu Leu Asp), and (b) Met. The invention also includes DNA molecules encoding carboxy terminal extensions such as Gly Pro Ala.

Another important object of the present invention is to provide a recombinant method of producing the cationic granule proteins encoded by the above described sequences. These proteins include the above described amino terminal extensions as well as other modifications, such as the attachment, to the amino or the carbon terminus of the sequence, of a second protein coding sequence. One example of such a second protein coding sequence is the ricin A chain. Other examples include abrin A chain and trichosanthin. One method of recombinant production is the expression of the cationic granule protein coding sequence fused to the glutathione-S-transferase protein (Sj26) with an in-frame thrombin cleavage site separating the two coding sequences. The fusion protein is then isolated by affinity chromatography for the Sj26 protein portion of the fusion protein, and the cationic granule protein is liberated from the fusion protein by digestion of the fusion protein with the thrombin proteinase.

It is an object of this invention to identify the domains responsible for the antibacterial, chemotactic and LPS-binding activities of the 222 amino acid mature CAP37 protein (SEQ ID NO:9) as extracted from human neutrophils. Thus, it is an object of the present invention to provide bioactive peptides having at least 5 continuous amino acids derived from the above described sequence. These bioactive peptides are either chemotactic for monocytes, able to bind bacterial lipopolysaccharide and/or possess antibacterial qualities. The present invention further provides a recombinant process for the production of the bioactive peptides.

Additionally, it is an object of this invention to provide bioactive peptides (such as chemotactic, antibacterial and/or LPS-binding) derived from CAP37 that are capable of being produced in unlimited quantities and possess a non-infectious nature. Particularly advantageous are those bioactive peptides comprising the peptides shown in the Sequence Listing as SEQ ID NO:1, SEQ ID NO:3, SEQ ID NO:5, and SEQ ID NO:7 and those peptides comprising the peptides shown in the Sequence Listing as SEQ ID NO:2, SEQ ID NO:4, SEQ ID NO:6 and SEQ ID NO:8.

Another object of this invention is to provide bioactive peptides derived from CAP37 that possess enhanced bactericidal activity with respect to the mature CAP37 protein against both gram negative and gram positive bacteria.

Another object of the present invention is to provide expression vectors containing DNA sequences encoding any of the above protein or peptide sequences. These vectors are useful for introducing the coding sequences into suitable hosts. The expression vectors are effective to express the recombinant proteins in a variety of hosts, for example, bacteria, yeast, and mammalian cells. One vector useful for expression of the above described cationic granule protein contains a cytomegalo virus promoter and a polyadenylation signal from SV40, in addition to the dihydrofolate reductase gene to facilitate selection of the vector in the transformed host.

The invention further includes a method of treating a wound by the application of a topical medication containing a cationic granule protein (CAP37) having the amino acid sequence shown in the Sequence Listing as SEQ ID NO:9, or proteins and/or peptides derived from CAP37 that are chemotactic for monocytes or possess antibacterial activity, in the medication in a pharmacologically effective amount to promote wound healing and/or treat infection. Other additions to the medication may be desirable such as the inclusion of epidermal growth factor also present in a pharmacologically effective amount to promote wound healing. The topical medication may take any number of standard forms such as pastes, gels, creams, and ointments. Additionally, the invention includes methods of treating tumors and other diseases using CAP37 and its related proteins and peptides.

It is an object of this invention to treat infection, especially infection caused by gram negative bacteria, by administration of an effective amount of a peptide derived from CAP37 having bactericidal activity superior to that of the mature CAP37 protein, most preferably by administration of the peptide defined in the Sequence Listing by SEQ ID NO:8.

Further, this invention provides for a method of treating endotoxemia or a prophylaclic treatment, such as before surgery, for endotoxemia consisting of administration of an effective amount of the CAP37 mature protein or a peptide derived from CAP37 having LPS-binding activity.

The invention also includes hybrid proteins containing the cationic granule protein having the amino acid sequence shown in the Sequence Listing as SEQ ID NO:9 covalently attached to a second protein molecule, such as an antibody, ricin A chain, abrin A chain or trichosanthin.

These and other features of the invention will become more fully apparent widen the following detailed description of the invention is read in conjunction with the accompanying examples.

BRIEF DESCRIPTION OF THE DRAWINGS

FIG. 1 shows the sequences of peptide fragments derived from the mature CAP37 protein as relevant to the Examples.

FIG. 4 shows a comparison of the N-terminal amino acid sequence of the CAP37 protein with several inflammatory cell proteases.

FIG. 6 shows the nucleic acid and protein sequences of the first isolated cDNA insert having homology to CAP37 protein.

FIG. 7 shows the nucleic acid and protein sequences of the 6a.1 clone insert.

DETAILED DESCRIPTION OF THE INVENTION

I. PURIFICATION AND CHARACTERIZATION OF THE HUMAN CAP37 PROTEIN

Figure 2:
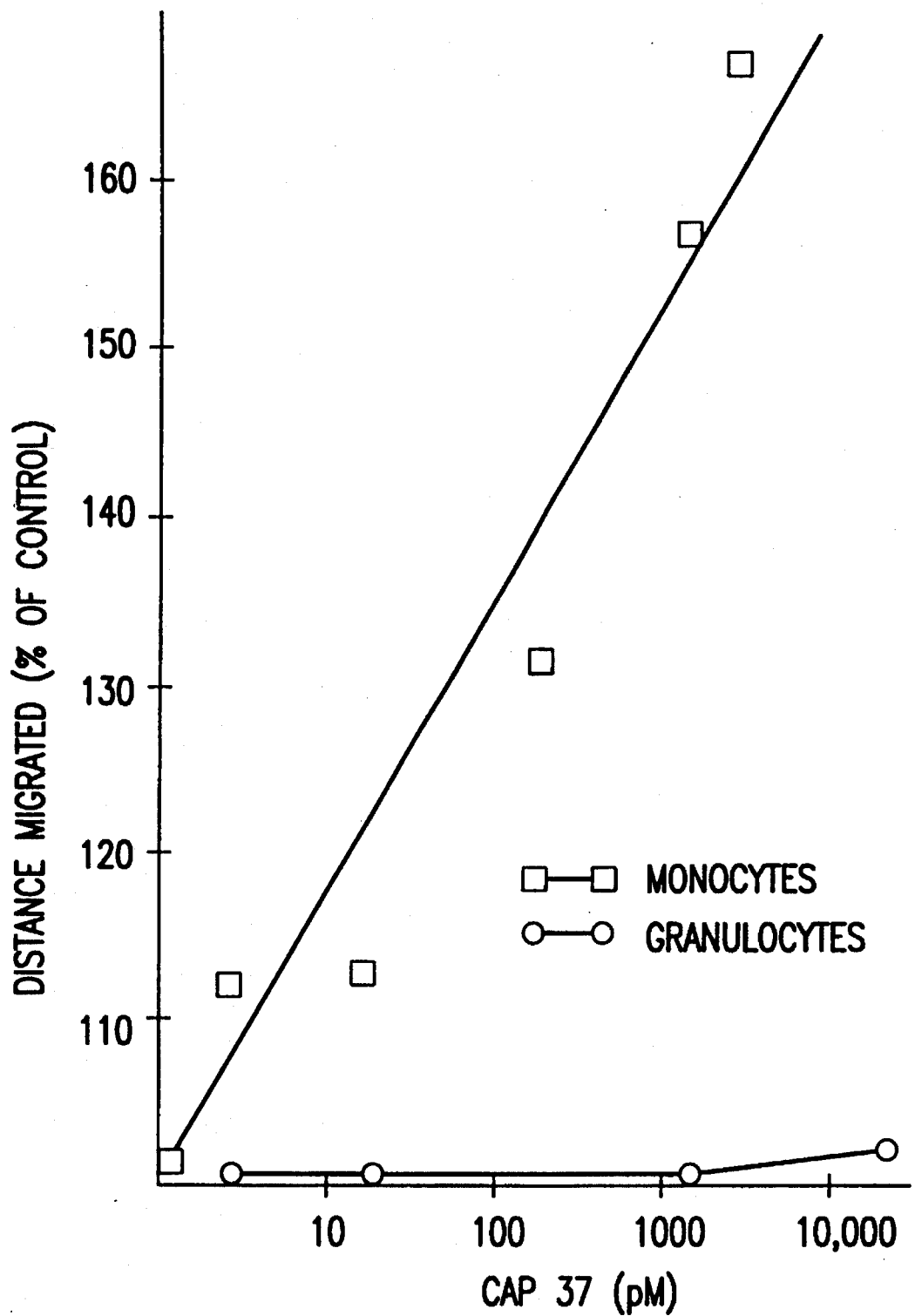
FIG. 2 shows a plot of the data which demonstrates the chemotactic properties of the CAP37 protein.

A. Purification and Sequencing of CAP37 Protein.

CAP37 protein was purified from polymorphonuclear leukocytes (PMN) obtained from healthy adult donors (Example 1-A). The crude preparation generated from PMNs was dialyzed and applied to an ion exchange column. The eluent containing the CAP37 protein came off of the column at NaCl concentrations in the range of 0.6 to 0.7M, as judged by SDS-PAGE or the fractions. This eluent was dialyzed and concentrated. The concentrated preparation was size fractionated and the fractions analyzed by SDS-PAGE to determine the fractions containing the CAP37 protein (Example 1).

Ascites fluid containing antibodies against CAP37 protein was prepared by injecting mice with alum-adsorbed CAP37 protein emulsified in Freund's complete and Freund's incomplete adjuvant (Example 1-C). The specificity of the ascites fluid reactivity against the CAP37 protein was demonstrated in ELISA assays using CAP37, CAP57 (a cationic antimicrobial protein of mol. wt. 57,000 Da; Spitznagel et al.), lactoferrin, myeloperoxidase, cathepsin G and lysozyme as the antigens.

Immunocytochemical analysis of normal human PMN using the monospecific polyvalent mouse antiserum to CAP37 established that CAP37 was a component of the cytoplasmic granules of human PMNs. All other peripheral blood cells which included eosinophils, monocytes, lymphocytes and red blood cells, did not stain positive for CAP37. Immunocytochemical analysis also demonstrated the presence of CAP37 in normal bone marrow, in cells belonging to the myeloid lineage, and in peripheral blood PMN from patients with chronic myelogenous leukemia (CML).

For chemotactic assays, the CAP37 protein was further purified by fractionation of the preparation using hydrophobic high performance liquid chromatography (HPLC). For amino acid sequence determination, a final desalting step was added utilizing reverse-phase HPLC (Example 1).

The N-terminal amino acid sequence of the CAP37 protein was determined by standard microsequencing procedures (Example 1-D). FIG. 1 (Example 1) shows the peptide fragment sequences which were determined for part of the mature CAP37 protein. The first 42 amino acids at the amino terminus of CAP37 have received accession number A33070 from the Biomedical Research Foundation, Georgetown University Medical Center, Washington, D.C. 20007.

B. Chemotactic and LPS-binding Properties of CAP37 Protein

Chemotaxis assays were performed using the modified Boyden chamber technique (Example 2). The results (FIG. 2) demonstrated that CAP37 was obviously chemotactic for human monocytes in the range of 10 to 10,000 pM. CAP37 appeared to be as effective as FMLP in attracting monocytes. These experiments suggest CAP37 did not have any effect on PMN and lymphocyte chemotaxis.

In addition to the observed chemotactic effect on human monocytes, CAP37 at a higher concentration of 1000 ng/ml ($2.7 \times 10^{-8}$M) was chemotactic for rabbit monocytes as well. This may reflect either (i) a reduction in the numbers of receptors for CAP37 on rabbit monocytes as compared to the number of receptors on human monocytes, or, (ii) a difference in the $K_a$ values for the two species. The effect was selective for monocytes since, rabbit PMN did not show a chemotactic response towards CAP37.

One of the important aspects of identification of a chemotaxin is to distinguish directed cell movement (chemotaxis) through the filters as opposed to merely accelerated random motion (clemokinesis). Using the checkerboard assay (Example 2) it was demonstrated that, in addition to its chemotactic properties, CAP37 protein also has some chemokinetic effect on monocytes.

Figure 3:
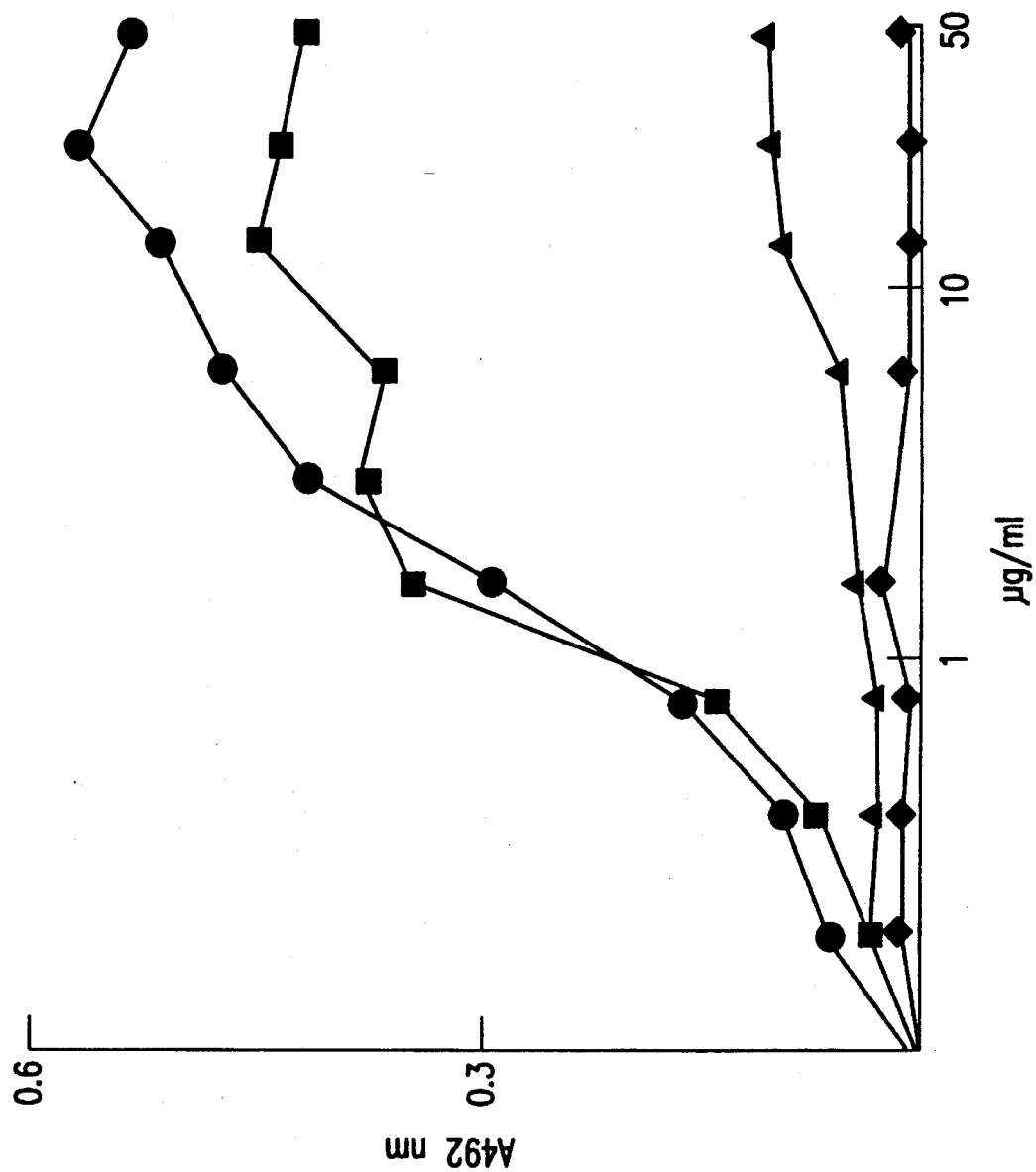
FIG. 3 shows the results of an ELISA showing binding of CAP37 to LPS and Lipid A.

LPS-binding activity of the mature CAP37 protein was determined by measuring the LPS neutralization by CAP37 as determined by the Limulus Amebocyte Lysate (LAL) assay. CAP37 significantly neutralized LPS activity in the LAL assay. Further, ELISA shows binding of CAP37 to LPS; CAP37 is capable of binding LPS and, in particular, Lipid A (FIG. 3).

C. Protein Sequence Comparisons with the Amino Terminus of the CAP37 Protein.

Using the amino terminal sequence of the CAP37 protein, a homology search was conducted of known protein sequences. This search revealed substantial homologies with the amino termini of a subset of serine proteases which mediate a number of functions involved in the inflammatory response (FIG. 4).

Most of the serine proteases with which CAP37 protein shares its greatest homology (elastase, cathepsin G, rat mast cell proteases I and II, H Factor and cytotoxic T cell specific protein I) are derived from the granules of peripheral blood cells. Further, these homologous proteins are known to play important roles in inflammations, such as cytolysis or degradation of extracellular matrices.

Two other serine proteases, bovine thrombin (Bing et al.) and a trypsin-like protease in guinea pig plasma (Kawaguchi et al.), have been described which exhibit chemotactic activity. Further, Wright et al. have described the presence of a factor(s) in PMN specific granules which acts on serum to produce chemotactically active C5a and the opsonin C3b.

The experiments performed in support of the present invention show the isolation, characterization and purification to homogeneity of a PMN-granule associated protein which has monocyte specific chemotactic activity. Further, the CAP37 protein possesses LPS-binding activity as well as bactericidal activity and thus may perform three very important functional roles in vivo.

Example 1

Purification and sequencing of human CAP37 protein

A. Source and Preparation of Peripheral Blood PMN and Monocytes

Blood was collected into sterile sodium-EDTA tubes by venepuncture from healthy adult donors. The polymorphonuclear leukocytes (PMN) were separated from mononuclear cells essentially by the ficoll hypaque density gradient technique of Boyum, followed by dextran sedimentation (T500, Pharmacia 3% in saline) and hypotonic lysis of contaminating red blood cells (RBC).

The mononuclear cell band was further purified to separate the monocytes from the lymphocytes. The mononuclear cells were washed once in phosphate buffered saline (PBS: 0.01M $Na_2HPO_4$, containing 0.15M NaCl, pH 7.4) and resuspended in PBS to a total volume of 5.1 ml. This cell suspension was then added to 6.7 ml of SEPRACELL-MN reagent (a colloidal, silica-based medium having a density of 1.099 g/ml, and available from Sepratech Corporation, Oklahoma City, Okla.), and centrifuged (1500 g for 20 min at 22° C.). The cells were washed twice in PBS (150×g, 15 min) and resuspended in Geys buffered saline (Gibco) containing 2% bovine serum albumin (BSA-Fraction V, endotoxin free, Boehringer Mannhelm Biochemicals) at a final concentration of $2 \times 10^6$ cells/ml. (Geys buffer has the following composition: $CaCl_2$(anhyd.) 0.17 g/L; KCl 0.37 g/L; $KH_2PO_4$ 0.03 g/L; $MgCl_2 \cdot 6H_2O$ 0.21 g/L; $MgSO_4 \cdot 7H_2O$ 0.07 g/L; NaCl 7 g/L; $NaHCO_3$ 2.27 g/L; $Na_2HPO_4 \cdot 7H_2O$ 0.226 g/L; D-Glucose 1.00 g/L.) The monocytes were greater than 95% pure as determined by Wright's and non-specific esterase staining.

Peripheral blood mononuclear cells from adult female rabbits, were separated on a 61% PERCOLL (Pharmacia) gradient (Chambers et al.). This technique separated the mononuclear cells from the RBC and PMNs. No further separation of monocytes from lymphocytes was undertaken with the rabbit blood.

B. Purification of CAP37

A granulocyte concentrate (>95% PMN) was obtained by leukophoresis from a normal human donor. The PMN were disrupted by homogenization in a Potter-Elvehjem tissue grinder (Kontes) for 60 sec at 4° C. Mixed (specific and azurophil) granules were harvested by differential centrifugation. The supernatant obtained by centrifuging at 126×g for 15 minutes was further centrifuged at 20,000×g for 20 minutes to yield a pellet of mixed granules which was extracted at 4° C. with 0.2M sodium acetate (pH 4.0). Granule debris was collected by high-speed centrifugation at 20,000×g for 30 min. The protein concentration was determined by the method of Bradford with chick egg white lysozyme as the standard (Bradford et al., 1976).

The crude granule extract was dialyzed against 50 mM sodium acetate (pH=5) and 0.15M NaCl at 4° C. overnight. The dialysate was then applied to a carboxymethyl SEPHADEX ion exchange column (a weakly acidic cation exchanger having sodium as a counter-ion and carboxymethyl as a functional group, and available from Pharmacia, Piscataway N.J.) which had been equilibrated with 50 mM sodium acetate (pH=5) and 0.15M NaCl. The column was extensively washed with 6M urea in 0.05M sodium acetate (pH5) containing 1.5M sodium chloride. Protein bound to the column was eluted using a two-step linear salt gradient consisting of 0.15 to 0.4M and 0.4 to 1.0M NaCl in 50 mM sodium acetate pH=5. Protein elution was monitored by measuring the absorbance of the eluent at 280 nm. Salt concentrations of the fractions were determined by conductivity measurements. Fractions from the CMS column were tested by ELISA using antiserum to CAP37 to determine those fractions which contained CAP37.

The positive fractions were pooled and dialyzed overnight against 0.2M sodium acetate (pH=4) at 4° C., concentrated by membrane ultrafiltration at 4° C. using a YM-5 membrane filter (an ultrafiltration membrane having very low non-specific protein binding properties, a nominal molecular weight cut-off of 5000 daltons, a clean water flow rate of 0.07–0.1 ml/min/cm² and available from Amicon Corp., Lexington, Ky.). The concentrated preparation was applied to a SEPHADEX G-75 SF (Pharmacia) column (0.5 by 50 cm) which had been equilibrated with 0.2M sodium acetate (pH=4). (SEPHADEX G-75 is a chromatographic medium comprised of a bead-formed gel prepared by cross-linking dextran with epichlorohydrin; said medium having a dry bead size of 10–40μ, bed volume of 12–15 ml/g of dry SEPHADEX, and fractionation range for globular proteins and peptides of 3,000–70,000 daltons.) Fractions were eluted using the equilibration buffer and the $A_{210}$ of each fraction determined. The fractions were analyzed by ELISA and by SDS-PAGE to determine the fraction containing the CAP37 protein.

The CAP37-enriched fraction obtained from the molecular sieve column was further processed using hydrophobic high performance liquid chromatography (HPLC) (BIO-GEL TSK phenyl 5PW column, 7.5 mm×0.75 mm, packed with a 10 micron macroporous support having 1,000 angstrom pores and containing a low density of phenyl groups which promote strong but nondenaturing hydrothobic interactions with proteins, said column available from Biorad Laboratories). The proteins were eluted using a 60 min linear gradient from 1.7M to 0M $(NH_4)_2SO_4$, which contained 0.1M sodium phosphate pH 7.0. The recovery was determined by the optical density of the proteins at 210 nm. The fractions obtained from the hydrophobic HPLC column were pooled independently and the $(NH_4)_2SO_4$ removed by dialysis employing a stirred cell concentrator (YM-5 membrane, Amicon) with 0.2M sodium acetate buffer, pH=4.0.

The purity of the fractions was determined by SDS-PAGE, western blot analysis and ELISA. All these results confirm that CAP37 prepared in this manner is devoid of other contaminating granule proteins which include the defensins, cathepsin G, myeloperoxidase, lactoferrin, and CAP57, and thus indicates that the outlined method yields a highly purified preparation of CAP37.

An important aspect of the production of CAP37 was to keep it free from endotoxin contamination. All reagents and buffers were prepared using pyrogen-free water and tested for endotoxin contamination using the Limulus amoebocyte assay (Whittaker Products). All glassware used was pyrogen-free. The starting material for each column was always checked for endotoxin contamination before it was applied to the column and, most importantly, the final product was always checked for the presence of endotoxin before use.

Figure 10:
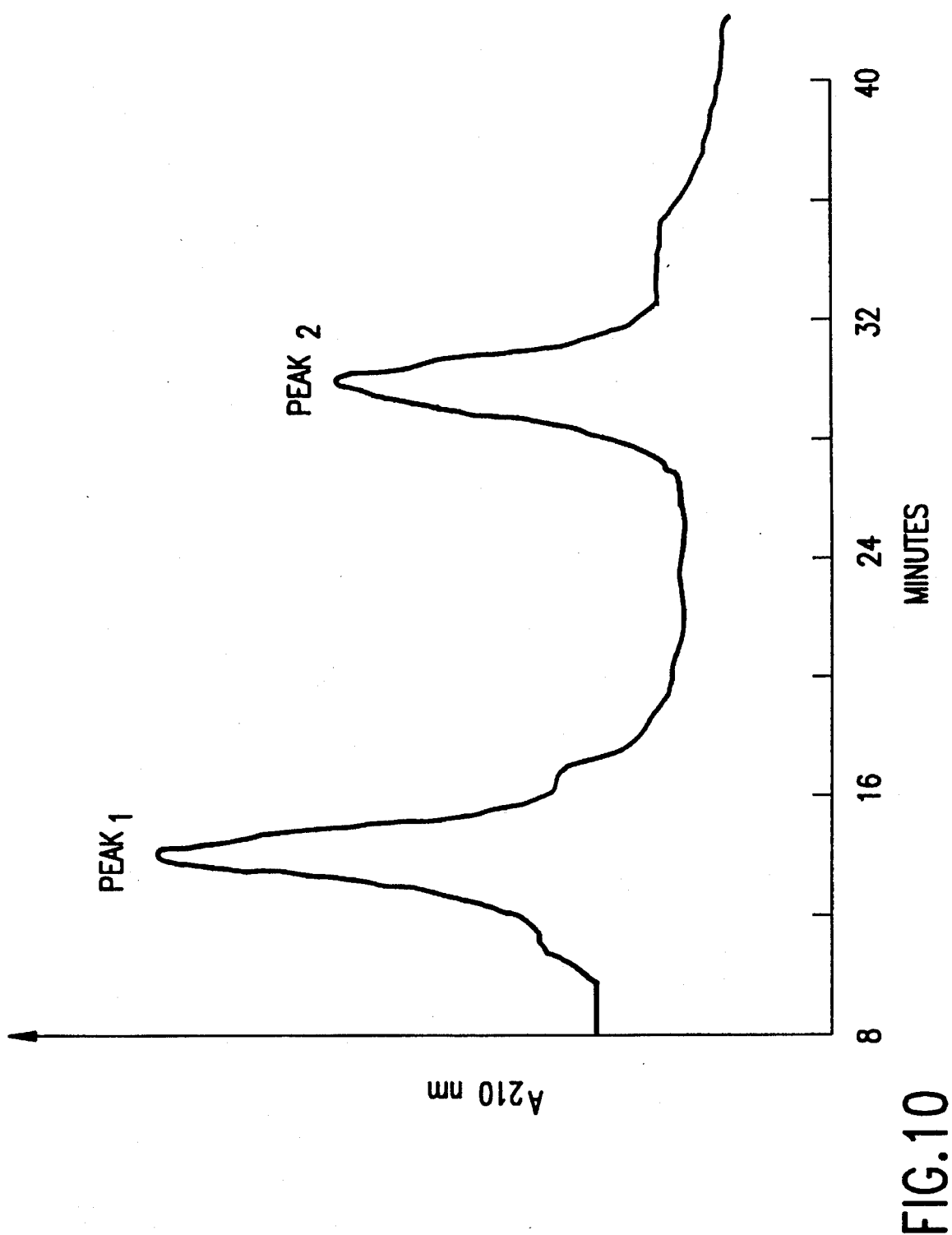
FIG. 10 depicts the elution profile of the eluates from the hydrophobic HPLC of the impure product obtained after separation on a SEPHADEX G-75 chromatographic column.

As seen in FIG. 10, the elution profile from the hydrophobic HPLC column indicated the presence of two proteins. CAP37 was confined to Peak 2, the more hydrophobic peak. Peak 1 was found to contain cathepsin G, as judged by SDS-PAGE.

SDS-PAGE was performed to depict the stages of purification of CAP37 from normal human crude granule extract (CGE). The analysis was performed according to the method described by Laemmli (1970). The samples were solubilized in 0.625M Tris (pH=6.8), 4% (w/v) SDS, and 1% (v/v) beta mercapto ethanol, at 100° C. for 5 min and analyzed on a 12.5% gel essentially according to the method of Laemmli. The analysis was performed under reducing conditions with a 12.5% separating gel and a 4% stacking gel as described by Laemmli. The ratio of the acrylamide to the bisacrylamide was 37.5. Electrophoresis was carried out until the bromophenol blue dye reached the bottom of the separating gel. The gel was removed and fixed in a 25% isopropanol, 7% acetic acid mixture. The gel was oxidized and stained with silver to visualize the protein bands.

The gel was silver stained according to well established protocols. Lane 1 contained 2 μg "rainbow" molecular weight markers (Amersham). Lane 2 contained 5 μg of crude granule extract (CGE). Lane 3 contained 400 ng of peak C material obtained from the G-75 column which served as the starting material for the HPLC column. Lane 4 contained 350 ng of peak 2 (CAP37) from the HPLC column. Lane 5 contained 350 ng of peak 1 from the HPLC column and lane 6 contained purified cathepsin G. The molecular weight standards used included myosin ($M_r$ 200,000), phophorylase b ($M_r$ 92,500), bovine serum albumin ($M_r$ 69,000), ovalbumin ($M_r$ 46,000), carbonic anhydrase ($M_r$ 30,000), trypsin inhibitor ($M_r$ 21,500) and lysozyme ($M_r$ 14,300).

The CAP37 material from peak 2 (lane 4) migrated in SDS-PAGE as three extremely closely spaced bands with a molecular weight near 37,000 daltons. This electrophoretic behavior probably indicates glycosylation of the protein, rather than any heterogeneity of the protein preparation. Furthermore, the fact that this preparation yielded an unambiguous amino acid sequence would also tend to indicate the absence of heterogeneity.

Judging from the nearly identical migration patterns of peak 1 from the HPLC Column (lane 6) and cathepsin G (lane 5), it may be concluded that this peak 1 material is cathepsin G. This was confirmed by the western blots.

The factions obtained from the HPLC column were also analyzed by western blots. Western blot analysis was carried out according to the method of Towbin et al. (1979) with some modifications. Following electrophoresis on a 12.5% SDS-PAGE gel, the proteins were transferred onto a nitrocellulose membrane (Biorad, Richmond, Calif.) in a TE series, Transphor Electrophoresis Unit (Hoerer Scientific Instruments, Calif.) under constant current (200 mA) at 11° C. for 1.5 hr. The concentration of the methanol in the buffer was reduced from 20% to 5% (v/v) and the pH raised to 9. The protein was detected on the nitrocellulose membrane using a mouse antibody to CAP37 (1:100 dilution) and an alkaline phosphatase immunoblotting system with the addition system of 10 units per ml heparin sulfate buffer (Eastman, Kodak) (Spitznagel et al., (1987)) in the wash buffer (0.15M NaCl, 0.01M Tris HCl (pH 7.5), 0.01% v/v TWEEN 20). Color development was obtained with the nitroblue tetrazolium/BCIP system.

The results of the western blot confirmed the SDS-PAGE results. Lane 1 contained molecular weight markers as described for the SDS-PAGE. Lanes 2 and 6 contained crude granule extract. Lanes 3 and 7 contained peak C material from the G-75 column. Lanes 4 and 8 contained peak 2 from the HPLC column and lanes 5 and 9 contained peak 1 from the HPLC column. The protein concentrations of all the samples loaded onto the gel were the same as described above.

Lanes 1 to 5 were probed with goat anti-human cathepsin G (1:2000 dilution) and lanes 6 to 9 were probed with mouse anti-human CAP37 (1:100 dilution). The second antibody was conjugated to alkaline phosphatase (1:7500 dilution, Promega). Color development was obtained using the nitroblue tetrazolium/BCIP system as outlined in the manufacturers handbook (Promega). The goat anti-human cathepsin G antiserum reacted with crude granule extract, peak C material and peak 1 from the HPLC column. It did not react with CAP37 (peak 2 material from the HPLC column). On the other hand, the antiserum to CAP37 reacted with peak 2 material but not with the cathepsin G. This indicates that CAP37 was totally separated from the contaminating cathepsin G in the final step of the purification which is performed on the hydrophobic HPLC column.

The proteins obtained from the HPLC column were further analyzed by ELISA which confirmed the purity of the CAP37 preparation. The ELISA method used is described in Pereira, et al., (1989), and has proven to be a reproducible and sensitive method for the detection of cationic proteins. Briefly, the protein was attached to a 96 well microtiter plate (NUNC Immunoplate I, VWR Scientific) which was pro-treated with poly-L-lysine. Following an overnight incubation at 4° C., the plate containing the antigen was washed four times in phosphate buffered saline (pH 7.4). Non-specific sites on the plate were then blocked with a heparin containing phosphate buffer, at room temperature for 1 hr (Pereira et al., 1989). The plates were washed and the primary antibody was then added to the plate and incubated for 1 hr at 37° C. Following this incubation the plate was washed and the second antibody was added and the plate incubated for 1 hr at 37° C. The second antibody was a goat anti-mouse immunoglobulin which is conjugated to horse-radish peroxidase. The color development step involves incubating the substrate (3.7 mM 0-phenylenediamine) in citrate phosphate buffer, pH 5.0, containing 0.24 µl/ml 30% $H_2O_2$ at room temperature for 30 min. The reaction is stopped with 2.5M $H_2SO_4$ and the absorbance read immediately using a TITERTEK multiscan plate reader (Flow Laboratories) at 492 nm.

The results of the ELISA confirmed the results of the other analyses. The same samples as used for the SDS-PAGE were also used in the ELISA. Primary antibodies were prepared against each of these samples. The material from Peak 2 reacted only with the antibodies prepared against a pure CAP37, while the material from Peak 1 reacted with the antibody prepared against Cathepsin G. The crude granule extract reacted with all the antibodies and the Peak C material reacted with antibodies for CAP37 and for Cathepsin G.

For amino acid sequencing of the CAP37 protein a final desalting step using reverse phase HPLC was employed. A DYNAMAX 300A C8 column was equilibrated with 0.1% Trifluoroacetic acid in water the above-purified material was then applied to the column. Elution of the purified protein was effected by a 30 minute elution with a 0–80% gradient of 0.1% Trifluoroacetic acid in acetonitrile at a flow rate of 1 ml per minute. The CAP37 protein containing sample corresponded to the 16.14 minute peak, as determined by SDS-PAGE: this fraction was concentrated in a Savant Instruments SPEED VAC.

C. Antibodies to Purified CAP37 Protein

Ascites fluid containing antibodies against CAP37 protein was prepared by injecting BALB/c mice (Jackson Laboratories) with 250 ng of alum-adsorbed (Herbert) CAP37 protein emulsified in an equal volume of Freund's complete and Freund's incomplete adjuvant (Difco Laboratories). Mice were subcutaneously injected with a total volume of 200 µl of the above suspension. The mice were boosted three weeks later with 250 ng of alum-adsorbed CAP37 injected intraperitoneally. At the same time the mice were injected with 1 ml of pristane (2,6,10,14-tetramethyl pentadecane, Sigma). One week later $10^7$ SP2/0 mouse myeloma cells were injected intraperitoneally (Lacy et al.). Ascites fluid was collected. The specificity of the ascites fluid reactivity against the CAP37 protein was demonstrated in ELISA assays (Pereira et al.) using CAP37, CAP57 (a cationic antimicrobial protein of mol. wt. 57,000 Da; Spitznagel et al.), lactoferrin, myeloperoxidase, cathepsin G and lysozyme as the antigens. Further, no cross reactivity between Cathepsin G and CAP37 protein was observed by western blot analysis (Ausubel et al.).

For the immunocytochemical studies, the final cell concentrate was adjusted to $1 \times 10^6$ nucleated cells per ml in 10% heat inactivated fetal bovine serum (Hyclone Laboratories Inc., Utah) in PBS. One hundred microliters of the cell suspension was cytocentrifuged onto glass slides. The cells were fixed in buffered formol acetone, pH 7.2 at 4° C. for 60 seconds. The staining was performed using the VECTASTAIN Avidin Biotin Complex-Glucose oxidase (ABC-G0) technique (Vectastain Laboratories, Burlingame, Calif.) as described previously (Spitznagel et al.). The above described monospecific polyvalent mouse anti CAP37 ascites fluid (1:100) was used to stain the cells. Color development was obtained using the nitroblue tetrazolium salt (VECYASTAIN GO substrate kit I) at room temperature for 30 minutes. Normal mouse serum and phosphate buffered saline (PBS) served as the negative controls. Ascites fluid made against myeloperoxidase, a known marker of the primary granule of PMNs, served as the positive control.

D. Microsequencing of CAP37

The protein sequence analysis of CAP37 was performed using an Applied Biosystems Model 477A Protein/Peptide Sequencer with an on-line Applied Biosystems 120A PTH-Amino Acid Analyzer. Reagents and solvents were from Applied Biosystems, Foster City, Calif. Phenylthiohydantoin (PTH)-derivatized amino acids formed sequentially by Edman degradation were separated using an Applied Biosystems PTH C-18 HPLC reverse phase microbore column (2.1 mm ID×220 mm) by gradient elution. The sample was applied to an acid-etched glass-fiber filter which had been treated with 3 mg Biobrene (polybrene) and precycled. Peak identification and yield quantitation was based on a standard PTH-amino acid profile. The N-terminal end of the CAP37 protein was identified by standard microsequencing procedures (Applied Biosystems). Trypsin and chymotrypsin generated digestion fragments of CAP37, were separated and purified using hydrophobic and reverse-phase HPLC (Example 1-B). These fragments were then sequenced, as described above. When the cloning of the cDNA was undertaken only the sequences shown in FIG. 1 had been determined. The sequences of the amino and carboxy termini of the mature CAP37 protein are designated in FIG. 1.

Example 2

Chemotactic and LPS-binding Properties of the Purified Human CAP37

A. In Vitro Chemotaxis Assays

Chemotaxis was measured using the modified Boyden chamber technique (Snyderman et al.). The leading front method (Zigmond et al.) was used to assess migration of monocytes and lymphocytes through a 8 μm filter (Millipore Corporation, Bedford, Mass.). PMN chemotaxis was measured using a 3 μm filter (Millipore). The purified CAP37 protein (Example 1) used in chemotaxis assays were endotoxin-free as determined by the Limulus Amoebocyte Lysate Assay (Whittaker Bioproducts, Inc., Walkersville, Md.). The dilutions of CAP37 and N-formyl-methionyl-leucyl-phenylalanine (FMLP) were made in Geys buffer (Gibco) containing 2% endotoxin-free bovine serum albumin (BSA). Geys buffer containing 2% BSA served as the negative control, and a $10^{-1}$M solution of FMLP as the positive control.

The chambers were incubated in a humidified atmosphere (6.2% $CO_2$) for 2 hours when testing monocytes and lymphocytes, and for 30 minutes when testing PMNs. The filters were then removed and processed as previously described (Snyderman et al.). The cells were viewed using oil immersion and the distance the cells had migrated into the filter was determined over five different fields on the same slide (Zigmond et al.). Triplicate assays were performed for each experimental point.

The results are presented in FIG. 2. The data clearly show the strong chemotactic properties of the CAP37 protein.

CAP37 did not have any effect on PMN and lymphocyte chemotaxis in the range employed in these experiments. In addition to the observed chemotactic effect on human monocytes, CAP37 at a higher concentration of 1000 ng/ml ($2.7\times10^{-8}$M) was chemotactic for rabbit monocytes as well. The effect was selective for monocytes since rabbit PMN did not show a chemotactic response towards CAP37.

To distinguish directed cell movement (chemotaxis) through the filters of a Boyden chamber as opposed to accelerated random cell motion (chemokinesis), the chemokinetic activity of CAP37 was determined by the checkerboard assay of Zigmond et al. The checkerboard assay demonstrated that in addition to its chemotactic properties, CAP37 has some chemokinetic effect on monocytes.

FIG. 3 shows the results of an ELISA procedure used for determining the binding of CAP37 to LPS from S. minnesota wild type (diamonds); LPS from S. minnesota Re mutant (triangles); Lipid A from S. minnesota R595 (circles); and Lipid A from S. typhimurium Re mutant (squares). The LPS from S. minnesota wild type, S. minnesota Re mutant, Lipid A from S. minnesota R595, and Lipid A from S. typhimurium Re mutant were applied to microtiter wells at concentrations ranging from 0 to 50 μg/ml and incubated overnight. The trays were then incubated with CAP37 at 120 ng/well for 1 hour at 37° C. The next incubation was with a rabbit antiserum against CAP37 (1:400 dilution) and the color development was as previously described (Pereira et al., 1989) and the absorbance was read at 492 nm. The results shown in FIG. 3 indicate that CAP37 is capable of binding Re LPS and, in particular, is able to bind to Lipid A better than wild type LPS.

Further, the neutralization of LPS activity, as assayed by the limulus amebocyte lysate (LAL) assay, by CAP37 was measured. CAP37 was diluted to the desired concentrations (from 6.2 ng/ml to 500 ng/ml) in geys buffered saline pH 7 (GIBCO). To this wild type LPS (RIBI IMMUNOCHEM) or Re LPS from Salmonella (David Morrison, Kansas Medical Center) was added so that the final concentrations were 0.1, 0.5, 1.0 and 2.0 ng/ml LPS. The tubes were incubated at 37° C. for between 30 to 60 minutes and then assayed in the chromogenic LAL assay, using polymyxin E as a control. CAP37 significantly neutralized LPS activity in the LAL assay.

B. In Vivo Chemotactic Assay

The purpose of these experiments is to document that CAP37 when injected in vivo into mice will result in the emigration of monocytes/macrophages.

Female BALB/c mice (6–8 weeks) (Jackson Laboratory, Bar Harbor, Mich.) were injected intraperitoneally (i.p.) with 100 ng CAP37 (purified according to the method of the invention) per mouse in 2 ml RPMI-1640 serum-free medium (Mediatech). A control group of mice were injected i.p. with 2 ml brewers thioglycollate (4% w/v) (Difco Laboratories), a known stimulator of inflammatory cells whose action is well documented. A second control group of mice were injected j.p. with 2 ml of RPMI-1640 alone.

(RPMI-1640 serum free medium from Mediatech has the following composition: $CaNO_3.4H_2O$:100.00 mg/L; KCl:400.00 mg/L; $MgSO_4.7H_2O$:100.00 mg/L; NaCl:6000.00 mg/L; $NaHCO_3$:2000.00 mg/L; $Na_2HPO_4.7H_2O$:1512.00 mg/L; D-Glucose:2000.00 mg/L; Glutathione (reduced):1.00 mg/L; Phenol red:5.00 mg/L; L-Arginine(free base):200.00 mg/L; L-Asparagine:50.00 mg/L; L-Aspartic acid:20.00 mg/L; L-Cystine:50.00 mg/L; L-Glutamic acid:20.00 mg/L; L-Glutamine:300.00 mg/L; Glycine:10.00 mg/L; L-Histidine (free base):15.00 mg/L; L-Hydroxyproline:20.00 mg/L; L-Isoleucine (Allo free):50.00 mg/L; L-Leucine (Methionine free):50.00 mg/L; L-Lysine HCl:40.00 mg/L; L-Methionine:15.00 mg/L; L-Phenylalanine:15.00 mg/L; L-Proline (Hydroxy L-Proline free):20.00 mg/L; L-Serine:30.00 mg/L; L-Threonine (Allo free):20.00 mg/L; L-Tryptophan:5.00 mg/L; L-Tyrosine:20.00 mg/L; L-Valine:20.00 mg/L Biotin:0.20 mg/L; D-Ca pantothenate:0.25 mg/L; Choline chloride:3.00 mg/L; Folic acid:1.00 mg/L; i-Inositol:35.00 mg/L; Nicotinamide:1.00 mg/L; Para-aminobenzoic acid:1.00 mg/L; Pyridoxine HCl:1.00 mg/L; Riboflavin:0.20 mg/L; Thiamine HCl:1.00 mg/L; and Vitamin $B_{12}$:0.005 mg/L.)

At 6, 24, 48 and 72 hours following these i.p. injections, four mice in each group were sacrificed by $CO_2$ anesthesia. Ten ml sterile medium was injected into the peritoneal cavity of each mouse and the abdominal area gently massaged to dislodge the exudate cells. The medium containing the exudate cells was then aspirated from the peritoneal cavity using a 19 gauge needle attached to a syringe. The total number of cells in the peritoneal exudate was determined by counting the cells on a COULTER COUNTER (Coulter Electronics, Hialeah, Fla.: The operation of the COULTER COUNTER is based on electrical conductivity difference between particles and common diluent. Particles act as insulators, diluents as good conductors. The particles, suspended in an electrolyte, are forced through a small aperture through which an electrical current path has been established. As each particle displaces electrolyte in the aperture, a pulse essentially proportional to the particle volume is produced. Thus a 3-dimensional particle volume response is the basis for all sizing, regardless of position or orientation of the particle in solution.) One hundred µl of the peritoneal exudate was cytocentrifuged onto a glass slide and the cells stained with Wright's stain. A differential count of the cells was made by counting the number of monocytes, lymphocytes, neutrophils, basophils and eosinopfils per hundred consecutive cells. These experiments were performed to determine the time course of migration of neutrophils, monocytes, lymphocytes and other cells into the peritoneal cavity, in response to an i.p. injection of CAP37.

Traditionally neutrophils are the first cells to migrate into the peritoneal cavity, and they do so about 6 hours after the i.p. injection. Monocytes emigrate much later, generally 72 hours to 6 days after the i.p. injection.

The results, shown in Table 1 below, indicated that an injection of 100 ng of CAP37 into the peritoneal cavity, moderately increased the overall numbers of cells emigrating into the peritoneal cavity. Nevertheless, monocytes appeared in the peritoneal cavity much earlier (24 hours) than when thioglycollate was used. Furthermore, the percentage of monocytes elicited with CAP37 (55%) was much greater than when sodium thioglycollate (33%) was used even at the 72 hour time point. A further interesting observation was the dramatic reduction in neutrophils by 24 hours with the CAP37 injection whereas, with thioglycollate, the neutrophils persist at a very high percentage up to 48 hours (36%), and are still present at 72 hours (21%).

TABLE 1

Migration of cells following intraperitoneal injection with the inflammatory stimulus indicated.

| Inflammatory Stimulus* | Hours Post Injection | Total Cells[b] × 106 | % monocytes | % PMN |
|---|---|---|---|---|
| None | 0 | 3.1 | 18 | 30 |
| RPMI-1640 | 6 | 1.5 | 15 | 42 |
|  | 24 | 2.2 | 12 | 11 |
|  | 48 | 3.1 | 14 | 28 |
|  | 72 | 2.8 | 43 | 5 |
| Thioglycollate | 6 | 9.5 | 4 | 65 |
|  | 24 | 9.1 | 5 | 77 |
|  | 48 | 8.4 | 20 | 36 |
|  | 72 | 11.1 | 33 | 21 |
| CAP 37 | 6 | 3.6 | 7 | 65 |
|  | 24 | 3.8 | 27 | 26 |
|  | 48 | 3.5 | 48 | 4 |
|  | 72 | 3.3 | 55 | 3 |

[a]Four mice per group
[b]Mean value for each group of four mice

These responses with CAP37 contrasted markedly with responses to endotoxin in which far greater cell numbers are found to endotoxin in which far greater cell numbers are found and PMN persist as the predominant cell type for at least 48 hours (Snyderman et al, (1971)). The migration of monocytes into the peritoneal cavity following CAP37 injection into the peritoneal cavity of mice demonstrates the potent monocyte chemoattractant capacity of CAP37 in this in vivo animal model.

Example 3

Comparison of the CAP37 protein amino terminal sequence

Using the first 45 amino acids of the amino terminal end of the CAP37 protein, a search of a protein sequence data base was made using the FASTAMAIL program through the BIONET network. This search revealed substantial homologies with the amino termini of a subset of serine proteases which mediate a number of functions involved in the inflammation response (see FIG. 4: elastase, ELAST; complement factor D, FACTD; bovine plasminogen, PLASM; cathepsin G, CATG; rat mast cell protease I and II, RMCPI and RMCPII; cytotoxic T cell I, CCPI; cytotoxic T cell protease—H Factor, HF).

The closest over-all homologies were obtained with two PMN-derived granular proteins: a homology of 57.5% with human elastase (Sinha et al.) also known as medullasin (Okano et al.) and a homology of 45% with human cathepsin G (Salvesen et al.). Other specific homologous sequences were seen with bovine plasminogen (45%) and human complement factor D (45.5%) (Johnson et al.; Nieman et al. et al.), which is the first enzyme involved in the activation of the alternative complement pathway.

Two other groups of proteins which demonstrated strong homology with the CAP37 protein were: (a) the group of serine protease-like molecules derived from granules of atypical rat mast cells—rat mast cell protease I (Woodbury et al.), RMCPI, 38.6%, and rat mast cell protease II, RMCPII, 40% (Benfey et al.); and (b) two proteins from cytotoxic T cells—cytotoxic T cell protease I (Lobe et al.), CCPI, 40%, and cytotoxic T cell protease factor H (Gershenfeld et al.), HF, 38.6

II. CLONING OF THE CAP37 PROTEIN CODING SEQUENCE: ISOLATION OF A FIRST cDNA HAVING HOMOLOGY TO CAP37 PROTEIN.

For the isolation of the CAP37 cDNA coding sequence, poly-A mRNA was isolated from tumor cell line HL60 (Example 4-A,B). Using the CAP37 protein specific antibodies generated in Example 1, the HL60 cell line was shown to contain antigens which reacted with this antibody. Double-stranded (ds) cDNA was generated from the isolated RNA molecules (Example 4-C,D). These ds molecules were cloned into the vector lambda-gt10 (Example 4-E).

Plaques resulting from recombinant phage were transferred to duplicate filters and the filters hybridized with two CAP37 sequence specific probes (Example 4-E). The probes were non-coding strand 20-mer degenerative sets generated from the known amino terminal protein sequence of CAP37 protein (FIG. 1, Example 1) based on the use of preferred human codons (Maruyama et al.). The filters where then probed with each probe set. The duplicate filters showed one recombinant plaque that was convincingly positive with both probes.

Figure 5:
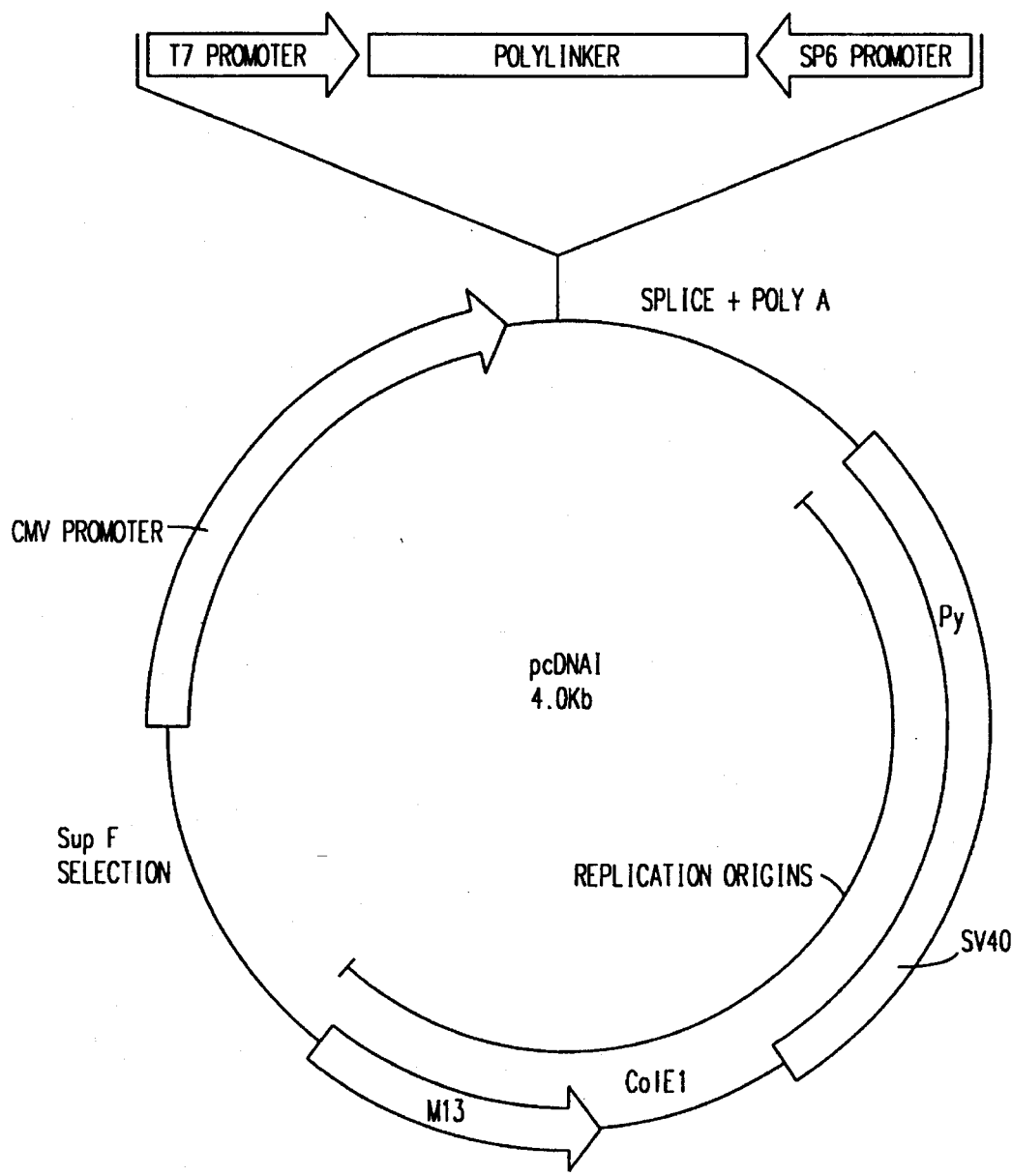
FIG. 5 illustrates the pcDNAI cloning vector used for subcloning inserts from original lambda clones.

The phage was purified from the plaque which tested positive and the double-stranded cDNA insert was isolated from the phage. This insert was then cloned into vector pcDNAI (Example 5, FIG. 5) and the insert sequenced. The complete sequence of this first cDNA clone is shown in FIG. 6.

The nucleic acid sequence of the cDNA was translated into the corresponding protein sequences in all three frames. One of the reading frames showed significant alignment to the CAP37 protein sequence with the following exceptions: (i) the cloned sequences indicate that the encoded protein most likely has a precursor form since the cloned sequences contain an additional 48 amino acids 5' to and in frame with the open reading corresponding to the CAP37 protein sequence (Example 6); (ii) there appeared to be some carboxy terminal differences in protein sequence; and, (iii) 19 amino acids present in a CAP37 protein fragment amino acid sequence were not found in the nucleic acid insert sequence (Example 6). The 19 amino acids missing from the protein encoded by the first cDNA clone suggested that although this clone contained coding sequences for the majority of the CAP37 protein it was not the correct cDNA.

Hybridization of other CAP37 specific probes to the above filters did not result in the identification of any more likely candidate plaques.

In order to clone a cDNA encoding the complete CAP37 protein sequence, the following strategy was employed. A specific DNA fragment, which would span the region where the discrepancy between the cDNA sequence and the protein sequence was observed (Example 6), was amplified (Example 7). One end of this DNA fragment was chosen to correspond to the amino acid sequence CQVAGWG (SEQ ID NO:11) (underlined in the CAP37 peptide sequence presented in Example 6): a degenerate 20-mer oligonucleotide probe (designated Intrlc) was designed to correspond to these amino acids.

The second end of the above discussed DNA fragment was less stringently designated. A number of non-degenerate 20-mer primers were designed from the sequence of the non-coding strand of CAP37 first cDNA which was 3' to the end of the site where the nucleic acid sequence diverged from the protein coding sequence (see * in the CAP37 first cDNA sequence in Example 6).

Total human genomic DNA was used as template in DNA amplification reactions utilizing the above described primers (Example 7). The products of the amplification reactions were split into two samples, fractionated on an agarose gel and then one-half of the gel containing a complete set of samples was transferred to a nitrocellulose filter. The filter was then probed with the radioactively-labeled CAP37 first cDNA: one positive band was detected. The DNA was extracted from the region of the second half of the agarose gel corresponding to the positive band. This DNA fragment (Intrlc/669 nc) was then sequenced (Example 7-A).

A 50-mer probe corresponding to a region of the Intrlc/669 nc sequence which was not present in the CAP37 first cDNA clone was synthesized. This probe was then used to screen 200,000 plaques generated from the lambda-HL60 cDNA library (Example 7-B). After a secondary screen 5 plaques remained clearly positive. One of these clones, designated 6a.1, was sequenced using dideoxy sequencing. The complete DNA sequence of the 6a.1clone is illustrated in FIG. 7.

The DNA sequence corresponding to clone 6a.1 was translated in all three reading frames. One reading frame aligned with the amino acid sequences of the CAP37 peptide fragments determined in Example 1. The CAP37 mature protein coding sequence was preceded, in frame, by 26 amino acids, and had a short carboxy terminal extension. These results indicate that the 6a.1 clone is a complete cDNA clone encoding the CAP37 protein.

Figure 8:
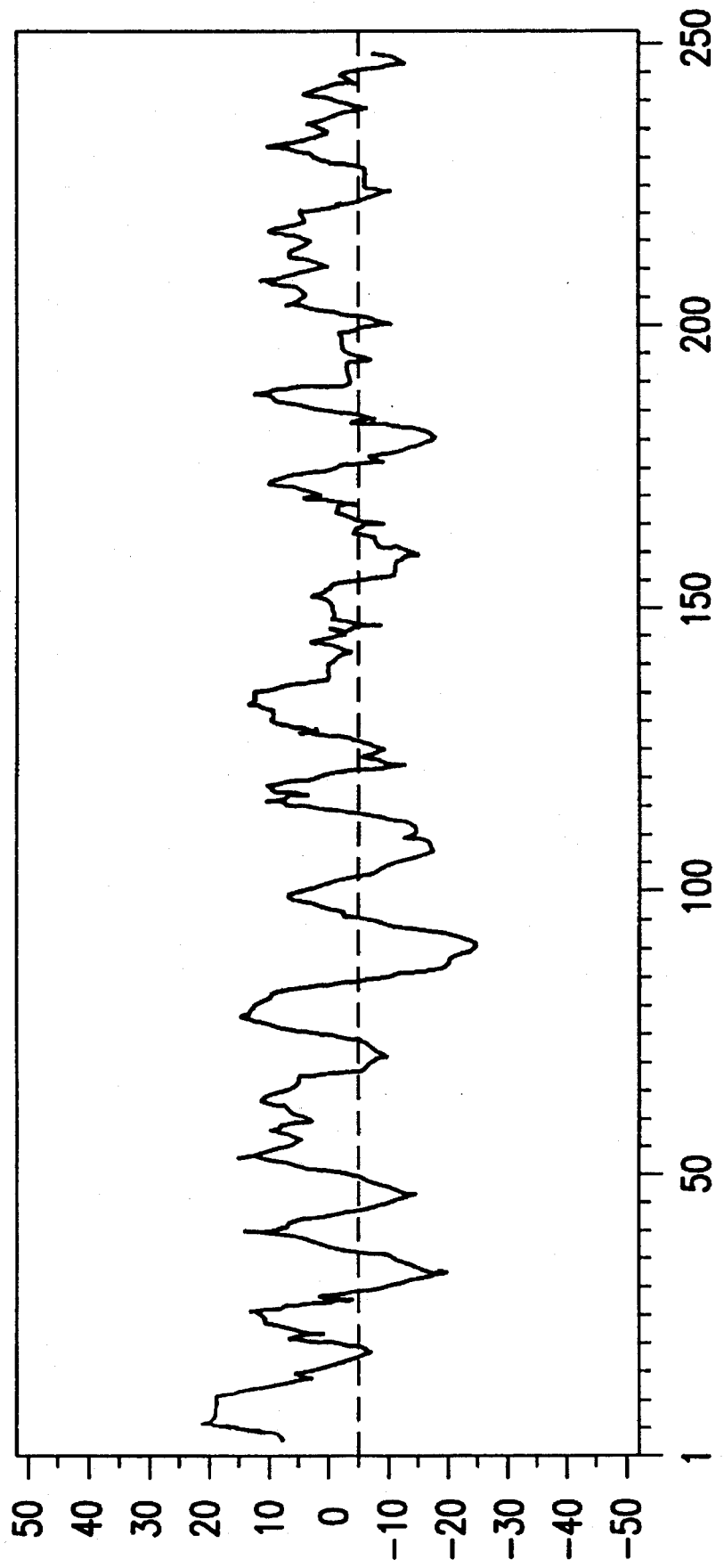
FIG. 8 shows a hydropathy index computation for the entire coding sequence of the CAP37 protein including: the amino-terminal extension and the sequence encoding the mature protein.

The first approximately 20 amino acids of the cDNA encoded CAP37 protein have a high degree of hydrophobicity (FIG. 8). This sequence has the length and hydrophobicity of a typical eucaryotic secretory signal sequence (Example 8). The remaining amino acids in this 26 amino acid sequence and/or the carboxy-terminal extension may be involved in further cellular processing of the CAP37 protein or they may represent an inactive precursor form of the protein.

The portion of the open reading frame corresponding to the mature form of the CAP37 protein has an estimated molecular weight of 24,276 kilodaltons. Previously Shafer et al. (1986) determined the molecular weight of the CAP37 protein to be approximately 37,000 daltons. This discrepancy is most likely the result of post-translational modification, e.g. glycosylation, of the CAP37 protein.

Subsequent to the isolation and sequencing of the 6a.1 cDNA insert, the complete protein sequence of the mature CAP37 protein was determined. With the exception of the above described amino and carboxy terminal extensions, the coding sequence of the mature CAP37 protein exactly aligns with the protein sequence encoded by the 6a.1 insert.

Example 4

Isolation of a First cDNA having Homology to Human CAP37 Protein

A. Preparation of poly-A mRNA

The starting material for the isolation of human CAP37-encoding cDNA was tumor cell line HL60 (ATCC CCL240). Using the anti-CAP37 specific antibodies that were described above, the presence of an antigen reacting with these antibodies was shown to be present in the HL60 cell line: this cell line was chosen as the starting material for cloning a CAP37 encoding cDNA. All of the following procedures were carried out on ice and with RNase-free materials.

Monolayers of HL60 were grown to confluence using standard sera-supplemented minimal media (DMEM/10% Fetal Calf Serum, 50 units/ml penicillin and 50 µg/ml streptomycin) in 85 mm plates. Cells were grown to a density of $10^6$ cells/ml. Each plate was placed on ice and washed four times with ice-cold phosphate buffered saline (PBS) and a final 2 ml aliquot of PBS added to each plate. The cells were harvested from each plate by scraping, transferred by pipette to COREX centrifuge tubes, and held on ice. When all the plates were harvested the cells were pelleted by centrifugation at 2000×g for 5 minutes at 4° C.

RNA was isolated frown 10⁸ cells by the previously described method of Chirgwin et al. using guanidine isothiocyanate.

B. Selecting the poly(A) enriched mRNA fraction.

Oligo(dT) cellulose (0.1–1.0 g; purchased from Pharmacia) was suspended in 1–5 ml of elution buffer (distilled H₂O, 1 mM EDTA), poured into a 1- to 4-ml disposable column, and washed with 5 column volumes of binding buffer (0.01M Tris-HCl at pH 7.5, 0.5M NaCl, 1 mM EDTA, 0.5% SDS). The isolated RNA was resuspended at 1–5 mg/ml in elution buffer, heated to 65° C. for 5 min, quickly cooled in ice, diluted with an equal volume of 2× binding buffer, and applied to the column: the flow-through was collected and reapplied to the column. The column was washed with 5–10 volumes of binding buffer and 5 volumes of wash buffer (0.01M Tris-HCl at pH 7.5, 0.1M NaCl, 1 mM EDTA).

The bound RNA was eluted with 2–3 column volumes of elution buffer; subsequently, it is adjusted to a final concentration of 0.5M NaCl (with 5M NaCl or 2× binding buffer), re-bound, re-washed, and re-eluted as described above. The RNA in the final eluate was recovered by addition of 0.1 volumes or 3M sodium acetate and precipitation with 2.5 volumes of ethanol. Sodium dodecyl sulfate (SDS) is deliberately excluded from the wash and elution buffers to avoid precipitating the detergent from ethanol along with the RNA.

The final RNA sample was precipitated and dissolved in sterile water to a final RNA concentration of approximately 1 μg/μl C. First-Strand cDNA Synthesis Double-stranded (ds) cDNA was synthesized using the Amersham cDNA synthesis kit. Briefly. 5 μg of mRNA was added to the following reaction mixture: first strand synthesis reaction buffer, sodium pyrophosphate solution, human placental ribonuclease inhibitor (HPRI, 50 units), deoxynucleotide triphosphate mix (1 mM dATP, 1 mM dGTP, 1 mM dTTP, and 0.5 mMdCTP), 4 μg oligo-dT, 100 units reverse transcriptase, and 5 μCi (α-³²P)-dCTP in a total volume of 50 μl. The reaction was incubated at 42° C. for 60 minutes.

D. Second-Strand cDNA Synthesis

A final volume (250 μl) containing the first strand synthesis mix was mixed with *E. coli* ribonuclease (4 units) and *E. coli* DNA polymerase I (115 units). This mixture was incubated at 12° C. for 60 minutes, 22° C. for 60 minutes, and 70° C. for 10 minutes. T₄ DNA polymerase (10 units) was added and the sample incubated at 37° C. for 10 minutes. The ds cDNA was phenol/chloroform extracted, chloroform extracted, and ethanol precipitated (Maniatis et al.).

E. Cloning of the Double Stranded cDNA.

For ease of manipulation the double stranded cDNA was tailed with EcoRI linkers in the following manner.

The cDNA was resuspended in water and treated with EcoRI methylase under the following conditions: 100 mM Tris HCl, pH=8.0; 10 mM EDTA; 80 μM S-adenosylmethionine; 100 μg/ml bovine serum albumin; with approximately 100 units of EcoRI methylase (Promega) in a total volume of 50 μl incubated at 37° C. for 60 minutes. The cDNA was then precipitated with ethanol.

The cDNA was resuspended in 5 μl of dH₂O to which was added 2 μl of 10× ligase buffer (0.5M Tris HCl, pH=7.4; 70 mM MgCl₂; 10 and 1 μl t4 DNA ligase (100 units). The mixture was incubated at 16° C. overnight. The reaction mixture was extracted once with phenol/chloroform and the cDNA precipitated with ethanol. The cDNA was then digested with EcoRI in a buffer containing 100 mM Tris-HCl (pH 7.5), 50 mM NaCl and EcoRI restriction enzyme (50 units) was incubated at 37° C. for 3 hours. The ds cDNA was extracted, precipitated, resuspended, and separated from the EcoRI linkers using a Sephacryl S-400 column.

Finally, the cDNA was size fractionated as follows before insertion into the vector. The cDNA was resuspended in the following buffer: 0.6M NaCl, 20 mM Tris HCl (pH=8.0), and 20 mM EDTA. This sample was then loaded on a SEPHACRYL S-400 column which was equilibrated with the same buffer. Fifty microliter aliquots were then collected and assayed by electrophoresis through an alkaline agarose gel to identify the fractions containing labelled cDNA molecules of greater than 400 base pairs (bp) in length. These >400 bp fractions were then pooled and the cDNA precipitated with ethanol.

The vector for insertion of the >400 bp cDNA molecules was EcoRI digested and phosphatased λgt10 (Stratagene). A Stratagene Gigapack Gold Packaging Extract Kit was used to package the Lambda gt10/cDNA ligation mixture. A primary titer of 1×10⁷ PFU's was obtained.

Plaques resulting from recombinant phage, carrying the cDNA, were then picked to fresh lawns of C600. Nitrecellulose filters (Schlcicher and Schuell) were then presoaked in a cell suspension of C600Hfl (a less permissive host strain) and dried. The coated nitrecellulose filters were then layered onto the phage-containing agar plates to transfer phage particles to the filters. Duplicate filters were prepared.

When the bacterial law had grown and plaques were apparent the filters were then employed in in situ hybridization after the method of Woo. A primary screen of 500,000 clones at 50,000 PFU/plate was performed using duplicate filters. Briefly, the filters were lifted from the plates and placed on WHATMAN 3 MM filters saturated with 0.5M NaOH and 1.5M NaCl to lyse the bacteria and phage particles. The filters were neutralized by successive transfer to WHATMAN filters saturated with, first, 0.5M Tris HCl, pH=7.4, with 1.5M NaCl, and, second with 2× SSC (Maniatis et al.). The nitrocellulose filters were then blotted dry, air dried, and baked under vacuum at 68° C. for 2 hours.

The filters were prehybridized with 1× PAM containing 30% formamide. (A 1 liter solution of 2× PAM contained: 200 ml 50× Denhardts; 500 ml 20× SSC; 100 ml 1M NaH2PO4, pH=7.0; 20 ml 100 mM PPI; 100 mM Na2HPO4; 100 μg/ml sonicated salmon sperm DNA; and, 120 mg ATP.) The prehybridization solution was removed. The hybridization was performed overnight, at 42° C., in a solution of 1× PAM containing 30% formamide and a labeled probe set.

Two sets of probes were used to screen the duplicate filters. These probes were two sets or short oligonucleotides made to the amino-terminus of the CAP37 protein (FIG. 1) as follows:

Oligo 1 (Cap37a-1), non-coding strand, amino acids 18–24, (SEQ ID NO:12): 5'-C(GT)GCCTCC(TC)TG(AG)T-T(CT)TG(AG)AT-3'; and Oligo 2 (Cap37a-2), non-coding strand, amino acids 9–15, (SEQ ID NO:13): 5'-A(GA)GAAGGG(AG)AA(CT)TG-(CATG)C(GT)GGG-3'.

Bases presented in parenthesis are alternative insertions at that site.

The two sets of probes were 5' end-labelled using [λ-³²P] ATP and T₄ Polynucleotide kinase (Bethesda Research Laboratories, 5'DNA Terminus Labelling System). Each set of duplicate filters were hybridized, as described above, with one of the probe sets. The filters were then washed as follows: 2×SSC wash at 4° C. (2×15 minutes) followed by a 3M (CH3)₄NCl wash at 53° C. (2×15 minutes). The filters were then dried and subjected to radioautograhy at −20° C. using intensifying screens. The duplicate filters showed one recombinant plaque that was convincingly positive with both probes.

coding region is shown in FIG. 6.

Example 6

Characteristics of the First cDNA

The first cDNA sequence was translated into its corresponding amino acid (aa) sequence. A continuous open reading frame exits from nucleotide 176 to 856. This sequence was then aligned to the peptide fragments determined from microsequencing of the purified CAP37 protein (FIG. 1). A DNA sequence encoding a protein sequence corresponding to the amino terminus of the mature CAP37 protein sequence begins at nucleotide 320. The cDNA encodes a protein in which the first amino acid of the mature protein is preceded by an in-frame open reading frame corresponding to an additional 48 amino acids. Further, the carboxy terminus of the cDNA encoded protein contained an extension, Gly Pro Ala, not present in the mature protein.

In matching the translated cDNA to the protein sequences in FIG. 1 a problem was encountered in the cDNA sequence. The sequence of interest in CAP37 first cDNA is as follows (SEQ ID NO:14 and SEQ ID NO:15):

```
ATG CTG CTT CAG AGG TTT GTC AAC GTG ACT GTG ACC CCC GAG GAC
 M   L   L   Q * R   F   V   N   V   T   V   T   P   E   D
CAG TGT CGC CCC ACC ACC GTG TGC ACC GGT GTG CTC ACC CGC CGC
 Q   C   R   P   T   T   V   C   T   G   V   L   T   R   R
GGT GGC ATC TCG AAT GGG GAC GGG GGC ACC CCC CTC GTC TGC GAG
 G   G   I   S   N   G   D   G   G   T   P   L   V   C   E
CCG CTG GCC CAC GGC.
 P   L   A   H   G
```

This sequence corresponds in part to PE-V10, an internal peptide of the CAP37 protein (amino and carboxy termini were identified, see FIG. 1 ). A partial sequence of the PE-V10 peptide follows here (SEQ ID NO:16):

Ala Gly Thr Arg <u>Cys Gln Val Ala Gly Trp Gly</u> Ser Gln Arg Ser Gly
GlyArgLeuSerArgPhePro*ArgPheValAsnValThrValThr
ProGluAspGlnCysArg.

Example 5

Analysis of the First cDNA insert in Lambda gt10

The restriction map of the cloned cDNA was determined; no internal EcoRI sites were detected in the sequence. The approximately 850 bp insert was removed from the λgt10 vector by digestion with EcoRI; the corresponding DNA fragment was resolved and subsequently isolated from a polyacrylamide gel (Maniatis et al.). This EcoRI fragment was then cloned into the unique EcoRI site of the vector pcDNAI (FIG. 5; Invitrogen, San Diego, Calif.).

The vector pcDNAI has a Col E1 origin of replication derived from pBR322, the CMV promoter sequences and a polyadenylation signal available for expression in mammalian cells (such as COS7), and a poly-linker flanked by opposing T₇ and SP6 promoters providing for ease of expression of inserted DNA sequences in bacteria. The vector is also useful for DNA sequencing in that region of the poly-linker provides for the use of a universal primer homologous to the T₇ and SP6 promoters.

The region containing the CAP37 coding region was sequenced by standard double-strand sequencing methods (Pharmacia Sequencing Kit, Pharmacia), starting with the universal sequence primer discussed above, as well as unique synthetic oligonucleotide primers derived from the CAP37 coding sequence as they were needed. The sequence of the first cDNA clone having homology to the CAP37

The 19 amino acids preceding the asterisk in the BE-V10 sequence were not represented in the first cDNA: the point of divergence in the cDNA sequence is also marked by an asterisk. Accordingly, while the first cDNA apparently coded for the majority of the CAP37 protein, it was not the correct cDNA.

The mature C-terminal sequence of the CAP37 protein (peptide PE-T19) indicates that there is also a carboxy terminal extension present in the cDNA CAP37 protein coding sequence which is not present in the mature protein.

Example 7

Isolation of a Second cDNA having Homology to Human CAP37 Protein
A. Amplification of a fragment spanning the region of discrepancy between the cDNA sequence and the protein sequence.

As a first step to clone a cDNA containing the complete CAP37 coding sequence, an attempt was made to amplify a specific DNA fragment which would span the region where the discrepancy between the cDNA sequence and the protein sequence was observed. A degenerate oligonucleotide probe corresponding to the amino acids CQVAGWG (SEQ ID NO:11) (underlined in the CAP37 peptide sequence presented in Example 6) was synthesized. The oligonucleotide was a 20 mer (256 fold degenerate, designated Intrlc), synthesized as follows (SEQ ID NO:17):
5'TG(CT)CA(AG)GT(ACTG)GC(ACTG)GG(ACT-G)TGGGG 3',
where the bases in parenthesis are alternative substitutions at that site.

As a second primer for use in DNA amplification a number of 20 mer primers were designed from the sequence of the non-coding strand of CAP37 first cDNA.

Total human genomic DNA was used as template in DNA amplification reactions (Mullis; Scharf et al.) involving the above described primers. The amplification reactions were divided into two samples and each set of samples were fractionated on an agarose gel. The samples in one half of the gel (representing a complete set of amplification reactions) were transferred to nitrocellulose (Maniatis et al.). The nitrocellulose filter was hybridized (Maniatis et al.) with radiolabelled CAP37 first cDNA (Bethesda Research Laboratories Nick Translation Kit) as a probe.

The Southern blot hybridization showed one positive band. This band was generated using primer Intrlc (above) and a non-coding strand 20 mer designated 669 nc (corresponding to base pairs 652–671 of CAP37 first cDNA, FIG. 6). The region of the second half of the agarose gel corresponding to the positive band was excised and the DNA extracted, phenol/chloroform extracted, and precipitated (Ausubel et al.). The band was then sequenced using the Intrlc/669 nc primers (Pharmacia Sequencing Kit, Pharmacia).

The sequence of Intrlc/669 nc generated band was as follows (SEQ ID NO: 18 and SEQ ID NO:19):

Example 8

Characteristics of the 6a.1 cDNA Encoded Protein

The 6a.1 cDNA sequence was translated into its corresponding amino acid (aa) sequence. A continuous open reading frame exists from nucleotide 4 to 756. This sequence was then aligned to the peptide fragment sequences obtained from microsequencing of the purified CAP37 protein (Example 1). The corresponding DNA coding sequence begins at nucleotide 82. All of the protein sequences determined by microsequencing of the purified CAP37 protein had corresponding protein sequences in the 6a.1 cDNA encoded protein.

The 6a.1 cDNA encodes a protein in which the first amino acid of the coding sequence of the marlite protein is preceded by an in-frame open reading frame corresponding to an additional 26 amino acids: these 26 amino acids do not correspond to those seen in the first cDNA protein. The first approximately 20 amino acids of this region have a high degree of hydrophobicity (FIG. 8). The length of the sequence and the degree of hydrophobicity make this sequence an ideal candidate for a eucaryotic secretory signal sequence. The hydropathy index plot was generated using the SOAP program of PCGENE (Intelligenetics, Mountain View, Calif.). The SOAP program uses the method of Kyte et al to plot the hydropathicity of the protein along its sequence. The interval used the computation was 11 amino acids.

The cDNA encoded protein apparently has a carboxy terminal extension relative to the mature CAP37 protein, i.e. Gly Pro Ala.

The portion of the open reading frame corresponding to

```
TGTAG GTT GCG GGT TGG GGG AGC CAG CAC AGT GGG GGG CGT CTC TCC CGT
      V   A   G   W   G   S   Q   H   S   G   G   R   L   S   R

TTT CCC AGG TTC GTC AAC GTG ACT GTG ACC CCC GAG GAC CAG TGT CGC CCC
F   P   R   F   V   N   V   T   V   T   P   E   D   Q   C   R   P

AAC AAC GTG TGC ACC GGT GTG CTC.
N   N   V   C   T   G   V   L
```

B. Second Screening of the lambda gt10/HL-60 cDNA library for a CAP37 cDNA.

A 50 mer corresponding to a region of the Intrlc/669 nc sequence which was not present in the CAP37 first cDNA clone was synthesized and used as a probe to screen 200,000 clones at 50,000 PFU/plate (as in Example 4).

The sequence of the oligonucleotide probe was as follows (SEQ ID NO:20):
5'     TGTCAGGTTGCGGGTTGGGGGAGCCAG-CACAGTGGGGGGCGTCTCTCCCG 3'.

On an initial screen 11 positives were identified of which 5 remained positive following a secondary screen. The EcoRI cDNA fragment of one of these clones, designated 6a.1, was subcloned into the pcDNAI vector and sequenced using dideoxy sequencing: the 6a.1 insert subclone in pcD-NAI was designated pcDNA-CAP#2. The complete DNA sequence of the 6a.1 clone is illustrated in FIG. 7. The plasmid pcDNA-CAP#2 has been deposited under the terms of the Budapest Treaty with the American Type Culture Collection (12301 Parklawn Dr., Rockville Md. 20852 U.S.A.) and given accession number ATCC 68340.

the mature from of the protein has an estimated molecular weight of 24,276 daltons. The moleculing weight previously determined for the CAP38 protein, i.e. approximately 37,000 daltons (Sharer et al., 1986), was obtained from SDS-PAGE of the purified protein. The discrepancy in molecular weight is most likely the result of post-translational modification of the CAP37 protein. For example, the CAP37 sequence has three potential N-glycosylation sites, as determined by PROSITE analysis (PCGENE lntelligenetics, Mountain View, Calif.) of the 6a.1 cDNA coding sequence. These potential glycosylation sites are located at asparagine residues 100, 114, and 145 of the mature sequence.

Using the method of Hopp et al. (ANTIGEN program, PCGENE Intelligenetics, Mountain View, Calif.), the primary antigenic determinants of the CAP37 protein sequence were determined. The three highest points of hydrophilicity are from residues 61 to 66, 5 to 10, and 150 to 156 of the mature protein sequence, with the highest average hydrophilicity value being for residues 61–66.

III. RECOMBINANT EXPRESSION OF THE CAP37 PROTEIN

Factors that are involved in successful expression of a cloned gene in a particular system include, solubility within the cell, non-toxicity to the cell, possible secretion by the expressing cell, low levels of proteolytic digestion by the cell and ease of purification in the system. Folding, disulfide bond formation, as well as post-translational modifications (glycosylation, phosphorylation, etc.) can affect expression and synthesis of proteins; these factors differ according to the host cells used for expression.

The *E coli* plasmid system to express CAP37 was described by Smith et al. This system involves the use of a plasmid expression vector designed to direct synthesis of foreign polypeptides as fusions with the protein Sj26; Sj26 is a glutathione S-transferase protein from *Schistosoma japonicum*. Purification of the fusion protein is accomplished by affinity chromatography on immobilized glutathione. Smith et al. have described the use of expression vectors encoding a thrombin cleavage site immediately adjacent the carboxy terminus of Sj26 and the amino-terminal of the foreign protein which is to be expressed. Recovery of the foreign protein can be achieved by thrombin digestion of the purified fusion protein (Example 9-A). The thrombin digestion is followed by a final purification step to remove Sj26. High yields of several soluble proteins have been demonstrated with these plasmids.

Alternatively, the thrombin cleavage site can be replaced by another protease cleavage site such as collagenase (EC 3.4.24.3, from *Clostridium histolyticum*) by insertion of an oligonucleotide linker containing the appropriate cleavage sequence (e.g., see Example 10-B).

In addition to the above described vector there are numerous *E. coli* expression vectors known to one of ordinary skill in the art useful for the expression of CAP37 protein. If necessary an amino terminal methionine can be provided the CAP37 protein coding sequence by insertion of a Met codon 5' and in-frame with the CAP37 protein coding sequence. Also, the carboxy-terminal extension of the cDNA encoded CAP37 protein can be removed using standard oligonuclcotide mutagensis procedures.

There are several advantages to yeast expression systems. First, evidence exists that proteins produced in a yeast secretion systems exhibit correct disulfide pairing (Zsebo et al.). Second, post-translational glycosylation is efficiently carried out by yeast secretory systems (Gillis et al.; Thim et al.; Chang et al.; Hoylaerts et al.; Lemontt et al).

The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The CAP37 protein coding sequence is fused in-frame to the pre-pro-alpha-factor leader region (Example 9-B). This construct is then put under the control of a strong transcription promoter, such as the alcohol dehydrogenase I promoter or a glycolytic promoter. The CAP37 protein coding sequence is followed by a translation termination codon which is followed by transcription termination signals. Alternatively, the CAP37 protein coding sequences can be fused to a second protein coding sequence, such as Sj26 (Example 9-A) or β-galactosidase (Example 10-B), used to facilitate purification of the fusion protein by affinity chromatography. The insertion of protease cleavage sites to separate the components of the fusion protein, such as described above for CAP37 protein expression in *E. coli*, is also applicable to constructs used for expression in yeast.

Mammalian cells permit the expression of proteins in an environment that favors important post-translational modifications such as folding and cysteine pairing, addition of complex carbohydrate structures, and secretion of active protein.

Figure 9:
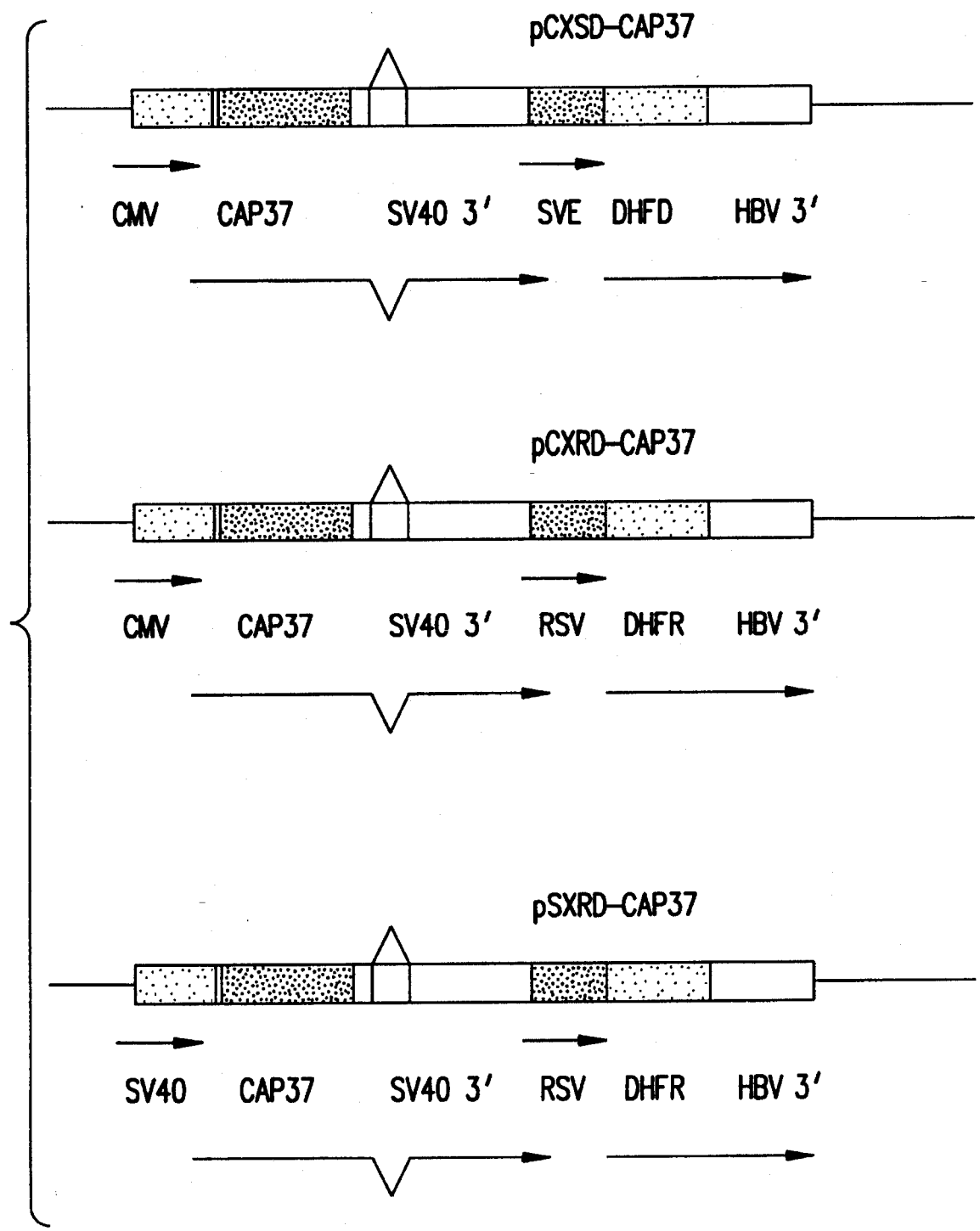
FIG. 9 illustrates the expression vectors used for expression of CAP37 protein in mammalian cells.

Vectors useful for the expression of CAP37 protein in mammalian cells are shown in FIG. 9. These vectors are characterized by insertion of the CAP37 protein coding sequence between a strong vital promoter and a polyadenylation signal. The vectors further contain genes conferring either Gentamicin or methotrexate resistance for use as selectable markers. The CAP37 protein coding sequence has been introduced into a Chinese hamster ovary cell line using a methotrexate resistance-encoding vector (Example 9-C). Presence of the vector DNA in transformed cells has been confirmed by Southern analysis and production of an RNA corresponding to the CAP37 protein coding sequence has been confirmed by Northern analysis.

Alternative vectors for the expression of CAP37 in mammalian cells, are those similar to those developed for the expression of human gamma-interferon, tissue plasminogen activator, clotting Factor VIII, hepatitis B virus surface antigen, protease Nexinl, and eosinophil major basic protein, will be employed (Gray et al; Wood et al.; Patzer et al.; Berman et al.; McGrogan et al, 1988 A and B). Further, the vector shown in FIG. 5 contains CMV promoter sequences and a polyadenylation signal available for expression of inserted DNAs in mammalian cells (such as COS7).

The identification and use in cloning of the entire CAP37 protein coding sequenced identified by cDNA sequencing is particularly useful in mammalian cells since the putative pre-pro sequence (i.e. the first 26 amino acids of the cDNA encoded protein coding sequence) may have important effects on secretion and other protein processing events.

Example 9

Expression of Recombinant CAP37 Protein from the 6a.1 cDNA Coding Sequence

A. Expression of CAP37 in *E. coli*.

The following primers are used for DNA amplification of the CAP37 coding DNA fragment from the CAP37 cDNA clone (Example 7):

5'-ATCGTTGGCGGCCGGAAGGCG-3' (SEQ ID NO:21); and,

5'-TTGGGCCCTGGCCCCGGTCGG-3' (SEQ ID NO:22).

These primers result in the amplification of the CAP37 mature protein coding sequence. If a 5' methionine is required for expression the first primer can be modified to:

5'-ATGATCGTTGGCGGCCGGAAGGCG-3' (SEQ ID NO:23)

to generate amplified fragments encoding a 5' methionine. Primers can also be designed to result in amplification of the precursor form of the CAP37 protein, for example:

5'-ATGGGGGAGGGTGGGTCC-3' (SEQ ID NO:24)

and the same second primer as above. Following confirmation by DNA sequencing, the amplified DNA fragment is blunt-end ligated (Maniatis et al.) in-frame into a plasmid expression vector (Smith et al.) designed to direct synthesis of foreign polypeptides as fusions with the protein Sj26; Sj26 is a glutathione S-transferase protein from *Schistosoma japonicum* (Smith et al.). Further, Smith et al. have described an expression vector encoding a thrombin cleavage site immediately adjacent the carboxy terminus of Sj26 at the site where the amino-terminal of the foreign protein is fused. *E. coli* strain JM101 is then transformed (Maniatis et al.) with either (i) the plasmid containing the fusion protein coding sequences, or (ii) the parent plasmid without the CAP37 sequences.

The transformed cells are grown, expression of the desired proteins induced with IPTG (Smith et al.), and the cells grown a further 3–6 hours before harvest. As a control transformed cells are also grown and not induced with IPTG.

The harvested cells are then lysed (Smith et al.). A portion of each lysate is subjected to SDS-PAGE to test for expression of the fusion protein by size comparison to the native Sj26 protein and to protein molecular weight size standards. A band traveling at the molecular weight predicted for the fusion protein is expected from the lysate containing the fusion protein coding sequences, but not from lysates from cells transformed with parent vector alone or from those not induced with IPTG.

The bulk of the fusion-protein-containing lysate is treated with immobilized glutathione to purify the fusion protein (Smith et al.). This purified fusion protein is then subjected to SDS-PAGE to examine the relative purity of the preparation. The purified fusion protein is cleaved with thrombin (Boehringer-Mannheim) and the CAP37 separated from the Sj26 protein by chromatography (e.g., size exclusion chromatography followed by an ion exchange column as in Example 1).

B. Expression of CAP37 in Yeast.

For expression of CAP37 in yeast, pre-pro-alpha-factor/CAP37 gene fusions are constructed. The DNA amplified CAP37 cDNA used above for construction of *E. coli* vectors is also used for construction of yeast vectors. The expression vector contains the yeast alcohol dehydrogenase I transcription promoter and terminator (Oeda et al.). The CAP37 cDNA is blunt-end ligated, in-frame (Maniatis et al.) directly following the Lys-Arg dipeptide sequence of the pre-pro-alpha-factor leader (Kurjan et al.). This expression vector construct directs synthesis, secretion and processing of the hybrid protein in yeast.

In order to maximize protein product yield the expression vector containing the CAP37 cDNA is transformed (Ausubel et al.) into a yeast strain carrying the pep4 mutation (Jones); such strains are defective in four major vacuolar proteases and RNase. The CAP37 protein is purified from the media by a combination of size fractionation followed by ion-exchange chromatography (Example 1). Alternatively, the yeast cells are mechanically lysed (Guarente) and the CAP37 protein isolated from the lysate in the same manner.

C. Expression of CAP37 in Mammalian Cells.

(i) Modification of CAP37 cDNA.

The cDNA clone encoding CAP37 was modified to be bounded by a HindIII restriction site at the 5' end of the sequence and a XbaI site at the 3' end as follows. Two primers for use in DNA amplification reactions were designed to be complementary to the ends of the CAP37 cDNA and contain the desired restriction sites. The sequence of the two primers used to prepare the DNA amplification product were: (SEQ ID NO:25 and SEQ ID NO:26)

The DNA was amplified as per the manufacturers instructions (Cetus-Perkin Elmer, Norwalk Conn.). The resulting 5' end contained a HindIII site followed by the consensus mammalian initiator sequence CCACCATG.

(ii) Construction of Vectors.

The above modified CAP37 cDNA was inserted into a series of expression vectors having the following properties:

1. Unique HindIII and XbaI cloning sites situated between a strong viral promoter (either CMV, SV40, or RSV) and a polyadenylation signal derived from SV40).
2. A selectable marker linked to the vector containing either Gentamicin resistance or methotrexate resistance.

The vectors are shown in FIG. 9.

In FIG. 9, plasmid vector sequences derived from pUC18 are denoted by the thin line. The promoter preceding the CAP37 cDNA insert was joined to the pUC polylinker at the EcoRI site. The cytomegalovirus (CMV) promoter cassette (pCXSD-CAP37 and pCXRD-CAP37) was a 637 bp fragment which contains the promoter and enhancer of the immediate early gene 1 (IE1) of CMV (Seed). The promoter cassette was modified to be bounded by an EcoRI restriction site at the 5' end of the cassette and HindIII and BglII sites at the 3' end of the cassette. The SV40 sequences flanking the 3' end of the CAP37 cDNA insert was composed of two elements from the SV40 early region. A 620 bp Sau3A fragment spanning the T antigen splice signal was joined to the 350 bp BclI-BamHI fragment of SV40 which spanned the polyadenylation signal of the SV40 early gene (Seed). The dihydrofolate reductase (DHFR) cassette was derived from a murine cDNA encoding DHFR and nodified to contain a BglII site preceding the translational start site of the clone and ending at a SalI restriction site situated adjacent to the BglII restriction site of DHFR (Simonsen et al.). The SV40 E promoter cassette, at the 5' end of the DHFR insert in pCXSD-CAP37, was a 540 bp fragment which spanned the SV40 origin of replication, early, and late promoters, and is bounded by an EcoRI (Simonsen et al.). This SV40 promoter cassette can also be used for expression of the CAP37 cDNA (e.g., pSXRD-CAP37). The RSV promoter cassette, at the 5' end of DHFR in pCXRD-CAP37 and pSXRD-CAP37, was derived frown the Rous Sarcoma Virus and spans the LTR, ending at a point 90 base pairs downstream of the transcriptional start site (Seed). The HBV 3' end of the each vector was a 585 bp BamHI-BglII fragment which spanned the HBV surface antigen polyadenylation signal (Simonsen et al.).

(iii) Derivation of Transformed Cell Lines.

Host cell lines which can be transformed using the above described vectors include human, mouse, and hamster. The preferred host cell line is a Chinese Hamster Ovary cell line (CHO) which has been rendered incapable of producing the enzyme dihydrofolate reductase (Urlaub et al.): the expression of CAP37 is not limited to this line. Typically, use of vectors containing a gene encoding dihydrofolate reductase (DHFR) has allowed for the efficient selection of stable cell lines expressing the transfected plasmid. In addition, such cell lines are capable of being selected with the relate analogue methotrexate, resulting in the emergence of cells having amplified copies of the DHFR cDNA and the co-transfected sequences (Simonsen et al.; McIvor et al.; MeGrogan et al., 1988 A).

Plasmid DNA containing the CAP37 protein encoding cDNA and the DHFR-encoding gene was transfected into CHO cells using the cationic liposome method (DOTMA). $2 \times 10^5$ cells were passaged into 5–25 flasks 48 hours prior to

```
5':  5'-CCGGAATTCCAAGCTTCCACCATGACCCGGCTGACAGTCCTGG-3'
          HindIII

3':  5'-CCGGATCCTCTAGACCCTAGGCTGGCCCCGGTCCCGG-3'.
          XbaI
``` the transfection and allowed to grow in non-selective media. Ten ug of plasmid DNA was diluted to 50 ul with sterile distilled water and then added to 25 µg of DOTMA (Lipofectin, Bethesda Research labs) in a volume of 50 ug. The DNA was mixed and allowed to stand 30 minutes at room temperature. Immediately prior to the addition of the DNA to the cells, the T-flasks were washed three times with serum-free media. Three milliliters of serum-free media was added to each T-flask, after which the DOTMA-DNA mixture was added to the cells. The flasks were swirled and returned to the incubator for 4 hours. Three milliliters of fresh media with 20% serum was then added to each flask of cells and the cells allowed to incubate for 48–72 hours at which time the cells were removed by trypsinization, split into 10 cm dishes, and suspended in selective media containing methotrexate.

The cells were returned to the incubator and allowed to grow with twice-weekly changes of media. After 2–3 weeks, colonies become apparent. Cloning cylinders were used to isolate and subclone colonies arising from an individual transfected cell.

Both bulk populations and subclones were expanded for protein assay by Western blot assays (Ausubel et al.). Cell lines expressing CAP37 antigen were selected for amplified CAP37 expression by growing the cells in stepwise increasing levels of methotrexate (MTX). Cell lines resistant to 1 µM MTX were subcloned and characterized by Northern and Southern analysis (Maniatis et al.), doubling time, expression levels and stability of expression.

In addition to the above bacterial, yeast, and mammalian systems there are numerous expression systems, well known to one of ordinary skill in the art, available suited to the expression of CAP37 (e.g., Kingsman et al.; Brake, 1989; Revel et al.; Moriarty et al.; Kopchick et al.).

For all of the above expression systems antibodies generated to the CAP37 protein, or portions thereof, (Examples 1 and 15) can be used to follow and to quantitate the CAP37 produced; the antibodies are particularly useful for following the purification of CAP37 as, for example, described above in the *E. coli* system.

IV. BIOACTIVE PEPTIDE FRAGMENTS OF THE CAP37 PROTEIN

A bioactive portion of the CAP37 protein is defined as a peptide fragment of at least about 5 consecutive amino acids derived from the CAP37 protein coding sequence (FIG. 7) or the mature CAP37 protein (SEQ ID NO:9) which has chemotactic or lipopolysaccharide-binding or antibacterial properties (Example 11–14). As used herein, the term "peptide derived from CAP37" refers to a peptide that contains a bioactive portion of the CAP37 protein. Thus, a peptide derived from CAP37 may be a peptide that consists of at least 5 consecutive amino acids from the CAP37 protein coding sequence or may be a peptide that contains at least 5 consecutive amino acids front the CAP37 protein coding sequence in its sequence. Examples of the latter include sequences such as SEQ ID NO:29 (Example 12), sequences that contain a CAP37 bioactive portion attached to sequences designed to provide for some additional property, such as solubility, and CAP37 sequences in which one or more amino acids have been substituted with another amino acid to provide for some additional property, such as to remove/add amino acids capable of disulfide bonding, to increase its bio-longevity or to alter its cytotoxicity. Examples of peptides derived from CAP37 include the sequences found in SEQ ID NO:1 to SEQ ID NO:9 and SEQ ID NO:29. In any case, the peptide must possess the bioactive property, such as monocyte chemotactic, LPS-binding or antibacterial.

One method of identifying bioactive fragments is described in Examples 10 and 11. In this method, the CAP37 protein coding sequence is fragmented by digestion with DNAse I (Example 10-A). The CAP37 protein coding sequence could also be fragmented using specific restriction endonucleases, such as HaeIII which has 19 cut sites in the coding sequence. These fragments are then ligated into a vector which allows identification of in-frame fusions by a simple plate assay (Example 10-B). The presence of CAP37 protein coding DNA sequences can be verified in the clones utilizing colony hybridization. The in-frame fusions represent candidate CAP37 peptides which can be assayed for their chemotactic, antibiotic and lipopolysaccharide binding properties as described in Example 11.

Glycosylation and other post-translational modifications may not be required to detect these activities, thus expression of these peptides in *E. coli* is the method of choice. However, the fusions of the bioactive peptides to β-galactosidase can also be expressed in yeast or mammalian cells essentially as described above and in Example 9.

Another method of identifying bioactive fragments of CAP37 is described in Examples 12, 13 and 14. Because the amino acid sequence of the mature CAP37 protein is given above, it is possible to synthesize, using standard peptide synthesis techniques, peptide fragments chosen to be homologous to regions of the CAP37 protein and to modify these fragments by inclusion, deletion or modification of particular amino acids residues in the derived sequences. Thus, creation of an extremely large number of peptides derived from CAP37 is possible. However, selection of the particular sequences that provide bioactive activity is not straight-forward.

This invention discloses peptides derived from the mature CAP37 protein having chemotactic activity for monocytes, peptides derived from the mature CAP37 protein having antibacterial or bactericidal activity and peptides derived from the mature CAP37 protein having LPS-binding activity. Interestingly, the regions of the mature CAP37 protein that produce chemotactic fragments are different from those that produce either antibacterial or LPS-binding fragments. In particular, peptides derived from the 115th to 122nd amino acid region of CAP37, the 133rd to 141st amino acid region of CAP37 and the 451th to 51st amino acid region of CAP37 possess chemotactic activity. Preferred chemotactic peptides are those amino acid sequences that possess monocyte chemotactic activity and comprise those sequences defined in the Sequence Listing by SEQ ID NO:1, SEQ ID NO:3 and SEQ ID NO:5, most preferably those that consist of those sequences defined in the Sequence Listing by SEQ ID NO:2, SEQ ID NO:4 AND SEQ ID NO:6. Further, peptides derived from the 23rd–42nd amino acid region of the mature CAP37 protein possess antibacterial activity and/or LPS-binding activity. Preferred antibacterial and/or LPS-binding peptides are those that possess either antibacterial and/or LPS-binding activity and comprise those amino acid sequences defined in the Sequence Listing by SEQ ID NO:7, most preferably the peptide consisting of SEQ ID NO:8. Surprisingly, these fragments appear to possess antibacterial activity against many bacteria (both gram negative and gram positive) that the purified nature protein is not active against as well as possessing enhanced activity against bacteria such as *Salmonella typhimurium* and *Escherichia coli*. These peptide fragments have further advantages over the mature CAP37 protein: their small size permits essentially unlimited production of these compounds (the preferred size is approximately 2500 to 3000 daltons) and their therapeutic use is not limited due to the potential hazards, such as being infectious, associated with using human blood products.

Example 10

Preparing Cloned Peptide Fragments
A. DNA Fragment Digestion.

The amplified 6a.1 CAP37 cDNA described above in Example 9 is modified by treatment with EcoRI methylase under standard conditions (Promega). The DNA is phenol/chloroform extracted and ethanol precipitated. The modified DNA is suspended in a standard digest buffer (0.5M Tris HCl, pH 7.5; 1 mg/ml BSA; 10 mM MnCl2) to a concentration of about 1 mg/ml and digested with DNAse I at room temperature for various times (1–5 minutes). These reaction conditions were determined from a prior calibration study, in which the incubation time required to produce predominantly 100–200 basepair fragments was determined. The material was extracted with phenol/chloroform before ethanol precipitation. The fragments in the digest mixture were blunt-ended using DNA Polymerase I (Maniatis et al.) and ligated with the EcoRI linkers. The fragments were then digested with EcoRI under standard conditions (Promega). The resultant fragments were analyzed by electrophoresis (5–10 V/cm) on 1.2% agarose gels, using PhiX174/HaeIII and lambda/HindIII size markers. The 50–200 bp fraction was eluted onto NA45 strips (Schleicher and Schuell), which were then placed into 1.5 ml microbes with eluting solution (1M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 µl TE buffer (0.01M Tris HCl, pH 7.5, 0.001M EDTA).
B. Cloning the Digest Fragments.

The pUC7 plasmid (Messing) is modified to encode a collagenase (EC 3.4.24.3, from *Clostridium histolyticum*, available from Boehringer Mannheim) cleavage site using the following linker (SEQ ID NO:27):

```
GAT CCG CCT GCA GGC CCT GTA AGC TTG AGG
    GC GGA CGT CCG GGA CAT TCG AAC TCC AGC T
```

BamHI                    HindIII           SalI.

Insertion of the above linker between the BamHI and SalI sites of the pUC7 plasmid results in the introduction of a collagenase cleavage site (Pro Ala | Gly Pro Val), and a diagnostic HindIII site into the plasmid (designated pUC7-C). Further, the linker maintains a contiguous open reading frame into the β-galactosidase protein coding sequence. The phosphorylated oligonucleotides are synthesized by standard methods. The oligonucleotides are then mixed in an equimolar amount, heated and renatured by cooling to form the above duplex linker.

The pUC7-C plasmid is digested with EcoRI and treated with calf-intestinal phosphatase (Promega). The digest fragments from Part A were introduced into the EcoRI site by mixing 0.5–1.0 µg EcoRI-cleaved pUC7-C, 0.3–3 µl of the above sized fragments, 0.5 µl 10× ligation buffer (Maniatis et al.), 0.5 µl DNA ligase (200 units), and distilled water to 5 µl. The mixture was incubated overnight at 14° C.

The ligation mixtures are then transformed into *E. coli* strain JM101 and plated on YT media (Gibco) containing ampicillin (100 µg/ml) at a density of 300–500 colonies per plate. The plates are replica-plated to X-gal indicator plates (Miller), YT+amp, and to nitrocellulose filters (Grunstein et al.). Blue colonies are scored on the X-gal indicator plates and indicate possible in-frame fusions of an inserted DNA fragment (Part A) to the lacZ gene contained in the vector. The nitrocellulose filters are screened as follows. The amplified 6a.1 cDNA is digested with the restriction enzyme HaeIII under standard reaction conditions (New England Biolabs): the 6a.1 cDNA has 19 HaeIII sites. The resulting DNA fragments are then phenol/chloroform extracted and precipitated with ethanol. The DNA is resuspended and radioactively labelled by nick-translation (Bethesda Research Laboratories). The nitrocellulose filters are hybridized with the labelled 6a.1 cDNA as previously described (Grunstein et al.). The filters are then washed and subjected to autoradiography.

pUC7-C vectors which contain inserts from the 6a.1 cDNA will test positive by this screen. These positive colonies are further screened by comparison to the colonies on X-gal plates. Bacterial colonies which test positive for the presence of a fragment of the 6a.1 cDNA and are blue are candidates for in-frame fusions of fragments of the CAP37 coding sequence to β-galactosidase.

These candidates are picked to master plates. The candidates are inoculated into YT+ampicillin (Maniatis et al.) and grown to mid-log phase. The cultures are combined in groups of 5. The combined cells are pelleted by centrifugation and suspended in lysis buffer (10 mM Tris, pH=7.4, containing 2% Triton X-100™, with 1% aprotinin added just before use). The resuspended cells are frozen in liquid nitrogen, then thawed, resulting in substantially complete cell lysis. The lysate is treated with DNaseI to digest bacterial DNA, as evidence by a gradual loss of viscosity in the lysate. Non-solubilized material is removed by centrifugation.

SEPHAROSE 4B beads conjugated with anti-beta galactosidase are purchased from Promega. The beads are packed in a column and washed successively with phosphate-buffered saline with 0.02% sodium azide and 10 ml TX buffer (10 mM Tris buffer, pH 7.4, 1% aprotinin). The clarified lysate material is loaded on the SEPHAROSE column, the ends of the column are closed, and the column is placed on a rotary shaker for 2 hrs. at room temperature and 16 hours at 4° C. After the column settles, it is washed with TX buffer. The CAP37 protein fragments are released by collagenase cleavage (Schoitissek et al.; Ullmann). The eluent is then concentrated by ultrafiltration.

Example 11

Characterization of CAP37 Protein Fragments
A. Identification of CAP37 fragments having chemotactic properties.

The eluents generated in Example 10 are evaluated for their effects on human monocyte chemotaxis by the method of Cates et al. Briefly, one filter at a time is placed in the Boyden chamber (Neuroprobe, Bethesda Md.). The eluent to be analyzed for its chemotactic activity is placed in the lower chamber. A cell suspension of monocytes is placed in the upper compartment. The filled chambers are then briefly spun in a Sorvall centrifuge, covered to prevent evaporation, and incubated at 37° C. for approximately 120 minutes.

The filters are then removed from the Boyden chamber, stained, and fixed. The number of monocytes adhering to the chemoattractant side of the filter represent a fraction of the cells that have migrated through the filter in response to the chemoattractant. The number of monocytes in a 5×5 mm grid is counted for 10 randomly selected high-power fields (10×ocular, 45×objective) for each filter and an average cell number per grid value determined.

The number of cells migrating in response to buffered HBSS (Hank's Balanced Salt Solution; Gibco, Grand Island N.Y.) alone is also determined and is subtracted from the average number of cells per grid migrating in response to the potential chemoattractant. The number of cells migrating in response to the CAP37 protein, also determined as just described, is used as a positive control to represent 100% chemotactic activity. The eluents are evaluated as the percent of the control chemotactic activity as follows:

$$100 \times \frac{\text{corrected average number of cells per grid eluent}}{\text{corrected average number of cells per grid } CAP37}$$

An average of three filters per eluent are tested in addition to the above controls. When a pool of eluent is identified as containing a chemotactic agent, the clones comprising the pool are individually tested in the above manner to identify the clone(s) responsible for the chemoattractant property.

B. Identification of CAP37 fragments having lipopolysaccharide-binding properties and/or antibiotic activity.

Pooled eluent is prepared as described in Example 10-A. The eluents are tested for lipopolysaccharide neutralizing capacity using the Limulus Amebocyte Lysate (LAL) Assay as previously described by Warren et al. Briefly, the pooled eluent sample is diluted 1:1 in normal saline (USP Abbott Laboratories, Chicago Ill.) and added to serial two-fold dilutions, made in normal saline, of E. coli lipopolysaccharide (Whitaker Bioproducts, Inc., Walkersville, Md.) contained in wells of a 96 well microtiter plate (Flow Laboratories, McLean Va.). The mixtures are incubated for approximately 3 hours at 37° C. followed by the addition of reconstituted LAL (Whittaker Bioproducts, Inc., Walkersville, Md.). The reactions are incubated for 1 hour at 37° C. and then read using a microplate reader (Flow Laboratories, McLean Va.) set at 380 nm.

To evaluate LPS neutralization capacity of the eluent, the results of the above assays are plotted and the LPS concentration needed to produce 50% of the maximal increase in $O.D._{380}$, i.e. the maximum O.D. produced in the presence of excess LPS, is determined by interpolation. This value is called the 50% limulus gelatin response ($LR_{50}$; Warren et al.).

Each microtiter plate has the following two controls: (i) a saline control, that is, no potential neutralizing agent; and, (ii) a dilution of purified CAP37 protein as a neutralizing agent control. $LR_{50}$ values elevated above the saline control indicate potential LPS neutralizing peptide fragments of the CAP37 protein. When a pool of eluent is identified as containing a potential LPS neutralizing agent, the clones comprising the pool are individually tested in the above manner to identify the clone(s) responsible for the LPS neutralizing property.

Pooled eluent can also be tested for antibiotic activity using, for instance the assay for determining bactericidal activity as outlined in Example 13. When a pool of eluent is identified as containing a potential antibiotic CAP37 fragment, the clones comprising the pool can be individually tested in the same manner to identify the clone(s) responsible for the antibiotic property.

C. Characterization of Identified Clones.

The CAP37-encoding inserts of clones identified as of interest for either chemotactic or LPS binding properties are sequenced using dideoxynucleotide double-strand sequencing (Pharmacia Sequencing Kit, Pharmacia). Universal primers, corresponding to vector sequences which flank the inserts, are employed in the sequencing reactions. The insert sequences are then aligned with the complete CAP37 sequence to identify the locations of these regions of interest in the corresponding CAP37 protein sequence.

Example 12

Identification of Synthesized Peptide Fragments having Chemotactic Activity

The amino acid sequence of CAP37 was compared to that of elastase and cathepsin G, two serine proteases with which CAP37 has close homology. Because neither elastase nor cathepsin G exhibit monocyte chemotaxis, stretches of the CAP37 molecule which were the least homologous to either cathepsin G or elastase were selected as fragment likely to have monocyte chemotactic activity. Three such fragments:

Peptide 1, F-Q-S-Q-N-P-G-V-S-T-V (Amino acids 43–53; SEQ ID NO:6);

Peptide 2, S-I-S-S-M-S-E-N-G (Amino acids 72–80; SEQ ID NO:28); and

Peptide 3, S-Q-H-S-G-G-R-L-S-R-F-P-R-F (A peptide derived from CAP37 (amino acids 130–143) in which 132aa has been changed from Arg to His; SEQ ID NO:29) were identified and synthesized using standard peptide synthesis techniques.

The three peptides were tested for chemotactic activity towards monocytes using the modified Boyden Chamber technique described in Example 2. The monocyte chemotactic activity of each peptide fragment at concentrations ranging from $10^{-7}$ to $10^{-13}$M was compared with Geys buffer (negative control), FMLP $10^{-8}$M (positive control) and purified CAP37 $10^{-9}$M (positive control). Peptides 1 and 3 showed chemotactic activity for monocytes while peptide 2 did not. The effect of peptide 1 on monocyte chemotaxis is illustrated in Table 2 while the effect of peptide 3 on monocyte chemotaxis is illustrated in Table 3. The results with both peptides 1 and 3 show that significant chemotaxis occurs at $10^{-10}$M concentration.

TABLE 2

Effect of Peptide #1 on Monocyte Chemotaxis

| Chemoattractant Conc. | Distance migrated in μm |
|---|---|
| $10^{-7}$M peptide #1 | 57.2 |
| $10^{-8}$M peptide #1 | 51.5 |
| $10^{-9}$M peptide #1 | 57.7 |
| $10^{-10}$M peptide #1 | 63.5 |
| $10^{-11}$M peptide #1 | 51.3 |
| $10^{-12}$M peptide #1 | 50.2 |
| $10^{-8}$M FMLP | 86.2 |
| $10^{-9}$M CAP 37 | 78.4 |
| Geys buffer | 45.8 |

TABLE 3

Effect of Peptide #3 on Monocyte Chemotaxis

| Chemoattractant Conc. | Distance migrated in μm |
|---|---|
| $10^{-8}$M peptide #3 | 46.5 |
| $10^{-9}$M peptide #3 | 52.0 |
| $10^{-10}$M peptide #3 | 66.6 |
| $10^{-11}$M peptide #3 | 52.8 |
| $10^{-12}$M peptide #3 | 50.5 |
| $10^{-13}$M peptide #3 | 50.2 |
| $10^{-8}$M FMLP | 91.4 |
| $10^{-9}$M CAP 37 | 73.6 |
| Geys buffer | 43.9 |

Figure 11:
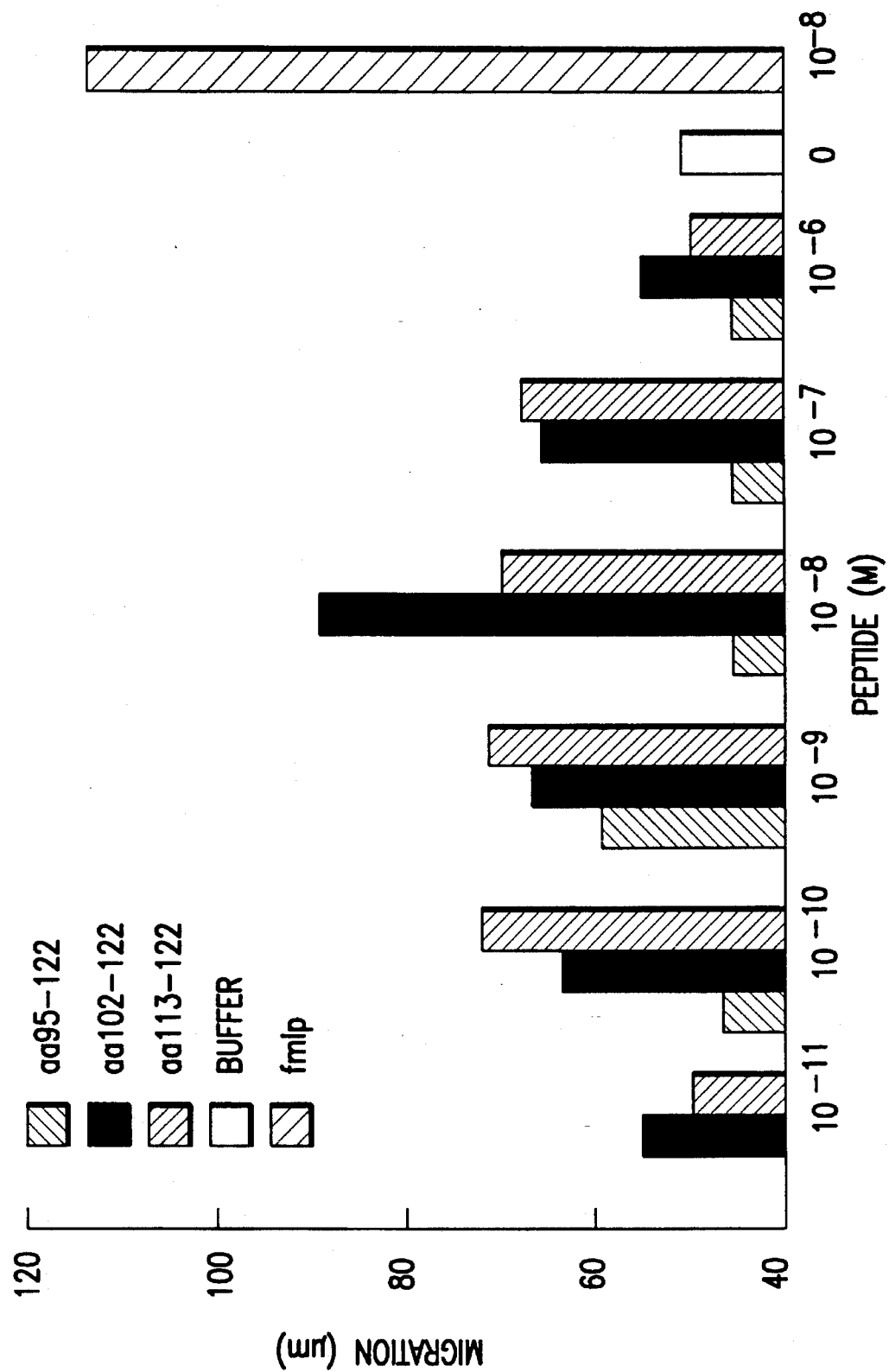
FIG. 11 shows a plot of the data which demonstrates the chemotactic properties of peptides derived from the 113th to 122nd amino acid region of the mature CAP37 protein.

To further ascertain the identity of peptides derived from CAP37 that have monocyte chemotactic activity, the following peptide fragments of CAP37 were synthesized using standard peptide synthesis techniques: 38-53aa; 95-122aa; 102-122aa; 113-122aa; and 130-146aa; in which the numbers refer to the amino acid positions in the mature CAP37 protein (SEQ ID NO:9). Each of these peptide fragments were tested as above for monocyte chemotactic activity. The peptide derived from CAP37 having aa102-122 exhibited two-thirds the monocyte chemotactic activity of the mature CAP37 protein. Further, lengthening this peptide to 95-122aa virtually destroyed the chemotactic effect whereas shortening the peptide to 113-122aa reduced the chemotactic activity, although this fragment still possessed reasonable activity. The effect of 95-122aa, 102-122aa, and 113-122aa at various concentration on monocyte chemotaxis is shown in FIG. 11.

Example 13

Identification of Synthesized Peptide Fragments having Antibiotic Activity

To identity, peptides derived from the mature CAP37 protein that have antibiotic activity, various peptide fragments were synthesized using standard peptide synthesis techniques. These peptides were tested, using the following procedure, to determine the extent, if any, of bactericidal activity for each fragment.

An overnight culture of *Salmonella typhimurium* (or other microorganism of interest, if desired) is set up by inoculating one colony in 5 ml of LB Broth (LB Broth consists of 10 g BACTO tryptone (DIFCO), 5 g BACFO yeast (DIFCO) and 5 g NaCl made up to 1 L with endotoxin free water; add 15 g of BACTO agar (DIFCO) to this broth to make LB agar (autoclave). The culture is incubated at 37° C. with rotation. 100 μl of this overnight culture is then transferred to 5 ml of fresh LB Broth and incubated at 37° C. with rotation for 2 hours. Four ml of this log phase culture is then transferred to a sterile cuvette and the optical density is read at 520 min. Dilutions of the microorganism are then made in tryptone saline (5 g BAOTO tryptone (DIFCO) and 5 g NaCl made up to 1 L with endotoxin free water, pH 5.5) to give a final concentration of $5 \times 10^3$ organisms/ml (an O.D. reading of 0.25 at 520 mm is equivalent to $1 \times 10^8$ organisms/ml). The microorganisms are placed at 4° C. until ready to be used.

The stock solutions of peptides are stored at −20° C. at concentrations of 1 mg/ml of endotoxin-free water. The peptide is diluted out in tryptone saline to the desired concentration. 100 μl of the peptide is added to each well of the microtitre plate (Corning) and then 100 μl of the bacterial suspension (well vortexed) is added. Each assay point is set up in triplicate. 100 μl of a control, consisting of bacteria and tryptone saline (T=0) in the absence of peptide is plated out on LB agar plates. The microliter plate is then incubated at 37° C. for 1 hour. At the end of the incubation time, 100 μl of each sample is plated out on LB agar plates. The T=60 control (consisting of bacteria and tryptone saline in the absence of peptide) is plated out last. The plates are incubated overnight, and the number of colony forming units (CFU) are determined.

The % killed is determined as follows:

$$\% \text{ killed} = 100 \times \frac{CFU \text{ in absence of peptide} - CFU \text{ in presence of peptide}}{CFU \text{ in absence of peptide}}$$

Figure 12:
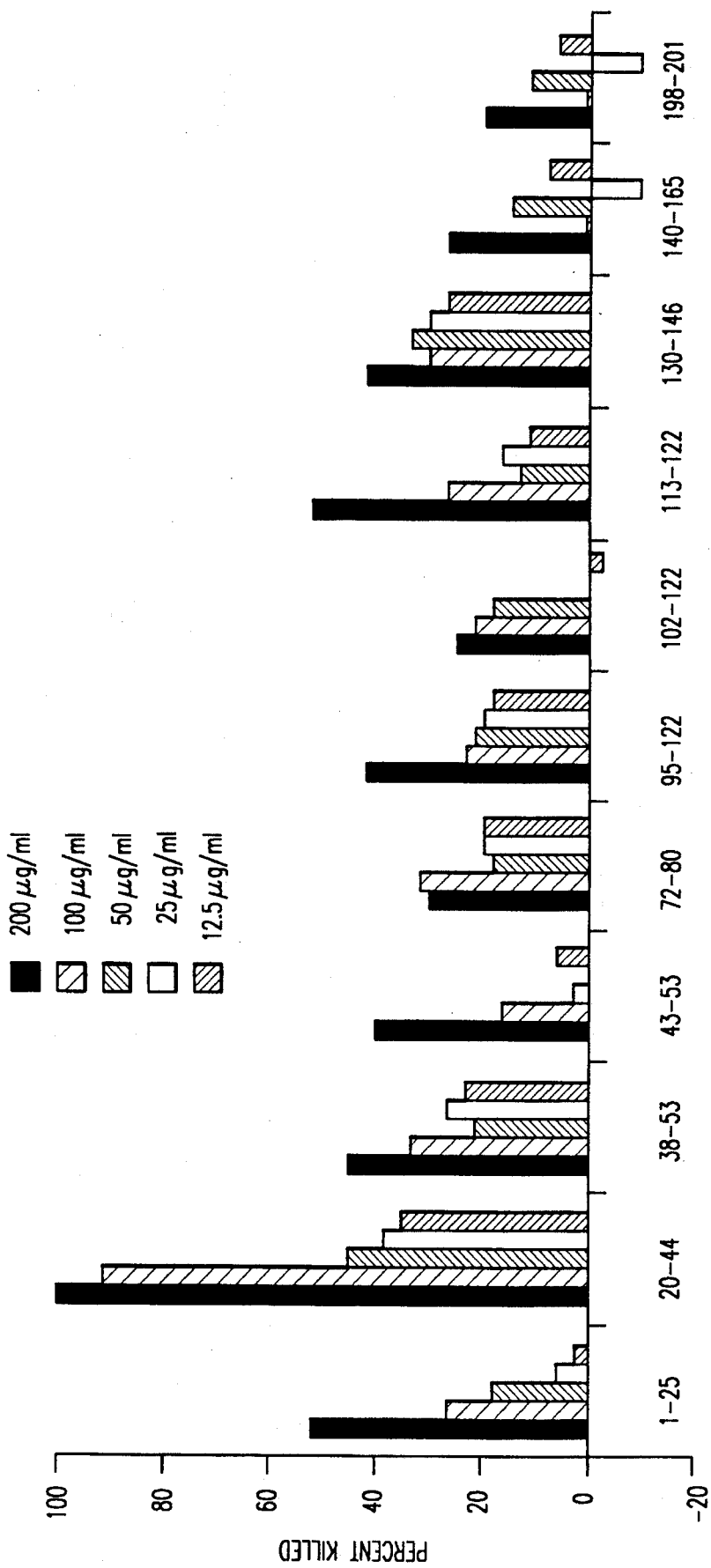
FIG. 12 shows the bactericidal effect of peptides derived from the mature CAP37 protein on *Salmonella typhimurium* SH9178.

FIG. 12 shows the bactericidal effect of peptides derived from CAP37 1-25aa; 20-44aa; 38-53aa; 43-53aa; 72-80aa;, 95-122aa, 102-122aa; 113-122aa; 130-146aa; 140-165aa and 198-201aa on *Salmonella typhimurium* SH9178 at concentration ranging from 12.5 μg/ml to 200 μg/ml. As can be seen, CAP37 fragment 20-44aa (SEQ ID NO:8) is the most potent antibiotic of these peptides; 20-44aa is an extremely potent antibiotic peptide.

Figure 13:
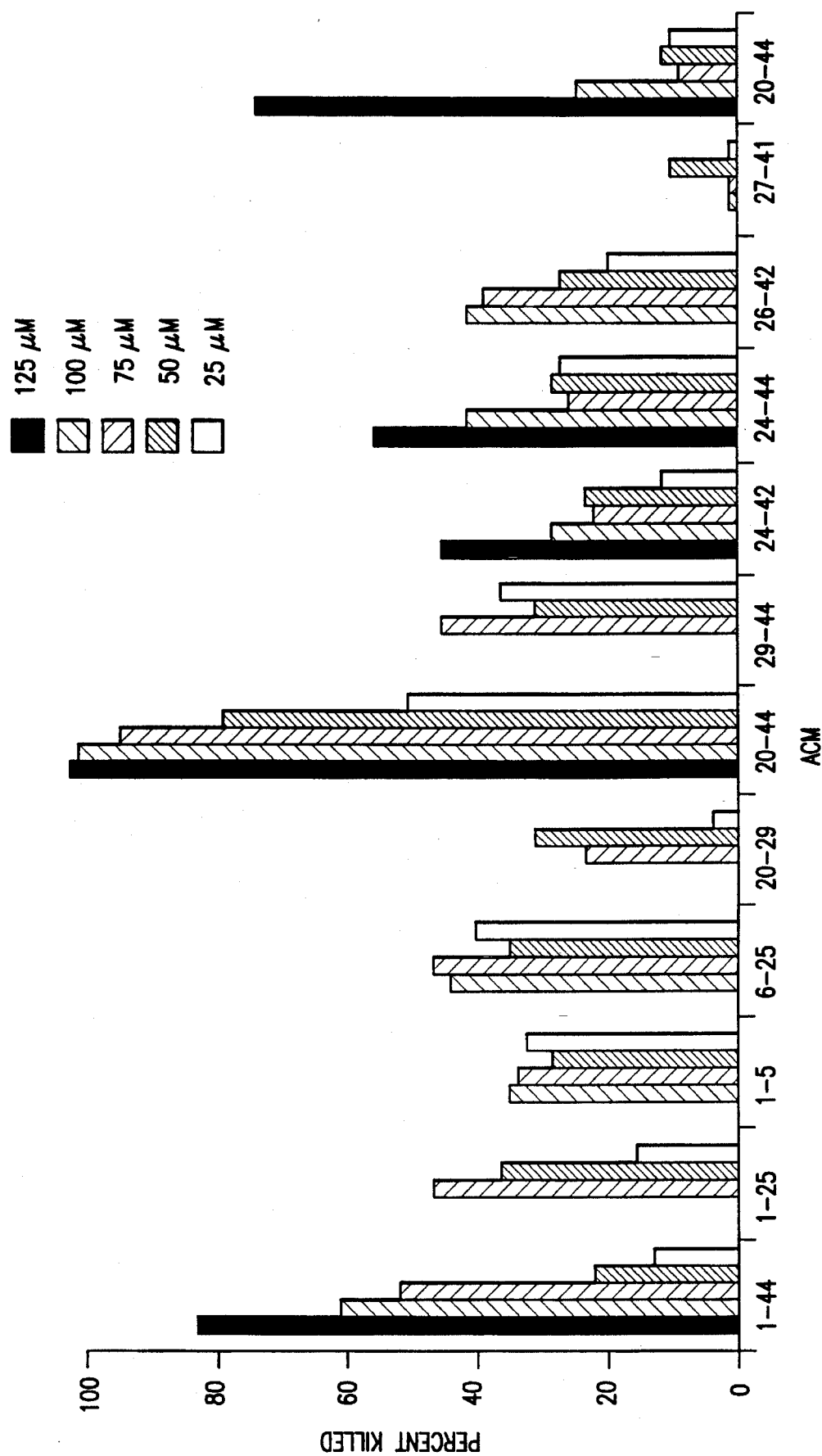
FIG. 13 shows the bactericidal effect of peptides derived from the 1st to 44th amino acid region of the mature CAP37 protein on *Salmonella typhimurium* SH9178.

To determine the minimum or critical number of residues required for antibiotic activity in the 20-44aa region, peptides of slightly greater or lesser length were synthesized also. FIG. 13 shows the bactericidal effect of peptides 1-44aa; 1-25aa; 1-5aa; 6-25aa; 20-29aa; 20-44aa;, 29-44aa; 24-42aa; 24-44aa; 26-42aa; and 27-41aa on *Salmonella typhimurium* SH9178. Strongest activity was obtained with peptide 20-44aa (SEQ ID NO:8). Peptide 1-44aa is also active but not to the same extent as peptide 20-44aa. In contrast to cathepsin G in which amino acids 1–5 of that sequence are mildly bactericidal, the first 5 amino acids of CAP37 (1-5aa) is not active at the concentrations tested.

From this data, it appears that the two cysteines at residues 26 and 42 are important for activity of the peptide. The peptide 27-41aa, which lacked both cysteines, possessed no bactericidal activity Peptide 26-42aa has minimal activity. However, this peptide, along with 24-44aa and 24-42aa, are not very soluble. Peptides 20-29 and 29-44 have no activity and peptide 1-25 is not active either. The cysteines at residues 26 and 42 may help the molecule to become cyclic, and thus enhance the peptide's ability to insert into the bacterial membrane, because of a disulfide bridge between the two crystals. To test this theory, peptide 20-44ACM was synthesized such that the cysteines at 26 and 42 have the side chain ACM added to theta to stop disulfide bridge formation and, hence, any cyclic compound formation. Thus, 20-44ACM is basically linear or stretched out. As can be seen in FIG. 13, no or very reduced antibiotic activity was obtained with this peptide, indicated that some cyclic native is required to allow insertion in the bacterial membrane. Thus, it appears that at least the amino acid sequence 23-42aa (SEQ ID NO:7) is necessary for heightened antibiotic activity.

Figure 14:
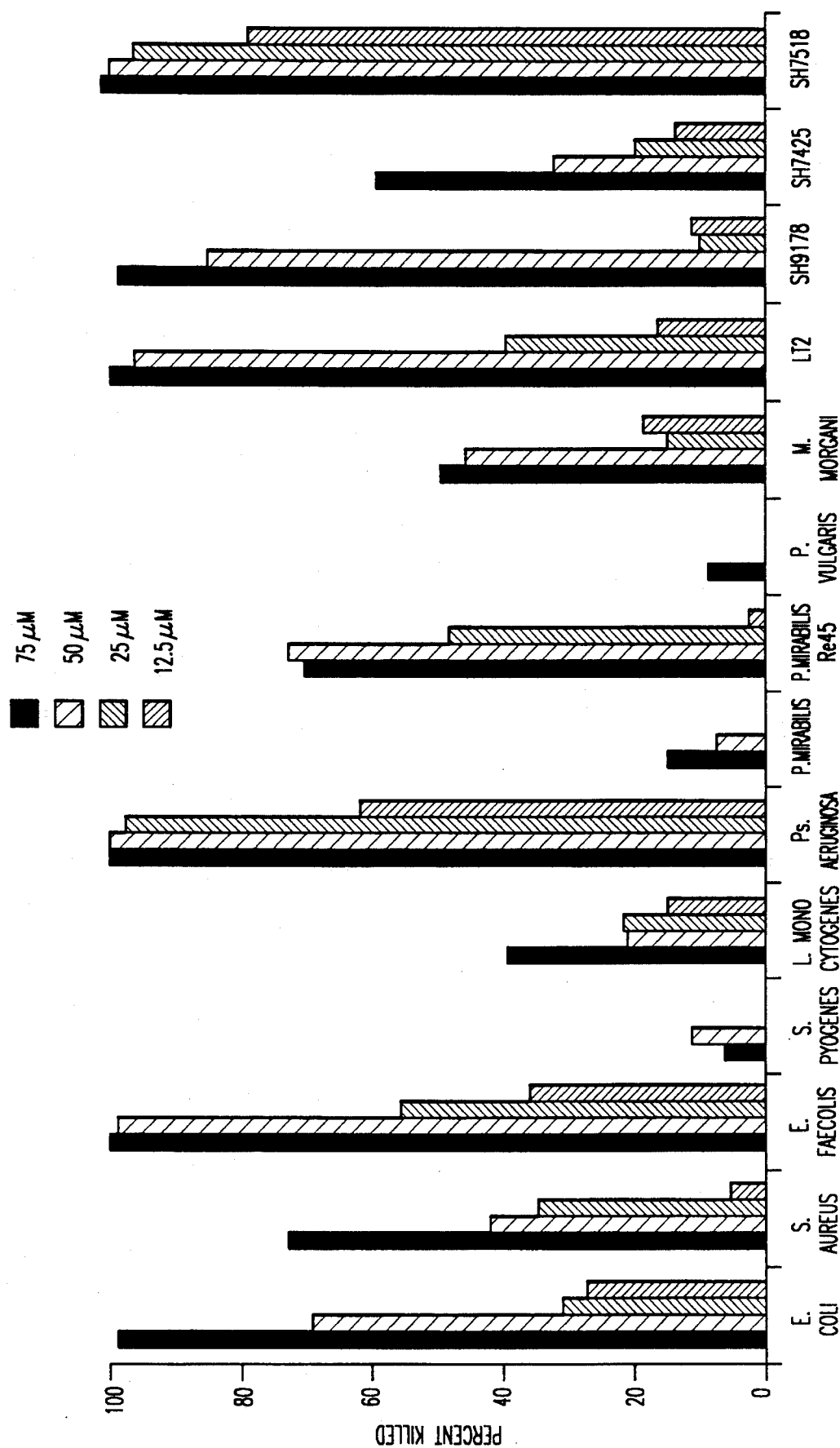
FIG. 14 shows the bactericidal effect of the peptide 20-44aa (SEQ ID NO:8) derived from the mature CAP37 protein on various gram negative and gram positive bacteria.

Antibiotic peptide 20-44aa derived from CAP37 (SEQ ID NO:8) is active against a wide assortment of bacteria, including both gram negative and positive bacteria. FIG. 14 shows the bactericidal effect of CAP37 peptide 20-44 on *Escherichia coli* (gram negative), *Staphylococcus aureus* (gram positive), *Enterococcus faecalis* (gram positive), *Streptococcus pyogenes* (gram positive), *Listeria monocytogenes* (gram positive), *Pseudomonas aeruginosa* (gram negative), *Proteus mirabilis* (gram negative), *Morganella morgani*, *Salmonella typhimurium* LT2 (wild type, gram negative), *Salmonella typhimurium* SH9178 (Rb chemotype, gram negative), *Salmonella typhimurium* (SH7518, Re chemotype, gram negative). These results indicate that CAP37 peptide 20-44 is most active against Pseudomonas, *E. faecalis, E. coli* and *Salmonella typhimurium* LT2, SH9178 and SH7518.

Table 4 shows a comparison of the bactericidal activity of peptide 20-44aa (SEQ ID NO:8) against the activity of crude granule extract (CGE) from normal human neutrophils and the activity of CAP37 itself (including values for some organisms obtained from the Shafer (1986) paper). Surprisingly, peptide 20-44aa is more active against certain bacteria (i.e., Salmonella LT2, *E. coli*, Pseudomonas, *E. faecalis*, and *Pr. mirabilis* Re45) than either the CGE or the CAP37. CAP37 was originally shown to be active mainly against *Salmonella typhimurium* and *Escherichia coli*. The peptide 20-14aa derived from the mature CAP37 protein, in addition to being very active against these two gram negative bacteria, appears to be active against many other bacteria (including some gram positives) that the purified protein is not active against. Thus, the activity of the peptide appears to be much more potent that the whole protein.

Figure 15:
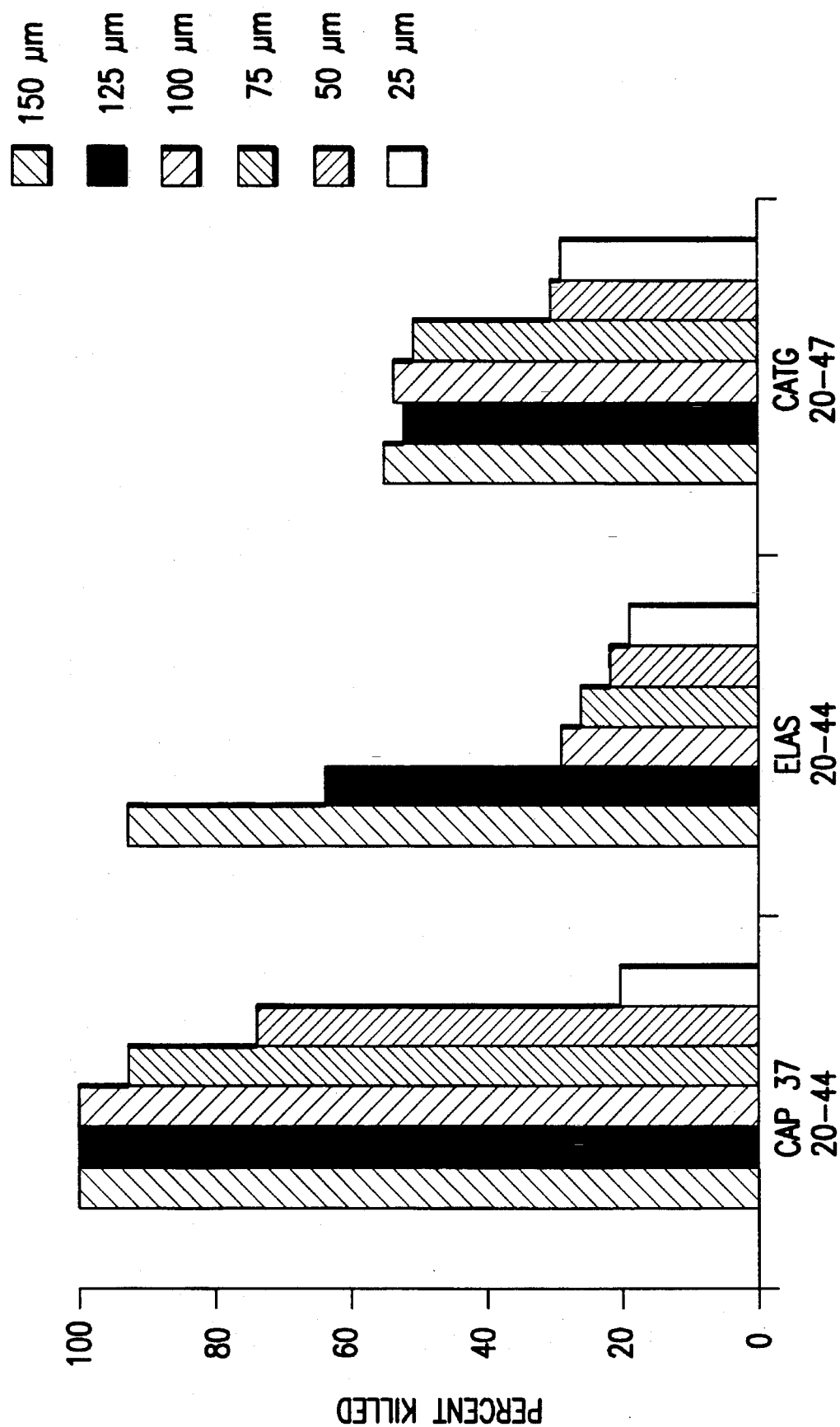
FIG. 15 shows a comparison of bactericidal activity of the peptide 20-44aa (SEQ ID NO:8) derived from the mature CAP37 protein against *Salmonella typhimurium* SH9178 with peptides derived from similar regions from cathepsin G and elastase peptide.

A comparison of the bactericidal activity of the 20-44aa protein derived from CAP37 to elastase peptide 20-44aa and cathepsin G peptide 20-47aa was undertaken, using the bactericidal assay discussed above, to ascertain if these other similar proteins had similar active sites. The results of this comparison are given in FIG. 15 and indicate that CAP37's peptide fragment, 20-44aa, is extremely active while cathepsin G, 20-27aa is not bactericidal and elastase 20-44aa is active but only at the highest concentration. Results at 100 and 125 µM LPS binds to the peptide, interfering with its antimicrobial activity.

As discussed in Example 11, peptides can be screened for lipopolysaccharide neutralizing capacity using the LAL assay also. The CAP37 peptide was diluted to the desired concentrations (from 125 ng/ml to 4000 ng/ml) in geys buffered saline pH 7 (GIBCO). To this is added the wild type LPS (RIBI IMMUNOCHEM) or Re LPS from Salmonella (David Morrison, Kansas Medical Center) so that the final concentration is 0.1, 0.5, and 1.0 ng/ml LPS. The tubes were incubated at 37° C. for between 30 to 60 minutes and then assayed in the chromogenic LAL assay.

Figure 17A:
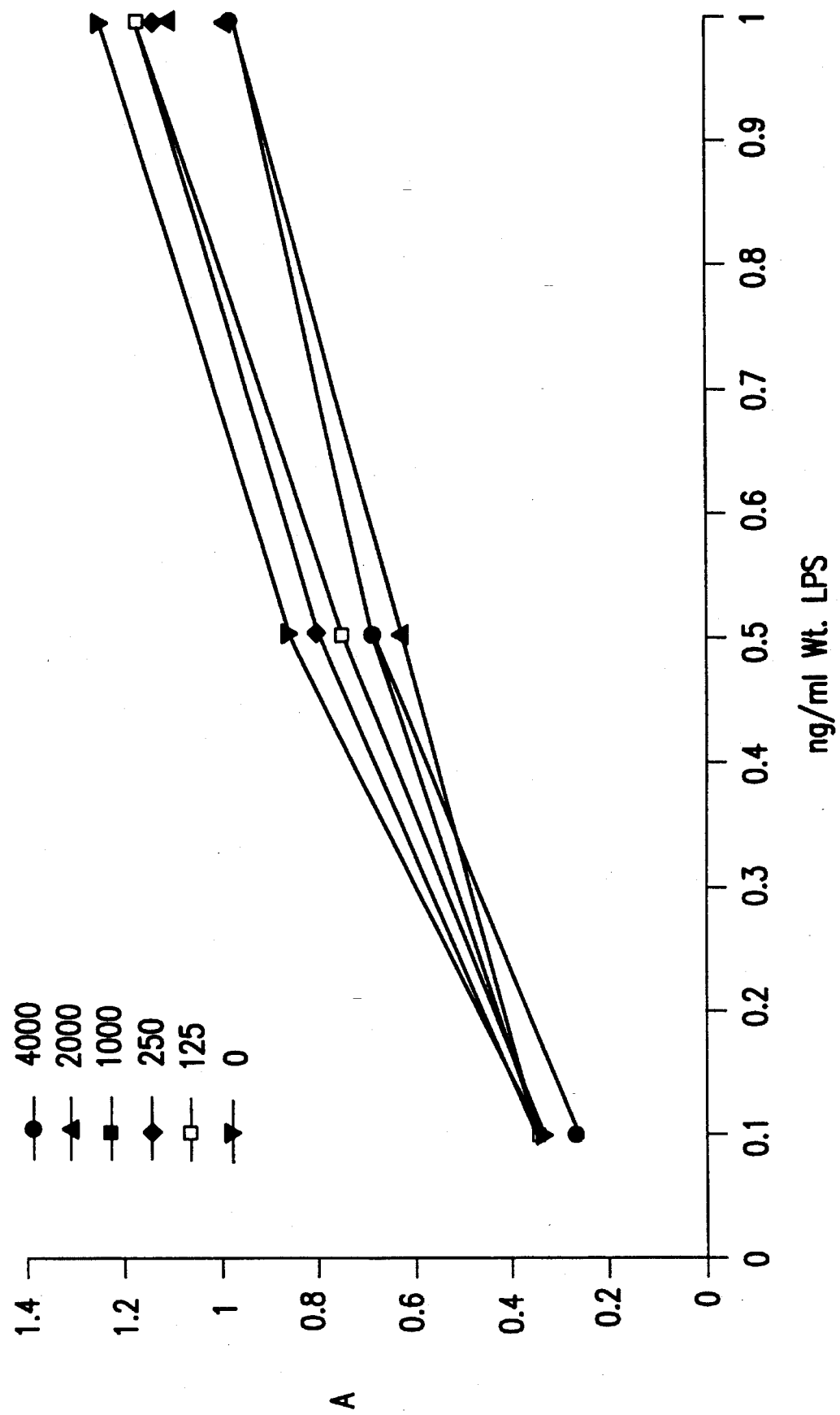
FIG. 17(A) shows the neutralization of wild type LPS activity and FIG. 17(B) shows the neutralization of ReLPS by the peptide 20-44aa (SEQ ID NO:8) derived from the mature CAP37 protein as assayed by the limulus amebocyte lysate assay.
Figure 17B:
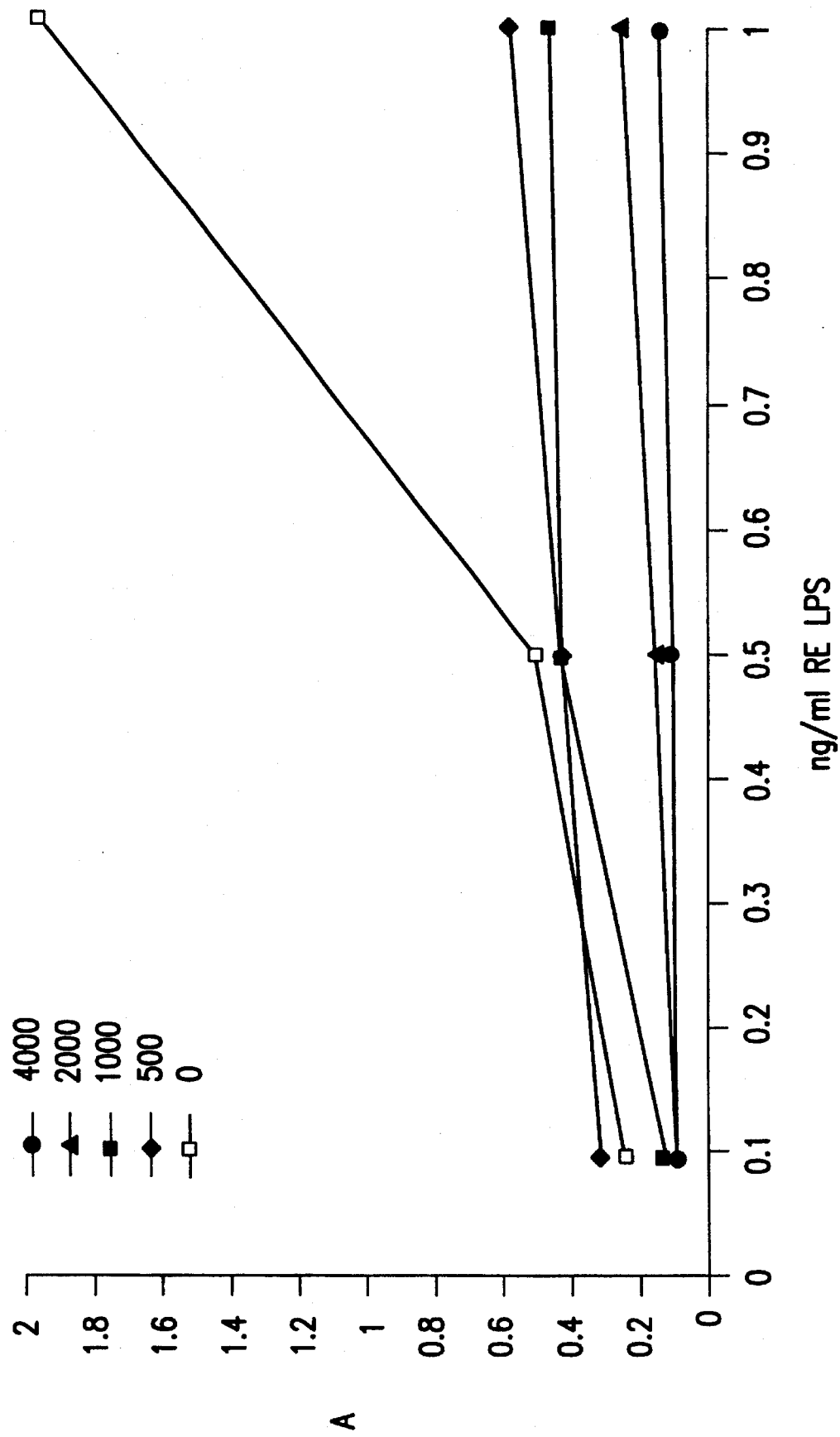

FIG. 17 shows the results of neutralization of LPS activity by peptide 20-44aa (SEQ ID NO:8) by the LAL assay. The absorbance at 405 nm in FIG. 17A indicates that the 20-44aa peptide derived from CAP37 can bind to wild type LPS, neutralizing its effect to a certain extent. However, as shown in FIG. 17B, the neutralizing effect when ReLPS is used is more dramatic. This result indicates that peptide 20-44aa is more likely to bind the rough strains of LPS and Lipid A more than smooth LPS.

V. Anti-CAP37 Antibodies

In another aspect, the invention includes an antibody which is specific against CAP37 protein or bioactive peptides derived from CAP37, or specific against CAP37 protein/peptide fusion proteins (Examples 9–14). To prepare antibodies, a host animal, such as a rabbit, is immunized with the purified CAP37 protein/peptide antigen. The host serum or plasma is collected following an appropriate time interval, and this serum is tested for antibodies specific

TABLE 4

|  | % survival with peptide 20-44 | | | % survival with CGE | | |
| --- | --- | --- | --- | --- | --- | --- |
|  | 75 uM | 50 uM | No. expts | 20 ug/ml | No. expts | % survival with CAP 37 |
| Salmonella LT2 | 1.7 | 28.5 | 1 | 45.8 | 1 | 43 (Shafer, 1986) |
| Salmonella SH9178 | 3.5 | 36.9 | 3 | 4.5 | 1 | Not done |
| Salmonella SH7426 | 31.9 | 62.5 | 2 | 17.8 | 1 | 64.3 |
| Salmonella SH7518 | 0 | 0.6 | 2 | 1 | 1 | 10.9 |
| E. coli | 0 | 24.6 | 2 | 31.2 | 3 | 4 (Shafer, 1986) |
| Ps. aeruginosa | 0 | 0 | 1 | 28.1 | 1 | 36 (Shafer, 1986) |
| E. faecalis | 0 | 16.1 | 3 | 49.8 | 2 | Not done |
| P. mirabilis Re45 | 29 | 26.8 | 1 | 59.3 | 1 | 100 (Shafer, 1986) |
| L monocytogenes | 64.6 | 65.8 | 1 | 40.2 | 1 | Not done |
| S. aureus 502A | 27.5 | 58.7 | 1 | Not done |  | Not done |
| Strep. pyogenes | 78 | 93.4 | 1 | Not done |  |  | indicate that CAP37's fragment, peptide 20-44aa, is the very much more bactericidal.

Example 14

Figure 16:
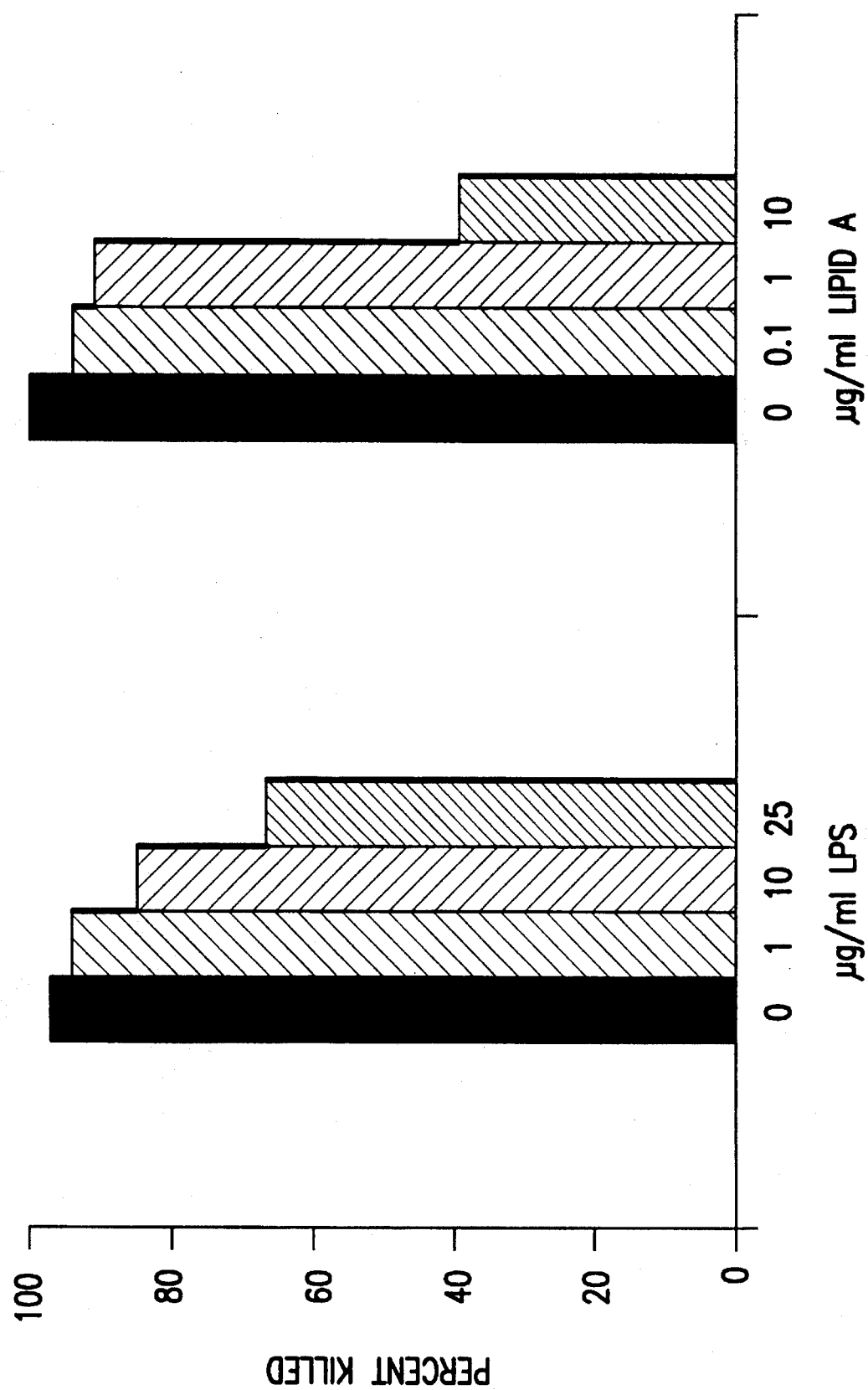
FIG. 16 shows the inhibition of the bactericidal effect of the peptide 20-44aa (SEQ ID NO:8) derived from the mature CAP37 protein on *Salmonella typhimurium* SH9178 by LPS and Lipid A.

Identification of Synthesized Peptide Fragments having Lipopolysaccharide Binding Activity To identify, those peptides derived from CAP37 having bacterial LPS-binding activity, the peptide fragments having bactericidal activity were tested to ascertain whether LPS or Lipid A inhibited that activity. FIG. 16 shows the inhibition of the bactericidal effect of peptide 20-44aa (SEQ ID NO:8) on *Salmonella typhimurium* SH9178 by wild type LPS and Lipid A. The peptide at 200 µg/ml was incubated with the indicated amounts of LPS and Lipid A and then incorporated in the bactericidal assay (Example 13). The percent killed is indicated and shows that wild type LPS, but more particularly Lipid A, can inhibit the bactericidal effect of peptide 20-44aa on SH9178. This inhibition strongly suggests that against the CAP37 protein antigen. Example 15 describes the production of rabbit serum antibodies which are specific against CAP37 protein, a peptide derived from CAP37 or protein/peptide fusion proteins.

The gamma globulin fraction or the IgG antibodies of immunized animals can be obtained, for example, by use of saturated ammonium sulfate or DEAE SEPHADEX, or other techniques known to those skilled in the art for producing polyclonal antibodies.

Alternatively, the purified antigen may be used for producing monoclonal antibodies. Here the spleen or lymphocytes from an immunized animal are removed and immortalized or used to prepare hybridomas by methods known to those skilled in the art.

Antibodies secreted by the immortalized cells are screened to determine the clones that secrete antibodies of the desired specificity (Example 15), for example, using the Western blot method (Ausubel et al.).

Example 15

Preparation of Anti-CAP37 Antibodies

The fusion protein containing the full length CAP37 protein and glutathione S-transferase (Example 9-A) is isolated from lysed bacteria. Transformed bacteria are streaked for single colonies, grown at 37° C. overnight or until colonies are apparent. Individual colonies are inoculated into 1 ml of selection media and grown overnight. Saturated overnight bacterial culture are used to inoculate cultures, which are incubated with aeration to an O.D. of about 0.5–0.6. The cells are pelleted by centrifugation, and resuspended in lysis buffer (62 mM Tris, pH 7.5 containing 5% mercaptoethanol, 2.4% SDS and 10% glycerol). The lysate is treated with DNaseI to digest bacterial DNA, as evidence by a gradual loss of viscosity in the lysate. Non-solubilized material was removed by centrifugation. The fusion protein is isolated from the bacterial lysate by treatment with immobilized-glutathione (Smith et al.).

For the isolation of CAP37/β-galactosidase fusion proteins (Examples 10 and 11), the cells are pelleted by centrifugation and suspended in lysis buffer (10 mM Tris, pH 7.4 containing 2% TRITON X-100 and 1% aprotinin added just before use). The resuspended cells are frozen in liquid nitrogen, then thawed, resulting in substantially complete cell lysis. The lysates are treated with DNaseI to digest bacterial DNA, as evidence by a gradual loss of viscosity in the lysate. Non-solubilized material is removed by centrifugation.

SEPHAROSE 4B beads conjugated with anti-beta galactosidase are purchased from Promega. The beads are packed in columns and washed successively with phosphate-buffered saline with 0.02% sodium azide and TX buffer (10 mM Tris buffer, pH 7.4, 1% aprotinin). The clarified lysates are loaded on the SEPHAROSE columns, the ends of the columns are closed, and the columns placed on a rotary shaker for 2 hours, at room temperature and 16 hours at 4° C. After the columns settle, they are washed with TX buffer. The fused proteins are eluted with 0.1M carbonate/bicarbonate buffer, pH10. The eluate from each affinity column is concentrated by ultrafiltration using, for example, CENTRICON-30 cartridges. The final protein concentrate is resuspended in PBS buffer.

The individually purified fusion proteins are injected subcutaneously in Freund's adjuvant in rabbits. 1 mg of fused protein is injected at days 0 and 21, and rabbit serum is collected on days 42 and 56.

Control rabbits are similarly immunized with purified glutathione S-transferase (Sj26) protein obtained from control bacterial lysate and purified β-galactsidase obtained from commercial sources.

Minilysates are prepared (essentially as described above for the fusion proteins but omitting the affinity purification steps) from the following transformed bacterial cultures: (1) cells transformed with the CAP37/glutathione S-transferase fusion-encoding plasmid; (2) cells transformed with the glutathione S-transferase encoding plasmid; (3) cells transformed with each of the CAP37 peptide/β-galactosidase fusion-encoding plasmids (Example 11); and, (4) cells transformed with the β-galactosidase fusion-encoding plasmid. The minilysates and purified CAP37 protein were fractionated by SDS-PAGE, and the bands transferred to nitrocellulose filters for Western blotting (Ausubel et al.).

Serum from control (Sj26) rabbits is expected to be immunoreactive with each of the Sj26 and Sj26 fused protein antigens. Serum from the animal immunized with CAP37/Sj26 fused protein is expected to be reactive with Sj26, Sj26 fused protein antigen, and purified CAP37 indicating some specific immunoreaction with CAP37. The serum from the animal immunized with CAP37/Sj26 fused protein may also immunoreact with the CAP37 peptide/β-galactosidase antigens, but is not expected to react with β-galactosidase antigen alone.

Serum from control (β-galactosidase) rabbits is expected to be immunoreactive with each of the β-galactosidase and β-galactosidase fused protein antigens. Serum from the animal immunized with CAP37/β-galaclosidase fused protein is expected to be reactive with β-galactosidase, β-galactosidase-fused protein antigen, and purified CAP37 indicating some specific immunoreaction with CAP37. The serum from the animal immunized with CAP37/β-galactosidase fused protein may also immunoreact with the CAP37 peptide/Sj26 antigens, but is not expected to react with Sj26 antigen alone.

VI. HYBRID PROTEINS CREATED WITH CAP37 PROTEIN

In another aspect, the invention includes CAP37 fused at its amino or carboxy end with a second protein or peptide to form a hybrid protein. The CAP37 protein making up the hybrid protein is preferably recombinantly produced CAP37 protein or a bioactive portion thereof, as described above.

The hybrid CAP37 protein or bioactive peptide (CAP37 protein/peptide) may be formed by chemical conjugation or by recombinant techniques. In the former method, the second peptide and CAP37 protein/peptide are modified by conventional coupling agents for covalent attachment (Duncan; Cumber).

Where CAP37 protein/bioactive peptide is used in tumor therapy, the protein/peptide may be advantageously fused with a polyclonal or monoclonal antibody specifically directed against target tumor-specific cell surface antigen(s). This fusion protein is then infused at or near the tumor site to attract monocytes to the site.

As an alternative chemical conjugation method, CAP37 protein/peptides not containing cysteine may be prepared to contain cysteine to allow disulfide coupling of the CAP37 protein to an activated second protein, thus simplifying the coupling reaction. The expression vector used for production of recombinant CAP37 bioactive peptide can be modified for insertion of an internal or a terminal cysteine codon according to standard methods of site-directed mutagenesis or oligonucleotide linker insertion.

In a preferred method, the hybrid protein is prepared recombinantly using an expression vector in which the coding sequence of the fusion peptide is joined to the CAP37 protein/bioactive peptide coding sequence. For example, an expression vector formed is designed to contain the following components: (a) a synthetic trp/lac promoter positioned appropriately ahead of a ribosome binding site that is also positioned appropriately ahead of an ATG start codon which is 5' to an cloning site; (b) the ricin A chain coding sequence (Olnes; Olnes et al.; Lamb et al.); (c) a spacer encoding sequence coding for 10 proline residues, which spaces the ricin A chain and CAP37 protein/peptide moieties; (d) the coding sequence for the CAP37 protein/peptide; and, (e) a stop codon positioned adjacent the carboxy-terminal codon of CAP37 protein/peptide. The method generally follows that used in fusing a soluble CD4 to domains 2 and 3 of pseudomonas exotoxin A, as described previously (Chaudhary).

The expression vector containing the fusion protein coding sequences is analyzed for expression of the hybrid protein. Briefly, the expression vector is cultured in a suitable bacterial host under IPTG induction conditions to a desired cell density. The cells are harvested, ruptured by sonication, and the cell material is clarified by centrifugation. The clarified material is tested for (a) chemotactic ability, to confirm CAP37 protein/bioactive peptide activity, and (b) for ribosome inhibition activity, to confirm the ricin A chain enzymatic activity.

The protein may be purified by molecular-sieve and ion-exchange chromatography methods, with additional purification by polyacrylamide gel electrophoretic separation and/or HPLC chromatography, if necessary.

The ricin/CAP37 fusion protein can be used as a very specific anti-tumor reagent for cancers of monocyte cells.

It will be appreciated from the above how other second protein-CAP37 protein/peptide fusion proteins may be prepared. One variation on the above fusion is to exchange positions of the ricin A chain and CAP37 protein/peptide coding sequences in the fusion protein expression vector. Other variations would use abrin A chain or trichosanthin rather than ricin A chain. (Olnes et al., 1982; Lifson et al., 1989; Chow et al., 1990; Collins et al., 1990).

VII. UTILITY

The cloning and expression of human CAP37 protein provides an important source of the purified protein by simplifying preparation and allowing production of large quantities of the protein.

The purified CAP37 protein, and specially bioactive peptides derived from CAP37, can be applied to wound sites resulting in a two-fold benefit: (i) the protein and certain bioactive peptides (Example 13) are strong anti-microbial agents and (ii) monocytes are attracted to the wound sit by the mature protein and certain bioactive peptides (Example 12). The CAP37 protein or bioactive peptide derived from CAP37 can be applied at a wound site by infusion, allowing the protein to form a gradient in surrounding tissue by diffusion. Alternatively, the protein or peptide can be administered by routes known to one skilled in the art, such as parenterally (including subcutaneously) or orally (such as by tablet, in a microencapsulated form or in a mouthwash). Importantly, the CAP37 protein or peptide derived from CAP37 can be formulated in a topical medication, such as pastes, gels, creams, and ointments, by standard methods (e.g., West et al.). The topical medication is then applied at the wound site: this method of application allows a controlled to release of the protein at the wound site. Such topical formulations may also contain other components, such as antibiotics or epidermal growth factor (Brown et al.), to facilitate healing. Further, the application may contain more than one peptide derived from CAP37 to advantageously take advantage of peptides having chemotactic activity and peptides having antibacterial activity that is superior to that of the mature CAP37 protein. Of course, as known in the art, these peptides may be designed with amino acid residues attached to either one or both termini which will not alter its chemotactic and/or antibiotic function but will increase its longevity and alter its cytotoxicity.

Because of the bactericidal activity of these compounds, particularly the peptides derived from CAP37 disclosed above, against a wide variety of both gram negative and gram positive bacteria, these compounds are particularly useful for treating infection caused by bacteria, particularly various Pseudomads, *E. faecalis.*, *E. coli*, and *Salmonella typhimurium* bacterial species. Because these peptides are active against gram negative bacteria, these compounds are especially useful in dental applications.

The purified CAP37 protein, or a bioactive peptide thereof, may also be used in treating other diseases such as cancers. CAP37 can be administered through systemic injection, intravesical administration or may be injected locally into an accessible tumor mass. The route of administration would depend on the nature and size of the tumor or other diseased tissue being treated. CAP37, or a bioactive peptide thereof, could be administered using protocols adjuvant immunotherapy currently using bacterial vaccines such as Bacille Calmette-Guerin (BCG) or *Corynebacterium parvum*. Such protocols are well known in the art. (Regelson et al., 1986;; Martinez-Piñeiro et al., 1988; Cumming et al., 1989).

Essentially, an effective amount of CAP37 or peptide derived from CAP37 would be mixed with a suitable pharmaceutically acceptable solvent or carrier and administered to an animal by one of the routes of administration established for other adjuvants such as BCG. CAP37 could be encapsulated in multilamellar phospholipid vesicles, or other encapsulating material, to aid in administration. Depending on the area to be treated, the route of administration and the close, CAP37 might be administered without a carrier.

An effective dose of CAP37 or peptide derived from CAP37 would vary depending upon the route of administration and the area to be treated. CAP37 or a peptide derived from CAP37 could be administered systemically or intraperitoneally in a dose of 100 ng/kg. Effective doses preferably fall in the range of 1 µg to 1 mg per treatment.

Because of its ability specifically to attract monocytes, CAP37 or peptides derived from CAP37 could be used to treat any disease involving monocyte localization. These diseases would include neoplastic diseases, rheumatoid arthritis, hepatitis, chronic obstructive pulmonary disease, chronic periodontal disease, parasitic diseases such as malaria, tuberculosis and leprosy. CAP37 could also be used to treat diseases involving defects of monocyte chemotaxis such as Wiscott Aldrich syndrome, chronic mucocutaneous candidiasis, chronic granulomatous disease, Chediak Higashi syndrome, specific granule deficiency, systemic lupus erythematosus and herpes simplex.

Since the CAP37 protein or peptides derived from CAP37 bind bacterial lipopolysaccharide, CAP37 protein, or a bioactive peptide thereof, may also provide an effective treatment for endotoxemia. A solution of the CAP37 protein may be parenterally applied to a patient to bind endotoxins that are circulating in blood and facilitate their clearing. Particularly useful is prophylactic treatment before surgery with the CAP37 nature protein or LPS-binding peptides derived front CAP37 to prevent endotoxemia. Topical treatment prior to eye surgery may be especially useful to control the gram negative bacterial associated with eye infections.

Further, as discussed above (Section VI), hybrid proteins containing CAP37 protein, or bioactive portions thereof, may be useful in tumor therapies.

Purified antibodies specifically reactive with the CAP37 mature protein or bioactive peptides derived from CAP37 can be used to detect the presence and amount of CAP37 and/or CAP37 peptides. Further, these antibodies can be used to screen patients for diagnostic purposes.

The examples illustrate, but are in no way intended to limit the present invention. Although the invention has been described with reference to specific methods and compositions, it will be apparent to one skilled in the art how various modifications and applications of the methods may be made without departing from the invention.

REFERENCES

Ausubel, F. M., et al., CURRENT PROTOCOLS IN MOLECULAR BIOLOGY, John Wiley and Sons, Inc., Media Pa.
Benfey, P. N., et al., *J. Biol. Chem.* 262:5377 (1987).
Berman, P. W., et al., *Science* 222:524 (1983).
Bing, D. H., et al., *Ann. N.Y. Acad. Sci.* 485:104 (1984).
Boyum, A., *J. Clin. Lab. Invest.* 21:SUP97:77 (1968).
Bradford et al., *Anal. Biochem.* 72:248–254, 1976.
Brake, A. J., U.S. Pat. No. 4,870,008, issued Sep. 26, 1989.
Brake, A. J., et al., *Proc. Natl. Acad. Sci. USA* 81:5330 (1984).
Brown, G. L., et al., *Ann. Surg.* 208(6):788 (1988).
Cates, K. L., et al., p67 IN LEUKOCYTE CHEMOTAXIS, edited by J. I. Gallin and P. G. Quie, Raven Press New York (1978).
Chambers, W. M., et al., *Met. Immunol. Immunopathol.* 5:197 (1983).
Chang, C. N., et al., *Mol. Cell. Biol.* 6:1812 (1986).
Chaudhary, V. K., et al., *Nature*, 335:369 (1988).
Chirgwin, J. M., et al., *Biochem.*, 18:5294 (1979).
Chow, C. C., et al., *J. Biol. Chem.*, 265:8670–8674 (1990).
Collins, E. J., et al., *J. Biol. Chem.* 265:8665–8669 (1990).
Cumber, J. A., et al., *Methods in Enzymology*, 112:207 (1985).
Cumming et al., *Brit. J. Urology*, 63:259–263 (1989).
Duncan, R. J. S., et al., *Anal Biochem*, 182:68 (1983).
Gershenfeld, H. K., et al., *Science* 232:854 (1986).
Gillis, S., et al., *Behring. Inst. Mitt.*, 83:1 (1988).
Gluzman, Y., *Cell*, 23:175 (1981).
Gray, P. W., et al., *Nature*, 295:503 (1982).
Grunstein, M., et al., *Methods in Enzymology*, 68:379 (1979).
Guarente, L., *Methods in Enzymology*, 101:181 (1983).
Hayashi, H., et al., *Int. Rev. Cytol.*, 89:179 (1984).
Herbert, W. J., in THE HANDBOOK OF EXPERIMENTAL IMMUNOLOGY, Second Edition, edited by D. M. Weir, Blackwell Scientific Publications, Oxford, England (1973).
Hopp, T. P., et al., *Proc. Natl. Acad. Sci. USA*, 78:3824 (1981).
Hoylaerts, M., et al., *FEBS Lett.*, 204:83 (1986).
Hurley, J. V., et al., in *ACUTE INFLAMMATION*, second edition, p109, published by Churchill Livingstone, Edinburgh (1983).
Johnson, D. M. A., et al., *FEBS*, 166:347 (1984).
Jones, E. W., *Ann. Rev. Genetics*, 18:233 (1984).
Kawaguchi, T., et at., Am. J. Pathol. 11.5:307 (1984).
Kingsman, A. J., et al., U.S. Pat. No. 4,615,974, issued Oct. 7, 1986.
Kopchick, J. J., et al., U.S. Pat. No. 4,828,987, issued May 9, 1989.
Kurjan, J., et al., U.S. Pat. No. 4,546,082, issued Oct. 8, 1985.
Lacy, M. J., et al., *J. Immunol. Methods*, 87:169 (1986).
Lamb, F. I., et al., *Eur J Biochem.*, 148:265 (1985).
Laemmli, *Nature*, 227:680 (1970).
Lemontt, J. F., et al., *DNA*, 4:419 (1985).
Lifson, J. D. et al., U.S. Pat. No. 4,795,739, issued Jan. 3, 1989.
Lobe, C. G., et al., *Science*, 232:858 (1986).
Maniatis, T., et al., MOLECULAR CLONING: A LABORATORY MANUAL, Cold Spring Harbor Laboratories, Cold Spring Harbor, N.Y. (1982).
Martinez-Pieiro et al., *Eur. Urol.*, 15:146–149, 1988.
Maruyama, T., et al., *Nucleic Acids Res.*, 14(s) r151–r197.
McGrogan, M., et al., *Biotech.*, 6:172 (1988 A).
McGrogan, M., et al., *J. Exp. Med.*, 168:2295 (1988 B).
McIvor, R. S., et al., *Mol. Cell. Biol.*, 5:1349 (1985).
Messing, J., *Methods in Enzymology*, 101:20 (1983).
Miller, J. H., EXPERIMENTS IN MOLECULAR GENETICS, Cold Spring Harbor Laboratories, Cold Spring Harbor N.Y. (1972).
Moriarty, A. M., et al., U.S. Pat. No. 4,777,240, issued Oct. 11, 1988.
Mullis, K., U.S. Pat. No. 4,683,202, issued Jul. 28, 1987.
Nieman, M. A., et al., *Biochem.*, 23:2482 (1984).
Oeda, K., et al., U.S. Pat. No. 4,766,068, issued Aug. 23, 1988.
Okano, K., et al., *J. Biochem.*, 102:13 (1987).
Okayama, H., et al., *Mol. Cell. Biol.*, 2:161 (1982).
Olnes, S., *Nature*, 328:474 (1987).
Olnes, S., et al., in MOLECULAR ACTION OF TOXINS AND VIRUSES, (Elsevier, 1982), Chapter 3.
Olnes, S., et al., "Toxic Lectins and Related Proteins", in Cohen, P. et al. (eds.), MOLECULAR ACTION OF TOXINS AND VIRUSES, Elsevier Biomedical Press, 1982, pp. 55–105.
Patzer, E. J., et al., *J. Virol.*, 58:884 (1986).
Pereira, H. A., et al., *J. Immunol. Methods*, 117:115 (1989).
Regelson et at., *Clin. Sci. Rev.* for (1): 29–42, 1986.
Revel, M., et al., U.S. Pat. No. 4,889,803, issued Dec. 26, 1989.
Salvesen, G., et al., *Biochem.*, 26:2289 (1987).
Scharf, S. J., et al., *Science*, 233:1076 (1986).
Scholtissek, S., et al., *Gene*, 62(1):55 (1988).
Seed, B., *Proc. Natl. Acad. Sci. USA*, 84:8573 (1987).
Shafer, W. M., et al., *infect. Immun.*, 45:29 (1984).
Shafer, W. M., et al., *Infect. Immun.*, 53:651 (1986).
Sinha, S., et al., *Proc. Natl. Acad. Sci. USA*, 84:2228 (1987).
Simonsen, C. C., et al., *Proc. Natl. Acad. Sci. USA*, 80:2495 (1983).
Smith, D. B., et al., *Gene*, 67(1):31 (1988).
Snyderman et al., *J. Exp Med.*, 134:1131 (1971).
Snyderman, R., et al., p73 in LEUKOCYTE CHEMOTAXIS, edited by J. I. Gallin and P. G. Quie, Raven Press N.Y. (1978).
Spitznagel, J. K., et al., *J. Immunol.*, 139:1291 (1987).
Thim, L., et al., *FEBS Lett.*, 212:2, 307 (1987).
Towbin et al., *Proc. Natl. Acad. Sci. USA*, 76:4350–4354 (1979).
Ullmann, A., *Gene*, 29(1-2):27 (1984).
Urlaub, G., et al., *Proc. Natl. Acad. Sci USA*, 77:4216 (1980).
Warren, H. S., et al., pages 341–348 in DETECTION OF BACTERIAL ENDOTOXINS WITH THE LIMULUS AMEBOCYTE LYSATE TEST, published by Alan R. Liss, Inc. (1987).
West, G. III, et al., U.S. Pat. No. 4,781,871, issued Nov. 1, 1988.
Wilkinson, P. C., et al., in ACUTE INFLAMMATION, second edition, p119, published by Churchill Livingstone, Edinburgh (1983).
Woo, S. L. C., *Methods in Enzymology*, 68:389 (1979).
Wood, W. I., et al., *Nature*, 312:330 (1984).
Woodbury, R. G., et al., *Biochem.*, 17:811 (1978).
Wright, D. G., et al., *J. Immunol.*, 119:1068 (1977).
Zigmond, S., et al., *J. Exp. Med.*, 137:387 (1973).
Zsebo, K. M., et al., *J. Biol. Chem.*, 261:5858 (1986).

It is claimed:

1. A method for treating diseases involving monocyte localization or defects of monocyte chemotaxis which can be treated by increasing monocyte localization in an animal comprising the step of administering to said animal a therapeutic composition comprising a monocyte chemotactic amount of a monocyte chemotactic protein consisting of the amino acid sequence as defined in SEQ ID NO:9 or a monocyte chemotactic portion thereof, thereby treating diseases involving monocyte localization or defects of monocyte chemotaxis.

2. A method for increasing the migration of monocytes to a particular tissue site, comprising the step of administering to said tissue site a therapeutic composition comprising a monocyte chemotactic protein consisting of the amino acid sequence as defined in SEQ ID NO:9 or a monocyte chemotactic portion thereof in a concentration to create a chemotactic gradient from the site of between $10^{-8}$M to $10^{-11}$M, thereby increasing the migration of monocytes to the particular tissue site.

3. A method of treating a wound which can be treated by increasing monocyte localization comprising the step of applying to said wound a topical medication comprising a wound treating and monocyte chemotactic amount of a monocyte chemotactic protein consisting of the amino acid sequence as defined in SEQ ID NO:9 or a chemotactic portion thereof, thereby treating the wound.

4. The method of claim 3, wherein the topical medication further comprises epidermal growth factor to promote wound healing.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 115-122aa of mature CAP37 protein ( x i ) SEQUENCE DESCRIPTION: SEQ ID NO:1:

Ala Thr Val Glu Ala Gly Thr Arg
1               5

( 2 ) INFORMATION FOR SEQ ID NO:2:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 102-122aa of mature CAP37 protein ( x i ) SEQUENCE DESCRIPTION: SEQ ID NO:2:

Thr Ser Ser Val Thr Ile Leu Pro Leu Pro Leu Gln Asn Ala Thr Val
1               5                   10                  15

Glu Ala Gly Thr Arg
            20

( 2 ) INFORMATION FOR SEQ ID NO:3:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 133-141aa of mature CAP37 protein ( x i ) SEQUENCE DESCRIPTION: SEQ ID NO:3:

Ser Gly Gly Arg Leu Ser Arg Phe Pro
1               5                   10

( 2 ) INFORMATION FOR SEQ ID NO:4:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 130-143aa of mature CAP37 protein ( x i ) SEQUENCE DESCRIPTION: SEQ ID NO:4:

Ser Gln Arg Ser Gly Gly Arg Leu Ser Arg Phe Pro Arg Phe
1               5                   10

( 2 ) INFORMATION FOR SEQ ID NO:5:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 45-51aa of mature CAP37 protein ( x i ) SEQUENCE DESCRIPTION: SEQ ID NO:5:

Ser Gln Asn Pro Gly Val Ser
1               5

( 2 ) INFORMATION FOR SEQ ID NO:6:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 43-53aa of mature CAP37 protein ( x i ) SEQUENCE DESCRIPTION: SEQ ID NO:6:

Phe Gln Ser Gln Asn Pro Gly Val Ser Thr Val
1               5                   10

( 2 ) INFORMATION FOR SEQ ID NO:7:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 23-42aa of mature CAP37 protein ( x i ) SEQUENCE DESCRIPTION: SEQ ID NO:7:

Arg His Phe Cys Gly Gly Ala Leu Ile His Ala Arg Phe Val Met Thr
1               5                   10                  15
Ala Ala Ser Cys
                20

( 2 ) INFORMATION FOR SEQ ID NO:8:

( i ) SEQUENCE CHARACTERISTICS:
( A ) LENGTH: 25 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 20-44aa of mature CAP37 protein ( x i ) SEQUENCE DESCRIPTION: SEQ ID NO:8:

```
Asn Gln Gly Arg His Phe Cys Gly Gly Ala Leu Ile His Ala Arg Phe
1               5                   10                  15
Val Met Thr Ala Ala Ser Cys Phe Gln
            20              25
```

( 2 ) INFORMATION FOR SEQ ID NO:9:

( i ) SEQUENCE CHARACTERISTICS:
      ( A ) LENGTH: 222 amino acids
      ( B ) TYPE: amino acid
      ( D ) TOPOLOGY: linear ( i i ) MOLECULE TYPE: protein ( v ) FRAGMENT TYPE: internal ( x i ) SEQUENCE DESCRIPTION: SEQ ID NO:9:

```
Ile Val Gly Gly Arg Lys Ala Arg Pro Arg Gln Phe Pro Phe Leu Ala
1               5                   10                  15
Ser Ile Gln Asn Gln Gly Arg His Phe Cys Gly Gly Ala Leu Ile His
            20                  25                  30
Ala Arg Phe Val Met Thr Ala Ala Ser Cys Phe Gln Ser Gln Asn Pro
        35                  40                  45
Gly Val Ser Thr Val Val Leu Gly Ala Tyr Asp Leu Arg Arg Arg Glu
    50                  55                  60
Arg Gln Ser Arg Gln Thr Phe Ser Ile Ser Ser Met Ser Glu Asn Gly
65                  70                  75                  80
Tyr Asp Pro Gln Gln Asn Leu Asn Asp Leu Met Leu Leu Gln Leu Asp
                85                  90                  95
Arg Glu Ala Asn Leu Thr Ser Ser Val Thr Ile Leu Pro Leu Pro Leu
            100                 105                 110
Gln Asn Ala Thr Val Glu Ala Gly Thr Arg Cys Gln Val Ala Gly Trp
        115                 120                 125
Gly Ser Gln Arg Ser Gly Gly Arg Leu Ser Arg Phe Pro Arg Phe Val
    130                 135                 140
Asn Val Thr Val Thr Pro Glu Asp Gln Cys Arg Pro Asn Asn Val Cys
145                 150                 155                 160
Thr Gly Val Leu Thr Arg Arg Gly Gly Ile Cys Asn Gly Asp Gly Gly
                165                 170                 175
Thr Pro Leu Val Cys Glu Gly Leu Ala His Gly Val Ala Ser Phe Ser
            180                 185                 190
Leu Gly Pro Cys Gly Arg Gly Pro Asp Phe Phe Thr Arg Val Ala Leu
        195                 200                 205
Phe Arg Asp Trp Ile Asp Gly Val Leu Asn Asn Pro Gly Pro
    210                 215                 220
```

( 2 ) INFORMATION FOR SEQ ID NO:10:

( i ) SEQUENCE CHARACTERISTICS:
      ( A ) LENGTH: 26 amino acids
      ( B ) TYPE: amino acid
      ( D ) TOPOLOGY: linear ( i i ) MOLECULE TYPE: peptide ( v ) FRAGMENT TYPE: N-terminal ( x i ) SEQUENCE DESCRIPTION: SEQ ID NO:10:

```
      Met  Thr  Arg  Leu  Thr  Val  Leu  Ala  Leu  Leu  Ala  Gly  Leu  Leu  Ala  Ser
      1              5                        10                       15

Ser  Arg  Ala  Gly  Ser  Ser  Pro  Leu  Leu  Asp
                     20                   25
```

( 2 ) INFORMATION FOR SEQ ID NO:11:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

```
      Cys  Gln  Val  Ala  Gly  Trp  Gly
      1                   5
```

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CUGCCTCCYT GRTTYTGRAT                                                  20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

ARGAAGGGRA AYTGNCKGGG                                                  20

( 2 ) INFORMATION FOR SEQ ID NO:14:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..150

( x i ) SEQUENCE DESCRIPTION: SEQ ID NO:14:

```
ATG  CTG  CTT  CAG  AGG  TTT  GTC  AAC  GTG  ACT  GTG  ACC  CCC  GAG  GAC  CAG    48
Met  Leu  Leu  Gln  Arg  Phe  Val  Asn  Val  Thr  Val  Thr  Pro  Glu  Asp  Gln
1                   5                        10                       15

TGT  CGC  CCC  ACC  AAC  GTG  TGC  ACC  GGT  GTG  CTC  ACC  CGC  CGC  GGT  GGC    96
Cys  Arg  Pro  Asn  Asn  Val  Cys  Thr  Gly  Val  Leu  Thr  Arg  Arg  Gly  Gly
                    20                   25                       30
```

```
ATC  TCG  AAT  GGG  GAC  GGG  GGC  ACC  CCC  CTC  GTC  TGC  GAG  CCG  CTG  GCC    144
Ile  Cys  Asn  Gly  Asp  Gly  Gly  Thr  Pro  Leu  Val  Cys  Glu  Gly  Leu  Ala
          35                       40                      45

CAC  GGC                                                                          150
His  Gly
     50
```

( 2 ) INFORMATION FOR SEQ ID NO:15:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Leu  Leu  Gln  Arg  Phe  Val  Asn  Val  Thr  Val  Thr  Pro  Glu  Asp  Gln
 1              5                       10                      15

Cys  Arg  Pro  Asn  Asn  Val  Cys  Thr  Gly  Val  Leu  Thr  Arg  Arg  Gly  Gly
               20                       25                      30

Ile  Cys  Asn  Gly  Asp  Gly  Gly  Thr  Pro  Leu  Val  Cys  Glu  Gly  Leu  Ala
          35                       40                      45

His  Gly
     50
```

( 2 ) INFORMATION FOR SEQ ID NO:16:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:16:

```
Ala  Gly  Thr  Arg  Cys  Gln  Val  Ala  Gly  Trp  Gly  Ser  Gln  Arg  Ser  Gly
 1              5                       10                      15

Gly  Arg  Leu  Ser  Arg  Phe  Pro  Arg  Phe  Val  Asn  Val  Thr  Val  Thr  Pro
               20                       25                      30

Glu  Asp  Gln  Cys  Arg
               35
```

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
TGYCARGTNG CNGGNTGGGG                                                              20
```

( 2 ) INFORMATION FOR SEQ ID NO:18:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
   ( A ) NAME/KEY: CDS
   ( B ) LOCATION: 6..125

( x i ) SEQUENCE DESCRIPTION: SEQ ID NO:18:

```
TGTAG GTT GCG GGT TGG GGG AGC CAG CAC AGT GGG GGG CGT CTC TCC           47
      Val Ala Gly Trp Gly Ser Gln His Ser Gly Gly Arg Leu Ser
       1               5                   10

CGT TTT CCC AGG TTC GTC AAC GTG ACT GTG ACC CCC GAG GAC CAG TGT          95
Arg Phe Pro Arg Phe Val Asn Val Thr Val Thr Pro Glu Asp Gln Cys
 15              20              25                      30

CGC CCC AAC AAC GTG TGC ACC GGT GTG CTC                                 125
Arg Pro Asn Asn Val Cys Thr Gly Val Leu
                 35              40
```

( 2 ) INFORMATION FOR SEQ ID NO:19:

( i ) SEQUENCE CHARACTERISTICS:
      ( A ) LENGTH: 40 amino acids
      ( B ) TYPE: amino acid
      ( D ) TOPOLOGY: linear ( i i ) MOLECULE TYPE: protein ( x i ) SEQUENCE DESCRIPTION: SEQ ID NO:19:

```
Val Ala Gly Trp Gly Ser Gln His Ser Gly Gly Arg Leu Ser Arg Phe
 1               5                   10                  15

Pro Arg Phe Val Asn Val Thr Val Thr Pro Glu Asp Gln Cys Arg Pro
             20              25                  30

Asn Asn Val Cys Thr Gly Val Leu
             35              40
```

( 2 ) INFORMATION FOR SEQ ID NO:20:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:20:

TGTCAGGTTG CGGGTTGGGG GAGCCAGCAC AGTGGGGGGC GTCTCTCCCG         50

( 2 ) INFORMATION FOR SEQ ID NO:21:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:21:

ATCGTTGGCG GCCGGAAGGC G         21

( 2 ) INFORMATION FOR SEQ ID NO:22:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:22:

TTGGGCCCTG GCCCCGGTCG G                                                                 21

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

ATGATCGTTG GCGGCCGGAA GGCG                                                              24

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

ATGGGGAGG GTGGGTCC                                                                      18

( 2 ) INFORMATION FOR SEQ ID NO:25:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CCGGAATTCC AAGCTTCCAC CATGACCCGG CTGACAGTCC TGG                                          43

( 2 ) INFORMATION FOR SEQ ID NO:26:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CCGGATCCTC TAGACCCTAG GCTGGCCCCG GTCCCGG                                                37

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

-continued

GATCCGCCTG CAGGCCCTGT AAGCTTGAGG 30

( 2 ) INFORMATION FOR SEQ ID NO:28:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:28:

Ser Ile Ser Ser Met Ser Glu Asn Gly
1               5

( 2 ) INFORMATION FOR SEQ ID NO:29:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:29:

Ser Gln His Ser Gly Gly Arg Leu Ser Arg Phe Pro Arg Phe
1               5                               10